US010391100B2

(12) United States Patent
Manfredi

(10) Patent No.: US 10,391,100 B2
(45) Date of Patent: Aug. 27, 2019

(54) COMBINATION OF AURORA KINASE INHIBITORS AND ANTI-CD20 ANTIBODIES

(71) Applicant: Millennium Pharmaceuticals, Inc., Cambridge, MA (US)

(72) Inventor: Mark Manfredi, Newton, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/387,740

(22) Filed: Dec. 22, 2016

(65) Prior Publication Data

US 2017/0296551 A1    Oct. 19, 2017

Related U.S. Application Data

(62) Division of application No. 15/052,966, filed on Feb. 25, 2016, which is a division of application No. 12/638,018, filed on Dec. 15, 2009.

(60) Provisional application No. 61/203,509, filed on Dec. 22, 2008.

(51) Int. Cl.
| | |
|---|---|
| *A61K 31/55* | (2006.01) |
| *A61K 39/395* | (2006.01) |
| *A61K 45/06* | (2006.01) |
| *C07K 16/28* | (2006.01) |
| *A61K 39/00* | (2006.01) |

(52) U.S. Cl.
CPC .............. *A61K 31/55* (2013.01); *A61K 39/00* (2013.01); *A61K 39/395* (2013.01); *A61K 39/3955* (2013.01); *A61K 45/06* (2013.01); *C07K 16/2887* (2013.01); *A61K 2039/505* (2013.01); *C07K 2317/24* (2013.01)

(58) Field of Classification Search
CPC .. A61K 2300/00; A61K 31/55; A61K 39/395; A61K 2039/505; A61K 39/00; A61K 39/3955; A61K 45/06; C07K 16/2887; C07K 2317/24
See application file for complete search history.

(56) References Cited

U.S. PATENT DOCUMENTS

| | | | |
|---|---|---|---|
| 4,099,012 A | 7/1978 | Gschwend | |
| 4,469,633 A | 9/1984 | Trybulski | |
| 4,481,142 A | 11/1984 | Fryer et al. | |
| 5,166,151 A | 11/1992 | Freidinger et al. | |
| 5,210,082 A | 5/1993 | Bock et al. | |
| 5,747,487 A | 5/1998 | Albright et al. | |
| 6,057,329 A | 5/2000 | Davis et al. | |
| 6,277,844 B1 | 8/2001 | Spector et al. | |
| 6,727,251 B2 | 4/2004 | Bebbington et al. | |
| 7,572,784 B2 | 8/2009 | Claiborne et al. | |
| 7,718,648 B2 | 5/2010 | Claiborne et al. | |
| 8,026,246 B2 | 9/2011 | Claiborne et al. | |
| 8,399,659 B2 | 3/2013 | Claiborne et al. | |
| 9,102,678 B2 | 8/2015 | Claiborne et al. | |
| 9,173,846 B2 | 11/2015 | Mittal et al. | |
| 9,765,076 B2 | 9/2017 | Claiborne et al. | |
| 9,765,078 B2 | 9/2017 | Claiborne et al. | |
| 9,988,384 B2 | 6/2018 | Claiborne et al. | |
| 2002/0009444 A1* | 1/2002 | Grillo-Lopez ... | A61K 39/39541 424/142.1 |
| 2003/0022885 A1 | 1/2003 | Bebbington et al. | |
| 2003/0055068 A1 | 3/2003 | Bebbington et al. | |
| 2005/0256102 A1 | 11/2005 | Claiborne et al. | |
| 2006/0074074 A1 | 4/2006 | Ohtsuka et al. | |
| 2007/0104785 A1 | 5/2007 | Navale et al. | |
| 2007/0149561 A1 | 6/2007 | Dhanak et al. | |
| 2007/0185087 A1 | 8/2007 | Claiborne et al. | |
| 2008/0045501 A1 | 2/2008 | Claiborne et al. | |
| 2008/0167292 A1 | 7/2008 | Claiborne et al. | |
| 2009/0023743 A1 | 1/2009 | Michaelides et al. | |
| 2009/0299060 A1 | 12/2009 | Claiborne et al. | |
| 2010/0152170 A1 | 6/2010 | Mjalli et al. | |
| 2011/0039826 A1 | 2/2011 | Ramanan et al. | |
| 2011/0091483 A1 | 4/2011 | Beall | |
| 2011/0245234 A1 | 10/2011 | Armitage et al. | |
| 2011/0312942 A1 | 12/2011 | Claiborne et al. | |
| 2011/0312943 A1 | 12/2011 | Claiborne et al. | |
| 2015/0166545 A1 | 6/2015 | Claiborne et al. | |
| 2016/0271249 A1 | 9/2016 | Manfredi | |
| 2019/0031662 A1 | 1/2019 | Claiborne et al. | |

FOREIGN PATENT DOCUMENTS

| | | |
|---|---|---|
| CN | 1824307 A | 8/2006 |
| EP | 0014470 A2 | 8/1980 |
| EP | 0273697 A2 | 7/1988 |
| WO | WO-97/19065 A1 | 5/1997 |
| WO | WO-97/32883 A1 | 9/1997 |
| WO | WO-98/28281 A1 | 7/1998 |
| WO | WO-98/058926 A1 | 12/1998 |
| WO | WO-00/67754 A1 | 11/2000 |

(Continued)

OTHER PUBLICATIONS

ClinicalTrials.gov. publication (2007).*
Alvarez, R.H. et al., MLN8237 (alisertib), an investigational Aurora A Kinase inhibitor, in patients with breast cancer: Emerging phase 2 results, Cancer Research, 72(24 suppl. 3): 543s, 6 pages, (2012).
Bischoff, J.R. et al., A homologue of *Drosophila aurora* kinase is oncogenic and amplified in human colorectal cancers, European Molecular Biology Organization, 17(11):3062-3065 (1998).
Cantor, E.H. et al., Interaction of calcium channel blockers with non-neuronal benzodiazepine binding sites, Proceedings of the National Academy of Sciences, 81:1549-1552 (1984).
Carmena, M. et. al., The Cellular Geography of Aurora Kinases, Nature, 4:842-854 (2003).
Cervantes, A. et al, Phase I pharmacokinetic/pharmacodynamic study of MLN8237, an investigational, oral, selective aurora a kinase inhibitor, in patients with advanced solid tumors, Clin. Cancer Res., 18(17):4764-74 (2012).

(Continued)

*Primary Examiner* — Savitha M Rao
(74) *Attorney, Agent, or Firm* — Choate, Hall & Stewart LLP; Brenda Herschbach Jarrell; Kristen C. Buteau

(57) ABSTRACT

The present invention relates to methods for the treatment of hematological malignancies. In particular, the invention provides methods for treatment of hematological malignancies by administering Aurora kinase inhibitors in combination with anti-CD20 antibodies.

5 Claims, No Drawings

(56) References Cited

FOREIGN PATENT DOCUMENTS

| | | |
|---|---|---|
| WO | WO-01/10462 A1 | 2/2001 |
| WO | WO-02/068415 A1 | 9/2002 |
| WO | WO-02/094834 A1 | 11/2002 |
| WO | WO-03/013545 A1 | 2/2003 |
| WO | WO-2005/037843 A1 | 4/2005 |
| WO | WO-2005/111039 A3 | 4/2006 |
| WO | WO-2006/055831 A2 | 5/2006 |
| WO | WO-2006/070198 A1 | 7/2006 |
| WO | WO-2007/076348 A2 | 7/2007 |
| WO | WO-2008/005266 A2 | 1/2008 |
| WO | WO-2008/021038 A2 | 2/2008 |
| WO | WO-2008/063525 A1 | 5/2008 |
| WO | WO-2009/070652 A1 | 6/2009 |
| WO | WO-2009/114703 A2 | 9/2009 |

OTHER PUBLICATIONS

Chiattone, C. et al., MLN8237 (alisertib), an investigational selective inhibitor of aurora a kinase, versus investigators choice of pralatrexate or gemcitabine in patients with relapsed/refractory peripheral T-cell lymphoma: a phase 3 study, Rev. Bras. Hematol. Hemoter., 34(Supl. 2) 89-326: 300-301(2012).

ClinicalTrials.gov, View of NCT00500903 on Jul. 12, 2007, clinicaltrials.gov/archive/NCT00509-03/2007_07_12, pp. 1-4, retrieved Dec. 7, 2013.

Coiffier, B., Rituximab therapy in malignant lymphoma, Oncogene, 26: 3603-3613 (2007).

Dees, C.E. et al., Phase 1 study of the investigational drug MLN8237, an oral Aurora A kinase inhibitor, in patients with solid tumors, American Society of Clinical Oncology, powerpoint, 17 pages, (2010).

Dees, E.C. et al, Phase I study of aurora A kinase inhibitor MLN8237 in advanced solid tumors: safety, pharmacokinetics, pharmacodynamics, and bioavailability of two oral formulations, Clin. Cancer Res., 18(17):4775-84 (2012).

Dees, E.C., Phase I Evaluation of MLN8237, a Novel Aurora Kinase Inhibitor, Presentation at Chemotherapy Foundation Symposium XXVI, Nov. 4-8, pp. 1-20 (2008).

Ditchfield, C. et al., Aurora B couples chromosome alignment with anaphase by targeting BubR1, Mad2, and Cenp-E to kinetochores, The Journal of Cell Biology, 161(2):267-280 (2003).

Ecsedy, J. et al, Pharmacokinetics (PK), pharmacodynamics (PD) and exposure-PD relationships of the investigational drug MLN8237, an aurora A kinase inhibitor in patients with advanced solid tumors, Clinical Pharmacology & Therapeutics, 89 (Suppl. 1) S67 (2011).

Faure, A. et al., Process Control and Scale-up of Pharmaceutical Wet Granulation Processes: A Review, European Journal of Pharmaceutics and Biopharmaceutics, 52(3):269-277 (2001).

Friedberg, J. W. et al, Phase II Study of Alisertib, a Selective Aurora A Kinase Inhibitor, in Relapsed and Refractory Aggressive B- and T-Cell Non-Hodgkin Lymphomas, J. Clin. Oncol., 32(1): 44-50 (2014).

Görgün, G. et al., A Novel Aurora A Kinase Inhibitor MLN8237 Induces Cytotoxicity and Cell Cycle Arrest in Multiple Myeloma, The American Society of Hematology, 3830:1-2 (2009).

Görgün, G. et al., A novel Aurora-A kinase inhibitor MLN8237 induces cytotoxicity and cell-cycle arrest in multiple myeloma, Lymphoid Neoplasia: Blood, 115(25):5202-5213 (2010).

Harrington, E.A. et al., VX-680, a potent and selective small-molecular inhibitor of the Aurora kinases, suppresses tumor growth in vivo, Nature Medicine, 10(3):262-267 (2004).

Hauf, S. et al., The small molecule Hesperadin reveals a role for Aurora B in correcting kinetochore-microtubule attachment and in maintaining the spindle assembly checkpoint, The Journal of Cell Biology, 161(2):281-294 (2003).

Huck, J.J. et al., Antitumor Activity of the Aurora A Inhibitor MLN8237 Combination with Docetaxel in Xenograft Models of Breast and Prostate Cancer, American Association for Cancer Research, 1 (2009).

Infante, J. et al. Phase I study of the safety, pharmacokinetics (PK), and pharmacodynamics (PD) of MLN8237, a selective Aurora A kinase inhibitor, in the United States, Eur. J. Cancer, 6(12):90-91 (Suppl) (2008).

International Search Report for PCT/US2009/006560, 4 pages (dated Mar. 1, 2010), Combination of Aurora Kinase Inhibitors and Anti-CD20 Antibodies, Manfredi, M., Millennium Pharmaceuticals, Inc., filed Dec. 15, 2009.

International Search Report for PCT/US2010/001434, 4 pages (dated Jul. 30, 2010), Solid Pharmaceutical Compositions and Processes for Their Production, Mittal, B., Millennium Pharmaceuticals, Inc., filed May 14, 2010.

International Search Report for PCT/US2010/002109, 4 pages (dated Oct. 7, 2010). Pharmaceutical Compositions for the Treatment of Cancer and Other Diseases or Disorders, Ramanan, V. et al., Millennium Pharmaceuticals, Inc., filed Jul. 28, 2010.

International Search Report for PCT/US2011/24883, 2 pages (dated Apr. 11, 2011), Crystalline Forms of Sodium 4-{[9-Chloro-7-(2-FLUORO-6—Methoxyphenyl)-5H—Pyrimido[5,4-D][2]Benzazepin-2YL]AMINO}-2-Methoxybenzoate, Armitage, I., et al., Millennium Pharmaceuticals, Inc., filed Feb. 15, 2011.

Kim, W.S. et al., Phase I Study of MLN9237 (Alisertib) in Adult East Asian Patients (pts) with Advanced Solid Tumors or Lymphomas, Annals of Oncology 24 (Supplement 9): ix31-ix65(2013).

Kollareddy, M. et al., Aurora kinase inhibitors: Progress towards the clinic, Springer: Invest New Drugs, 30:2411-2432 (2012).

Mallick, Should Rituximab Be Used in Elderly Patients With Diffuse Large B-Cell Lymphoma, About.com Leukemia & Lymphoma, Jan. 28, 2007, p. 1, http://lymphoma.about.com/od/treatment/f/rituximabolder.htm, retrieved Jun. 21, 2014.

Matulonis, U.A. et al., Phase II study of MLN8237 (alisertib), an investigational Aurora A kinase inhibitor, in patients with platinum-resistant or -refractory epithelial ovarian, fallopian tube, or primary peritoneal carcinoma. Gynecol Oncol.,127(1):63-9 (2012).

Melichar, B. et al., Phase 1/2 study of investigational Aurora A Kinase inhibitor MLN8237 (alisertib): Updated phase 2 results in patients with small lung cancer (SCLC), non-Sclc (NSCLC), breast cancer (BrC), head and neck squamous cell carcinoma (HNSCC), and gastroesophageal cancer (GE), American Society of Clinical Oncology, abstract and poster, 4 pages, (2013).

Meraldi, P. et al., Aurora-A overexpression reveals tetraploidization as a major route to centrosome amplification in p53$^{-/-}$cells, the European Molecular Biology Organization Journal, 21(4):483-492 (2002).

Mossé, Y. P. et al, Pediatric Phase I Trial and Pharmacokinetic Study of MLN8237, an Investigational Oral Selective Small-Molecule Inhibitor of Aurora Kinase A: A Children's Oncology Group Phase I Consortium Study, Clinical Cancer Res., 18(21): 6058-6064 (2012).

Nawrocki, S.T. et al., The Aurora Kinase Inhibitor MLN8237 has Potent Anticancer Activity in CML and Ph+ All Models and Significantly Increases the Efficacy of Nilotinib, Blood, 112:1-2 (2008).

Padmanabhan, S. et al, Phase I Study of an Investigational Aurora A Kinase Inhibitor MLN8237 in Patients with Advanced Hematologic Malignancies, Blood, ASH Annual Meeting Abstracts, 116(21): Abstract 2799, 1154 (2010).

Sausville, E.A., Aurora kinases dawn as cancer drug targets, Nature Medicine, 10(3):234-235 (2004).

Sells, T et al. "MLN8237: an Orally Active Small Molecule Inhibitor of Aurora A Kinase in Phase I Clinical Trials" Poster presentation at AACR Annual Meeting; Apr. 12-16, 2008.

Solowey, W.E. et al., Peripheral-Acting Benzodiazepines Inhibit the Growth of Human Melanoma Cells and Potentiate the Antiproliferative Activity of Recombinant Human Interferons, the Journal of Interferon Research, 10(3):269-280 (1990).

Tabernero, C.J. et al., MLN8237, an oral selective Aurora A kinase inhibitor: initial results of dose-finding pharmacokinetic-pharmacodynamic phase I study, Eur. J. Cancer, 6:(92 Suppl) (2008).

Trybulski, E. et al., 2-Benzazepines. 5.1'2 Synthesis of Pyrimido[5,4-d][2]benzazepines and Their Evaluation as Anxiolytic Agents, Journal of Medicinal Chemistry, 26(11):1589-1596 (1983).

(56) References Cited

OTHER PUBLICATIONS

Vankayalapati, H. et al., Targeting Aurora2 Kinase in Oncogenesis: A Structural Bioinformatics Approach to Target Validation and Rational Drug Design, Molecular Cancer Therapeutics, 2:283-294 (2003).

Wang, J.K.T. et al., Benzodiazepines that bind at peripheral sites inhibit cell proliferation, Proceedings of the National Academy of Sciences, 81:753-756 (1984).

Written Opinion for PCT/US2009/006560, 4 pages (dated Mar. 1, 2010), Combination of Aurora Kinase Inhibitors and Anti-CD20 Antibodies, Manfredi, M., Millennium Pharmaceuticals, Inc., filed Dec. 15, 2009.

Written Opinion for PCT/US2010/001434, 5 pages (dated Jul. 30, 2010), Solid Pharmaceutical Compositions and Processes for Their Production, Mittal, B., Millennium Pharmaceuticals, Inc., filed May 14, 2010.

Written Opinion for PCT/US2010/002109, 5 pages (dated Oct. 7, 2010), Pharmaceutical Compositions for the Treatment of Cancer and Other Diseases or Disorders, Ramanan, V. et al., Millennium Pharmaceuticals, Inc., filed Jul. 28, 2010.

Written Opinion for PCT/US2011/24883, 3 pages (dated Apr. 11, 2011), Crystalline Forms of Sodium 4-{[9-Chloro-7-(2-Fluoro-6—Methoxyphenyl)-5H-Pyrimido[5,4-D][2]Benzazepin-2YL]AMINO}-2-Methoxybenzoate, Armitage, I., et al., Millennium Pharmaceuticals, Inc., filed Feb. 15, 2011.

Xia, W. et al., Tumor selective G2/M cell cycle arrest and apoptosis of epithelial and hematological malignancies by BBL22, a benzazepine, Proceedings of the National Academy of Sciences, 97(13):7494-7499 (2000).

Yakushijin, Y. et al., The Expression of the Aurora-A Gene and Its Significance with Tumorgenesis in Non-Hodgkin's Lymphoma, Leukemia & Lymphoma, 45(9): 1741-1746 (2004).

Zhou, H. et al., Tumor amplified kinase STK15/BTAK induces centrosome amplification, aneuploidy and transformation, Nature Genetics, 20:189-193 (1998).

Cancer Prevention Overview, National Cancer Institute, 2 pages, (Last modified Aug. 31, 2009). [Retrieved Apr. 9, 2010]. Retrieved from the Internet<http://www.cancer.gov/cancertopics/pdq/prevention/overview/patient>.

Cervantes, A. et al., Pharmacokinetic (PK) and pharmacodynamic (PD) results from 2 phase 1 studies of the investigational selective Aurora A kinase (AAK) inhibitor MLN8237: Exposure-dependent AAK inhibition in human tumors, Presented at the Annual Meeting of the American Society of Clinical Oncology, Chicago, IL, USA, Jun. 6, 2010, poster, (2010).

Cervantes, A. et al., Phase 1 Pharmacokinetic and Pharmacodynamic Study of MLN8237, a Novel, Selective Aurora A Kinase Inhibitor, in Patients with Advanced Solid Tumors, American Society of Clinical Oncology, Presented at the 45th Annual Meeting of the American Society of Clinical Oncology May 30, 2009, Orlando, FL, USA, abstract and poster, 6 pages, (2009).

Dees, E.G. et al, Phase I evaluation of MLN 8237, a novel Aurora A kinase inhibitor, Current Treatment Options in Oncology, 9:116-117 (2008).

Development Pipeline Presentations: Abstract Compendium, American Society of Clinical Oncology, Presented at the 49th Annual Meeting of the American Society of Clinical Oncology in Chicago, IL, USA, May 31-Jun. 4, 2013, 18 pages, (2013).

Falchook, G.S. et al., Food effect study of the investigational Aurora A kinase (AAK) inhibitor MLN8237 (alisertib) in patients with advanced solid tumors, Presented at the European Society for Medical Oncology (ESMO), Annual Congress, Sep. 30, 2012, Vienna, Austria, poster, (2012).

Friedberg, J.W. et al., Multicenter Phase 2 Trial of alisertib (MLN8237), an Investigational Inhibitor of Aurora A Kinase, in Patients with Aggressive B-cell and T-cell NHL, American Society of Clinical Oncology, Presented at the 2011 American Society of Hematology Annual Meeting and Exposition, Dec. 10-13, 2011, San Diego, CA, USA, power point, 29 pages (2011).

Goldberg, S.L. et al., Phase 2 study of MLN8237, an investigational Aurora A Kinase inhibitor in patients with acute myelogenous leukemia or myelodysplastic syndromes, the American Society of Hematology, Presented at the 52nd ASH Annual Meeting, Dec. 4-7, 2010, Orlando, FL, USA Poster, (2010).

Harkevich, D.A. Farmakologija s obshhej recepturoj,—Izd. 2-e, M.—Medicinskoe informacionnoe agenstvo, 2003,—s. 4 (book chapter in Russian). [English translation].

Huck, J. et al., Anti-Tumor Activity of the Aurora a Inhibitor MLN8237 in Diffuse Large B-Cell Lymphoma Preclinical Models, Blood, 112(11):Abstract 1592 (2008), [Retrieved Aug. 16, 2018]. Retrieved from the Internet: <http://www.bloodjournal.org/content/112/11/1592>.

Infante, J. et al. Phase I Study of the Safety, Pharmacokinetics, and Pharmacodynamics of MLN8237, a Selective Aurora A Kinase Inhibitor, in the United States (Study 14001), Presented at the EORTC-NCI-AACR Symposium on Molecular Targets and Cancer Therapeutics, Oct. 21-24, 2008, Geneva, Switzerland, poster (2008).

Kelly, K.R. et al., Results from a phase 1 multicenter trial of alisertib (MLN8237)—an investigational Aurora A kinase inhibitor—in patients with advanced hematologic malignancies, Presented at the 53rd ASH Annual Meeting and Exposition, Dec. 10-13, 2011, San Diego, CA, USA, poster, (2011).

Lee, P., et al. Phase 1/2 study of the investigational Aurora A Kinase (AAK) inhibitor MLN8237 (alisertib) in patients (pts) with non-small cell lung cancer (NSCLC), small cell lung cancer (SCLC), breast cancer (BrC), head/neck cancer (H&N), and gastroesophageal (GE) adenocarcinoma: Preliminary phase 2 results, Presented at ASCO 48th Annual Meeting, Jun. 2, 2012, Chicago, IL, USA, Abstract 3010 (2012).

Mahadevan, D. et al., Clinical and Laboratory Evaluation of MLN8237, and Investigational Aurora A Kinase (AAK) Inhibitor, for Treatment of Aggressive Non-Hodgkin's Lymphoma, Presented a the Third Annual T-cell Lymphoma Forum, Jan. 27-29, 2011, San Francisco, CA, USA, 1 page (2011).

Mahadevan, D. et al., Targeting Aurora Kinase in Aggressive B-Cell Non-Hodgkin's Lymphomas, the American Society of Hematology, 284:1-2 (2009), [Retrieved JUn. 29, 2012]. Retrieved from the Internet: <https://ash.confex/com/ash/2009/webprogram/Paper20630.html>.

Matulonis, U.A. et al., Single-agent activity and safety of the investigational Aurora A kinase inhibitor MLN8237 in patients with platinum-treated epithelial ovarian, fallopian tube, or primary peritoneal carcinoma, American Society of Clinical Oncology, Presented at the 35th ESMO Congress, Oct. 9, 2010, Milan, Italy, Poster, (2010).

Melichar, B. et al., MLN8237 (alisertib), an investigational Aurora A kinase inhibitor, in patients with non-small cell lung cancer, small cell lung cancer, breast cancer, head and neck squamous cell carcinoma, and gastroesophageal cancer: Emerging phase 2 results, American Society of Clinical Oncology, Presented at the European Society for Medical Oncology (ESMO) Annual Congress, Oct. 1, 2012, Vienna, Austria, Poster (2012).

Mosse, Y.P. et al., Pediatric Phase 1 Trial and Pharmacokinetic Study of MLN8237, an Oral Selective Small Molecule Inhibitor of Aurora A Kinase: A Children's Oncology Group Phase 1 Consortium Study, American Society of Clinical Oncology, presented at ASCO, Jun. 6, 2010, Chicago, IL, USA poster, (2010).

O'Connor, O.A. et al., Phase 3 Study of investigational MLN8237 vs. investigator's choice in patients with relapsed/refractory peripheral t-cell lymphoma, American Society of Clinical Oncology, Presented at the 2012 ASCO Annual Meeting Proceedings, Jun. 4, 2012, Chicago, IL, USA, Abstract TPSB110 and Poster, 7 pages (2012).

Padmanabhan, S. et al., Phase I Study of an investigational Aurora A Kinase inhibitor MLN8237 in patients with advanced hematologic malignancies, American Society of Clinical Oncology, Presented at the 52nd ASH Annual Meeting, Dec. 4-7, 2010, Orlando, FL, USA, Poster (2010).

Reagan-Shaw, S. et al, Dose translation from animals to human studies revisited, FASEB J., 22: 659-661 (2007).

Sharma, S. et al., Phase 1 dose-escalation study of the investigational Aurora A Kinase Inhibitor MLN8237 as an enteric-coated

(56) References Cited

OTHER PUBLICATIONS tablet formulation in patients with non-hematologic malignancies, American Society of Clinical Oncology, Presented at the Annual Meeting of the American Society of Clinical Oncology, Jun. 6, 2011, Chicago, IL, USA, Poster (2011).

Tabernero, J et al. MLN8237, an Oral Selective Aurora A Kinase Inhibitor: Initial Results of Dose-Finding Pharmacokinetic-Pharmacodynamic Phase I Study (Study 14002 [Spain]), Presented at EORTC-NCI-AACR Symposium on Molecular Targets and Cancer Therapeutics, Oct. 21-24, 2008, Geneva, Switzerland, Poster (2008).

Venkatakrishnan, K. et al., Clinical pharmacologic considerations for the phase 2/3 dose/regimen of the investigational Aurora A kinase inhibitor MLN8237 (alisertib): Pharmacokinetics, pharmacodynamics, and exposure-safety relationships, American Society of Clinical Oncology, Presented at the 48th Annual Meeting of the American Society of Clinical Oncology, Jun. 4, 2012, Chicago, IL, USA, Poster of Abstract 2597 (2012).

Zhang, M. et al., Aurora A Kinase Inhibitor MLN8237 in Combination with Docetaxel Induces Synergistic Antitumor Activity in Triple-Negative Breast Cancer Xenograft Models, Presented at the 22nd EORTC—NCI-AACR Symposium, Nov. 15-19, 2010, Berlin, Germany, poster, (2010).

Zhou, X. et al., Pharmacokinetics, Pharmacodynamics and Exposure-Pharmacodynamic Relationships of Investigational Drug MLN8237, and Aurora A Kinase Inhibitor in Patients with Advanced Solid Tumors, Millennium Pharmaceuticals Inc., presented at the American Society for Clinical Pharmacology and Therapeutics Annual Meeting, Mar. 5, 2011, Dallas, TX, USA, 11 pages (2011).

A Phase 1 Dose Escalation Study of MLN8237, an Aurora A Kinase Inhibitor, in Adult Patients With Nonhematological Malignancies, Followed by Phase 2 of MLN8237 in Lung, Breast, Head and Neck, or Gastroesophageal Malignancies, <http://clinicaltrials.gov/archive/NCT01045421/2012_01_30> (2012).

\* cited by examiner

COMBINATION OF AURORA KINASE INHIBITORS AND ANTI-CD20 ANTIBODIES

RELATED APPLICATIONS

The present application claims the benefit of U.S. Provisional Application Ser. No. 61/203,509, filed Dec. 22, 2008, the contents of which are incorporated herein by reference.

FIELD OF THE INVENTION

This invention relates to methods for the treatment of hematological malignancies. In particular, the invention provides methods for treatment of hematological malignancies by administering Aurora kinase inhibitors in combination with anti-CD20 antibodies.

BACKGROUND OF THE INVENTION

According to the American Cancer Society, an estimated 1.4 million Americans were newly-diagnosed with cancer in 2004 and about 560,000 victims died from the disease. While medical advance have improved cancer survival rates, there is a continuing need for new and more effective treatment.

Cancer is characterized by uncontrolled cell reproduction. Mitosis is a stage in the cell cycle during which a series of complex events ensure the fidelity of chromosome separation into two daughter cells. Several current cancer therapies, including the taxanes and vinca alkaloids, act to inhibit the mitotic machinery. Mitotic progression is largely regulated by proteolysis and by phosphorylation events that are mediated by mitotic kinases. Aurora kinase family members (e.g., Aurora A, Aurora B, Aurora C) regulate mitotic progression through modulation of centrosome separation, spindle dynamics, spindle assembly checkpoint, chromosome alignment/segregation, and cytokinesis (Dutertre et al., Oncogene, 21: 6175 (2002); Berdnik et al., Curr. Biol., 12: 640 (2002)). Overexpression and/or amplification of Aurora kinases have been linked to oncogenesis in several tumor types including those of colon and breast (Warner et al., Mol. Cancer Ther., 2: 589 (2003); Bischoff et al., EMBO, 17: 3062 (1998); Sen et al., Cancer Res., 94: 1320 (2002)). Moreover, Aurora kinase inhibition in tumor cells results in mitotic arrest and apoptosis, suggesting that these kinases are important targets for cancer therapy (Manfredi et al., PNAS., 104: 4106 (2007); Ditchfield, J. Cell Biol., 161: 267 (2003); Harrington et al., Nature Med., 1 (2004)). Given the central role of mitosis in the progression of virtually all malignancies, inhibitors of the Aurora kinases are expected to have application across a broad range of human tumors.

CD20 (also known as Bp35) is a B-lymphocyte-restricted differentiation antigen that is expressed during early pre-B-cell development and remains until plasma cell differentiation. CD20 is a useful target for B-cell lymphomas as this antigen is expressed at very high densities on the surface of malignant B-cells, i.e., B-cells wherein unabated proliferation can lead to B-cell lymphomas. The Food and Drug Administration has approved the therapeutic use of an anti-CD20 antibody, rituximab (RITUXAN®), for use in relapsed and previously treated low-grade non-Hodgkin's lymphoma (NHL). Rituximab acts by binding to the CD20 antigen on B cells which results in the lysis of the B cell by a mechanism thought to involve complement-dependent cytotoxicity (CDC) and antibody-dependent cell mediated cytotoxicity (ADCC).

However, while anti-CD20 antibodies and, in particular, rituximab, have been reported to be effective for treatment of B-cell lymphomas, such as non-Hodgkin's lymphoma, the treated patients are often subject to disease relapse. Therefore, it would be beneficial if more effective treatment regimens could be developed. Combined treatment regimens could be helpful for patients suffering from B cell related tumors or other hematological malignancies, and might potentially even decrease the rate of relapse or overcome the resistance to a particular anticancer agent sometime seen in these patients. Additionally, combinations of anticancer agents may have additive, or even synergistic, therapeutic effects.

There is thus a need for new cancer treatment regimens, including combination therapies.

DESCRIPTION OF THE INVENTION

The present invention provides new combination therapies for the treatment of hematological malignancies. In particular, the present invention provides a method to treat a patient suffering from a hematological malignancy comprising administering to said patient a therapeutically effective amount of a Aurora kinase inhibitor simultaneously with or consecutively with (e.g., before or after) an anti-CD20 antibody.

Terms used herein shall be accorded the following defined meanings, unless otherwise indicated.

As used herein, the term "Aurora kinase" refers to any one of a family of related serine/threonine kinases involved in mitotic progression. A variety of cellular proteins that play a role in cell division are substrates for phosphorylation by Aurora kinase enzymes, including, without limitation, histone H3, p53, CENP-A, myosin II regulatory light chain, protein phosphatase-1, TPX-2, INCENP, survivin, topoisomerase II alpha, vimentin, MBD-3, MgcRacGAP, desmin, Ajuba, XlEg5 (in *Xenopus*), Ndc10p (in budding yeast), and D-TACC (in *Drosophila*). Aurora kinase enzymes also are themselves substrates for autophosphorylation, e.g., at Thr288. Unless otherwise indicated by context, the term "Aurora kinase" is meant to refer to any Aurora kinase protein from any species, including, without limitation, Aurora A, Aurora B, and Aurora C, preferably Aurora A or B. Preferably, the Aurora kinase is a human Aurora kinase.

The term "Aurora kinase inhibitor" or "inhibitor of Aurora kinase" is used to signify a compound which is capable of interacting with an Aurora kinase and inhibiting its enzymatic activity. Inhibiting Aurora kinase enzymatic activity means reducing the ability of an Aurora kinase to phosphorylate a substrate peptide or protein. In various embodiments, such reduction of Aurora kinase activity is at least about 50%, at least about 75%, at least about 90%, at least about 95%, or at least about 99%. In various embodiments, the concentration of Aurora kinase inhibitor required to reduce an Aurora kinase enzymatic activity is less than about 1 µM, less than about 500 nM, less than about 100 nM, or less than about 50 nM.

In some embodiments, such inhibition is selective, i.e., the Aurora kinase inhibitor reduces the ability of an Aurora kinase to phosphorylate a substrate peptide or protein at a concentration that is lower than the concentration of the inhibitor that is required to produce another, unrelated biological effect, e.g., reduction of the enzymatic activity of a different kinase. In some embodiments, the Aurora kinase inhibitor also reduces the enzymatic activity of another kinase, preferably one that is implicated in cancer.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

As used herein, the term "comprises" means "includes, but is not limited to."

A "CD20" antigen is a 35 kDa, non-glycosylated phosphoprotein found on the surface of greater than 90% of B cells from peripheral blood or lymphoid organs. CD20 is expressed during early pre-B cell development and remains until plasma cell differentiation. CD20 is present on both normal B cells as well as malignant B cells. Other names for CD20 in the literature include "B-lymphocyte-restricted antigen" and "Bp35".

The CD20 antigen is described in, e.g., Clark et al. PNAS (USA) 82:1766 (1985).

The term "antibody" herein is used in the broadest sense and specifically covers intact monoclonal antibodies, polyclonal antibodies, humanized antibodies, human antibodies, chimeric antibodies, multispecific antibodies (e.g., bispecific antibodies) formed from at least two intact antibodies, and antibody fragments, so long as they exhibit the desired biological activity. Antibodies may be produced by one of skill in the art using conventional methods.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations, which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352:624-628 (1991) and Marks et al, J. MoL Biol., 222:581-597 (1991), for example. The monoclonal antibodies herein specifically include but are not limited to "chimeric" or "humanized" forms.

The term "aliphatic" or "aliphatic group", as used herein, means a substituted or unsubstituted straight-chain, branched or cyclic $C_{1-12}$ hydrocarbon, which is completely saturated or which contains one or more units of unsaturation, but which is not aromatic. For example, suitable aliphatic groups include substituted or unsubstituted linear, branched or cyclic alkyl, alkenyl, alkynyl groups and hybrids thereof, such as (cycloalkyl)alkyl, (cycloalkenyl) alkyl or (cycloalkyl)alkenyl.

The terms "alkyl", "alkenyl", and "alkynyl", used alone or as part of a larger moiety, refer to a straight and branched chain aliphatic group having from 1 to 12 carbon atoms. For purposes of the present invention, the term "alkyl" will be used when the carbon atom attaching the aliphatic group to the rest of the molecule is a saturated carbon atom. However, an alkyl group may include unsaturation at other carbon atoms. Thus, alkyl groups include, without limitation, methyl, ethyl, propyl, allyl, propargyl, butyl, pentyl, and hexyl.

For purposes of the present invention, the term "alkenyl" will be used when the carbon atom attaching the aliphatic group to the rest of the molecule forms part of a carbon-carbon double bond. Alkenyl groups include, without limitation, vinyl, 1-propenyl, 1-butenyl, 1-pentenyl, and 1-hexenyl.

For purposes of the present invention, the term "alkynyl" will be used when the carbon atom attaching the aliphatic group to the rest of the molecule forms part of a carbon-carbon triple bond. Alkynyl groups include, without limitation, ethynyl, 1-propynyl, 1-butynyl, 1-pentynyl, and 1-hexynyl.

The term "cycloaliphatic", used alone or as part of a larger moiety, refers to a saturated or partially unsaturated cyclic aliphatic ring system having from 3 to about 14 members, wherein the aliphatic ring system is optionally substituted. In some embodiments, the cycloaliphatic is a monocyclic hydrocarbon having 3-8 or 3-6 ring carbon atoms. Nonlimiting examples include cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloaliphatic is a bridged or fused bicyclic hydrocarbon having 6-12, 6-10, or 6-8 ring carbon atoms, wherein any individual ring in the bicyclic ring system has 3-8 members.

In some embodiments, two adjacent substituents on the cycloaliphatic ring, taken together with the intervening ring atoms, form an optionally substituted fused 5- to 6-membered aromatic or 3- to 8-membered non-aromatic ring having 0-3 ring heteroatoms selected from the group consisting of O, N, and S. Thus, the term "cycloaliphatic" includes aliphatic rings that are fused to one or more aryl, heteroaryl, or heterocyclyl rings. Nonlimiting examples include indanyl, 5,6,7,8-tetrahydroquinoxalinyl, decahydronaphthyl, or tetrahydronaphthyl, where the radical or point of attachment is on the aliphatic ring. The term "cycloaliphatic" may be used interchangeably with the terms "carbocycle", "carbocyclyl", "carbocyclo", or "carbocyclic".

The terms "aryl" and "ar-", used alone or as part of a larger moiety, e.g., "aralkyl", "aralkoxy", or "aryloxyalkyl", refer to a $C_6$ to $C_{14}$ aromatic hydrocarbon, comprising one to three rings, each of which is optionally substituted. Preferably, the aryl group is a $C_{6-10}$ aryl group. Aryl groups include, without limitation, phenyl, naphthyl, and anthracenyl. In some embodiments, two adjacent substituents on the aryl ring, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the term "aryl", as used herein, includes groups in which an aromatic ring is fused to one or more heteroaryl, cycloaliphatic, or heterocyclyl rings, where the radical or point of attachment is on the aromatic ring. Nonlimiting examples of such fused ring systems include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl. An aryl group may be mono-, bi-, tri-, or polycyclic, preferably mono-, bi-, or tricyclic, more preferably mono- or bicyclic. The term "aryl" may be used interchangeably with the terms "aryl group", "aryl moiety", and "aryl ring".

An "aralkyl" or "arylalkyl" group comprises an aryl group covalently attached to art alkyl group, either of which independently is optionally substituted. Preferably, the aralkyl group is $C_{6-10}$ aryl$(C_{1-6})$alkyl, $C_{6-10}$ aryl$(C_{1-4})$alkyl, or $C_{6-10}$ aryl$(C_{1-3})$alkyl, including, without limitation, benzyl, phenethyl, and naphthylmethyl.

The terms "heteroaryl" and "heteroar-", used alone or as part of a larger moiety, e.g., heteroaralkyl, or "heteroaralkoxy", refer to groups having 5 to 14 ring atoms, preferably 5, 6, 9, or 10 ring atoms; having 6, 10, or 14 π electrons shared in a cyclic array; and having, in addition to carbon atoms, from one to four heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, two adjacent substituents on the heteroaryl, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono-, bi-, tri-, or polycyclic, preferably mono-, bi-, or tricyclic, more preferably mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 3- to 7-membered monocyclic, or to a fused 7- to 10-membered or bridged 6- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a heterocyclyl ring having 1-3 heteroatoms selected from oxygen, sulfur or nitrogen, the nitrogen may be N (as in 3,4-dihydro-2H-pyrrolyl), NH (as in pyrrolidinyl) or $^+$NR (as in N-substituted pyrrolidinyl). A heterocyclic ring can be attached to its pendant group at any heteroatom or carbon atom that results in a stable structure, and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl.

In some embodiments, two adjacent substituents on a heterocyclic ring, taken together with the intervening ring atoms, for an optionally substituted fused 5- to 6-membered aromatic or 3- to 8-membered non-aromatic ring having 0-3 ring heteroatoms selected from the group consisting of O, N, and S. Thus, the terms "heterocycle", "heterocyclyl", "heterocyclyl ring", "heterocyclic group", "heterocyclic moiety", and "heterocyclic radical", are used interchangeably herein, and include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms. The term "partially unsaturated" is intended to encompass rings having multiple sites of unsaturation, but is not intended to include aryl or heteroaryl moieties, as herein defined.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

The term "substituted", as used herein, means that a hydrogen radical of the designated moiety is replaced with the radical of a specified substituent, provided that the substitution results in a stable or chemically feasible compound. The phrase "one or more substituents", as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different.

An aryl (including the aryl moiety in aralkyl, aralkoxy, aryloxyalkyl and the like) or heteroaryl (including the heteroaryl moiety in heteroaralkyl and heteroaralkoxy and the like) group may contain one or more substituents. Examples of suitable substituents on the unsaturated carbon atom of an aryl or heteroaryl group include -halo, —$NO_2$, —CN, —R*, —C(R*)=C(R*)$_2$, —C≡C—R*, —OR*, —SR°, —S(O)R°, —SO$_2$R$^o$, —SO$_3$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(O)N(R$^+$)C(=NR$^+$)—N(R$^+$)$_2$, —N(R$^+$)C(=NR$^+$)—N(R$^+$)—C(O)R*, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R$^o$, —NR$^+$SO$_2$N(R$^+$)$_2$, —P(O)(R*)$_2$, —P(O)(OR*)$_2$, —O—P(O)—OR*, and —P(O)(NR$^+$)—N(R$^+$)$_2$; or two adjacent substituents, taken together with their intervening atoms, form a 5-6 membered unsaturated or partially unsaturated ring having 0-3 ring atoms selected from the group consisting of N, O, and S.

An aryl (including the aryl moiety in aralkyl, aralkoxy, aryloxyalkyl and the like) or heteroaryl (including the heteroaryl moiety in heteroaralkyl and heteroaralkoxy and the like) group may contain one or more substituents. Examples of suitable substituents on the unsaturated carbon atom of an aryl or heteroaryl group include -halo, —NO$_2$, —CN, —R*, —C(R*)=C(R*)$_2$, —C≡C—R*, —OR*, —SR$^o$, —S(O)R$^o$, —SO$_2$R$^o$, —SO$_3$R$^o$, —SO$_2$N(R$^+$)$_2$, —N(R$^+$)$_2$, —NR$^+$C(O)R*, —NR$^+$C(O)N(R$^+$)$_2$, —NR$^+$CO$_2$R$^o$, —O—CO$_2$R*, —OC(O)N(R$^+$)$_2$, —O—C(O)R*, —CO$_2$R*, —C(O)—C(O)R*, —C(O)R*, —C(O)N(R$^+$)$_2$, —C(O)N(R$^+$)C(=NR$^+$)—N(R$^+$)$_2$, —N(R$^+$)C(=NR$^+$)—N(R$^+$)—C(O)R*, —C(=NR$^+$)—N(R$^+$)$_2$, —C(=NR$^+$)—OR*, —N(R$^+$)—N(R$^+$)$_2$, —N(R$^+$)C(=NR$^+$)—N(R$^+$)$_2$, —NR$^+$SO$_2$R$^o$, —NR$^+$SO$_2$N(R$^+$)$_2$, —P(O)(R*)$_2$, —P(O)(OR*)$_2$, —O—P(O)—OR*, and —P(O)(NR$^+$)—N(R$^+$)$_2$; or two adjacent substituents, taken together with their intervening atoms, form a 5-6 membered unsaturated or partially unsaturated ring having 0-3 ring atoms selected from the group consisting of N, O, and S.

Each R$^+$, independently, is hydrogen or an optionally substituted aliphatic, aryl, heteroaryl, or heterocyclyl group, or two R$^+$ on the same nitrogen atom, taken together with the nitrogen atom, form a 5-8 membered aromatic or non-aromatic ring having, in addition to the nitrogen atom, 0-2 ring heteroatoms selected from N, O, and S. Each R* independently is hydrogen or an optionally substituted aliphatic, aryl, heteroaryl, or heterocyclyl group. Each R$^o$ is an optionally substituted aliphatic or aryl group.

An aliphatic group or a non-aromatic heterocyclic ring may be substituted with one or more substituents. Examples of suitable substituents on the saturated carbon of an aliphatic group or of a non-aromatic heterocyclic ring include, without limitation, those listed above for the unsaturated carbon of an aryl or heteroaryl group and the following: =O, =S, =C(R*)$_2$, =N—N(R*)$_2$, =N—OR*, =N—NHC(O)R*, =N—NHCO$_2$R$^o$, =N—NHSO$_2$R$^o$, or =N—R*, where each R* and R$^o$ is as defined above.

Suitable substituents on the nitrogen atom of a non-aromatic heterocyclic ring include —R*, —N(R*)$_2$, —C(O)R*, —CO$_2$R*, —C(O)—C(O)R* —C(O)CH$_2$C(O)R*, —SO$_2$R*, —SO$_2$N(R*)$_2$, —C(=S)N(R*)$_2$, —C(=NH)—N(R*)$_2$, and —NR*SO$_2$R*; wherein each R* is as defined above.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

It will be apparent to one skilled in the art that certain compounds described herein may exist in tautomeric forms, all such tautomeric forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Any compound capable of inhibiting the enzymatic activity of an Aurora kinase may be used in the methods of the instant invention. In particular, Aurora kinase inhibitors include the compounds described herein, as well as compounds disclosed in, for example, WO 05/111039, US2005/0256102, US2007/0185087, WO 08/021038, US2008/0045501, WO 08/063525, US2008/0167292, WO 07/113212, EP1644376, US2005/0032839, WO 05/005427, WO 06/070192, WO 06/070198, WO 06/070202, WO 06/070195, WO 06/003440, WO 05/002576, WO 05/002552, WO 04/071507, WO 04/058781, WO 06/055528, WO 06/055561, WO 05/118544, WO 05/013996, WO 06/036266, US2006/0160874, US2007/0142368, WO 04/043953, WO 07/132220, WO 07/132221, WO 07/132228, WO 04/00833 and WO 07/056164, each of which is hereby incorporated by reference in its entirety. Also suitable for use in the methods of the invention are solvated and hydrated forms of any of these compounds. Also suitable for use in the methods of the invention are pharmaceutically acceptable salts of any of the compounds, and solvated and hydrated forms of such salts. These Aurora kinase inhibitors can be prepared in a number of ways well known to one skilled in the art of organic synthesis, including, but not limited to, the methods of synthesis described in detail in the above references.

In some embodiments, the Aurora kinase inhibitor is a compound represented by formula (I):

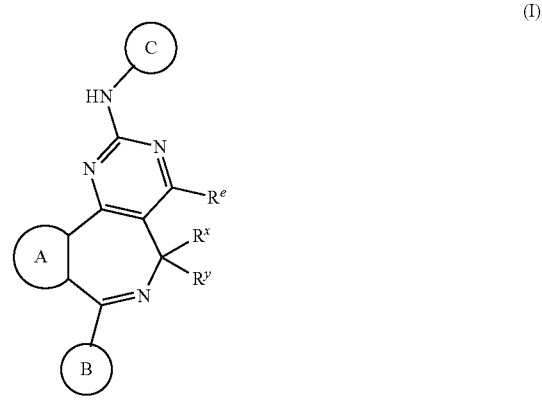

or a pharmaceutically acceptable salt thereof;
wherein:
Ring A is a substituted or unsubstituted 5- or 6-membered aryl, heteroaryl, cycloaliphatic, or heterocyclyl ring;
Ring B is a substituted or unsubstituted aryl, heteroaryl, cycloaliphatic, or heterocyclyl ring;
Ring C is a substituted or unsubstituted aryl, heteroaryl, heterocyclyl, or cycloaliphatic ring;
R$^e$ is hydrogen, —OR$^5$, —N(R$^4$)$_2$, —SR$^5$, or a C$_{1-3}$ aliphatic optionally substituted with R$^3$ or R$^7$;
each of R$^x$ and R$^y$ independently is hydrogen, fluoro, or an optionally substituted C$_{1-6}$ aliphatic; or R$^x$ and R$^y$, taken together with the carbon atom to which they are attached, form an optionally substituted 3- to 6-membered cycloaliphatic ring;

each $R^3$ independently is selected from the group consisting of -halo, —OH, —O($C_{1-3}$ alkyl), —CN, —N($R^4$)$_2$, —C(O)($C_{1-3}$ alkyl), —CO$_2$H, —CO$_2$($C_{1-3}$ alkyl), —C(O)NH$_2$, and —C(O)NH($C_{1-3}$ alkyl);

each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 5- to 6-membered heteroaryl or 4- to 8-membered heterocyclyl ring having, in addition to the nitrogen atom, 0-2 ring heteroatoms selected from N, O, and S;

each $R^5$ independently is hydrogen or an optionally substituted aliphatic, aryl, heteroaryl, or heterocyclyl group; and each $R^7$ independently is an optionally substituted aryl, heterocyclyl, or heteroaryl group.

Ring A is a substituted or unsubstituted 5- or 6-membered aryl, heteroaryl, cycloaliphatic, or heterocyclyl ring. Examples of Ring A include furano, dihydrofurano, thieno, dihydrothieno, cyclopenteno, cyclohexeno, 2H-pyrrolo, pyrrolo, pyrrolino, pyrrolidino, oxazolo, thiazolo, imidazolo, imidazolino, imidazolidino, pyrazolo, pyrazolino, pyrazolidino, isoxazolo, isothiazolo, oxadiazolo, triazolo, thiadiazolo, 2H-pyrano, 4H-pyrano, benzo, pyridino, piperidino, dioxano, morpholino, dithiano, thiomorpholino, pyridazino, pyrimidino, pyrazino, piperazino, and triazino, any of which groups may be substituted or unsubstituted. Preferred values for Ring A include, without limitation, substituted or unsubstituted rings selected from the group consisting of furano-, thieno, pyrrolo, oxazolo, thiazolo, imidazolo, pyrazolo, isoxazolo, isothiazolo, triazolo, benzo, pyridino, pyridazino, pyrimidino, and pyrazino.

Ring A may be substituted or unsubstituted. In some embodiments, each substitutable saturated ring carbon atom in Ring A is unsubstituted or is substituted with =O, =S, =C($R^5$)$_2$, =N—N($R^4$)$_2$, =N—OR$^5$, =N—NHC(O)R$^5$, =N—NHCO$_2$R$^6$, =N—NHSO$_2$R$^6$, =N—R$^5$ or —R$^b$, where $R^b$, $R^4$, $R^5$, and $R^6$ are as defined below. Each substitutable unsaturated ring carbon atom in Ring A is unsubstituted or substituted with —R$^b$. Each substitutable ring nitrogen atom in Ring A is unsubstituted or is substituted with —R$^{9b}$, and one ring nitrogen atom in Ring A optionally is oxidized. Each $R^{9b}$ independently is —C(O)R$^5$, —C(O)N(R$^4$)$_2$, —CO$_2$R$^6$, —SO$_2$R$^6$, —SO$_2$N(R$^4$)$_2$, or a $C_{1-4}$ aliphatic optionally substituted with $R^3$ or $R^7$.

Each $R^b$ independently is $R^{2b}$, an optionally substituted aliphatic, or an optionally substituted aryl, heterocyclyl, or heteroaryl group; or two adjacent $R^b$, taken together with the intervening ring atoms, form an optionally substituted fused 4- to 8-membered aromatic or non-aromatic ring having 0-3 ring heteroatoms selected from the group consisting of O, N, and S.

Each $R^{2b}$ independently is -halo, —NO$_2$, —CN, —C(R$^5$)=C(R$^5$)$_2$, —C(R$^5$)=C(R$^5$)(R$^{10}$), —C≡C—R$^5$, —C≡C—R$^{10}$, —OR$^5$, —SR$^6$, —S(O)R$^6$, —SO$_2$R$^6$, —SO$_2$N(R$^4$)$_2$, —N(R$^4$)$_2$, —NR$^4$C(O)R$^5$, —NR$^4$C(O)N(R$^4$)$_2$, —NR$^4$CO$_2$R$^6$, —O—CO$_2$R$^5$, —OC(O)N(R$^4$)$_2$, —O—C(O)R$^5$, —CO$_2$R$^5$, —C(O)—C(O)R$^5$, —C(O)R$^5$, —C(O)N(R$^4$)$_2$, —C(=NR$^4$)—N(R$^4$)$_2$, —C(=NR$^4$)—OR$^5$, —N(R$^4$)—N(R$^4$)$_2$, N(R$^4$)C(=NR$^4$)—N(R$^4$)$_2$, —N(R$^4$)SO$_2$R$^6$, —N(R$^4$)SO$_2$N(R$^4$)$_2$, —P(O)(R$^5$)$_2$, or —P(O)(OR$^5$)$_2$, where the variables $R^4$, $R^5$, and $R^7$ have the values described above; each $R^6$ independently is an optionally substituted aliphatic or aryl group; and each $R^{10}$ independently is —CO$_2$R$^5$ or —C(O)N(R$^4$)$_2$.

In some embodiments, Ring A is substituted by 0-2 substituents $R^b$. In some embodiments, each $R^b$ independently is $C_{1-3}$ aliphatic or $R^{2b}$, and each $R^{2b}$ independently is selected from the group consisting of -halo, —NO$_2$, —C(R$^5$)=C(R$^5$)$_2$, —C≡C—R$^5$, —OR$^5$, and —N(R$^4$)$_2$. In some embodiments, each $R^b$ independently is selected from the group consisting of -halo, $C_{1-3}$ aliphatic, $C_{1-3}$ fluoroaliphatic, and —OR$^5$, where $R^5$ is hydrogen or $C_{1-3}$ aliphatic. In certain preferred embodiments, Ring A is substituted with 0, 1, or 2 substituents, preferably 0 or 1 substituents, independently selected from the group consisting of chloro, fluoro, bromo, methyl, trifluoromethyl, and methoxy.

In some embodiments, Ring B is a substituted or unsubstituted mono- or bicyclic aryl or heteroaryl ring selected from the group consisting of furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, pyridyl, pyridazinyl, pyrimidinyl, pyrazinyl, triazinyl, indolizinyl, indolyl, isoindolyl, indazolyl, benzo[b]furanyl, benzo[b]thienyl, benzimidazolyl, benzthiazolyl, benzoxazolyl, purinyl, quinolyl, isoquinolyl, cinnolinyl, phthalazinyl, quinazolinyl, quinoxalinyl, naphthyridinyl, and pteridinyl.

Each substitutable saturated ring carbon atom in Ring B is unsubstituted or is substituted with =O, =S, =C(R$^5$)$_2$, =N—N(R$^4$)$_2$, =N—OR$^5$, =N—NHC(O)R$^5$, =N—NHCO$_2$R$^6$, =N—NHSO$_2$R$^6$, =N—R$^5$ or —R$^c$. Each substitutable unsaturated ring carbon atom in Ring B is unsubstituted or substituted with —R$^c$. Each substitutable ring nitrogen atom in Ring B is unsubstituted or is substituted with —R$^{9c}$, and one ring nitrogen atom in Ring B optionally is oxidized. Each $R^{9c}$ independently is —C(O)R$^5$, —C(O)N(R$^4$)$_2$, —CO$_2$R$^6$, —SO$_2$R$^6$, —SO$_2$N(R$^4$)$_2$, or a $C_{1-4}$ aliphatic optionally substituted with $R^3$ or $R^7$. Ring B may be unsubstituted or may be substituted on any one or more of its component rings, wherein the substituents may be the same or different. In some embodiments, Ring B is substituted with 0-2 independently selected $R^c$ and 0-3 independently selected $R^{2c}$ or $C_{1-6}$ aliphatic groups. The variables $R^3$, $R^4$, $R^5$, $R^6$, and $R^7$ are as defined above for Ring A, and $R^c$ and $R^{2c}$ are defined below.

Each $R^c$ independently is $R^{2c}$, an optionally substituted $C_{1-6}$ aliphatic, or an optionally substituted aryl, heteroaryl, or heterocyclyl group.

Each $R^{2c}$ independently is -halo, —NO$_2$, —CN, —C(R$^5$)=C(R$^5$)$_2$, —C(R$^5$)=C(R$^5$)(R$^{10}$), —C≡C—R$^5$, —C≡C—R$^{10}$, —OR$^5$, —SR$^6$, —S(O)R$^6$, —SO$_2$R$^6$, —SO$_2$N(R$^4$)$_2$, —N(R$^4$)$_2$, —NR$^4$C(O)R$^5$, —NR$^4$C(O)N(R$^4$)$_2$, —NR$^4$CO$_2$R$^6$, —O—CO$_2$R$^5$, —OC(O)N(R$^4$)$_2$, —O—C(O)R$^5$, —CO$_2$R$^5$, —C(O)—C(O)R$^5$, —C(O)R$^5$, —C(O)N(R$^4$)$_2$, —C(=NR$^4$)—N(R$^4$)$_2$, —C(=NR$^4$)—OR$^5$, —N(R$^4$)—N(R$^4$)$_2$, —N(R$^4$)C(=NR$^4$)—N(R$^4$)$_2$, —N(R$^4$)SO$_2$R$^6$, —N(R$^4$)SO$_2$N(R$^4$)$_2$, —P(O)(R$^5$)$_2$, or —P(O)(OR$^5$)$_2$.

In some embodiments, Ring B is a monocyclic 5- or 6-membered aryl or heteroaryl ring, substituted with 0-2 independently selected $R^c$ and 0-2 independently selected $R^{2c}$ or $C_{1-6}$ aliphatic groups. In certain such embodiments, Ring B is a substituted or unsubstituted phenyl or pyridyl ring.

In some embodiments, Ring B is substituted with 0-2 substituents $R^c$. In some such embodiments, each $R^c$ independently is $C_{1-3}$ aliphatic or $R^{2c}$, and each $R^{2c}$ independently is selected from the group consisting of -halo, —NO$_2$, —C(R$^5$)=C(R$^5$)$_2$, —C≡C—R$^5$, —OR$^5$, and —N(R$^4$)$_2$. In some embodiments, each $R^c$ independently is selected from the group consisting of -halo, $C_{1-3}$ aliphatic, $C_{1-3}$ haloaliphatic, and —OR$^5$, where $R^5$ is hydrogen or $C_{1-3}$ aliphatic. In certain preferred embodiments, Ring B is substituted with 0, 1, or 2 substituents, independently selected from the group consisting of chloro, fluoro, bromo, methyl, trifluoromethyl, and methoxy.

Each substitutable saturated ring carbon atom in Ring C is unsubstituted or is substituted with =O, =S, =C(R$^5$)$_2$, =N—N(R$^4$)$_2$, —N—OR$^5$, =N—NHC(O)R$^5$, =N—NHCO$_2$R$^6$, —N—NHSO$_2$R$^6$, —N—R$^5$ or —R$^d$. Each substitutable unsaturated ring carbon atom in Ring C is unsubstituted or substituted with —R$^d$. Each substitutable ring nitrogen atom in Ring C is unsubstituted or is substituted with —R$^{9d}$, and one ring nitrogen atom in Ring C optionally is oxidized. Each R$^{9d}$ independently is —C(O)R$^5$, —C(O)N(R$^4$)$_2$, —CO$_2$R$^6$, —SO$_2$R$^6$, —SO$_2$N(R$^4$)$_2$, or a C$_{1-4}$ aliphatic optionally substituted with R$^3$ or R$^7$. Ring C may be unsubstituted or may be substituted on any one or more of its component rings, wherein the substituents may be the same or different. In some embodiments, Ring C is substituted with 0-2 independently selected R$^d$ and 0-3 independently selected R$^{2d}$ or C$_{1-6}$ aliphatic groups. The variables R$^3$, R$^4$, R$^5$, R$^6$, and R$^7$ are as described above for Rings A and B. The variables R$^d$ and R$^{2d}$ are described below.

Each R$^d$ independently is R$^{2d}$, an optionally substituted aliphatic, or an optionally substituted aryl, heteroaryl, or heterocyclyl group.

Each R$^{2d}$ independently is -halo, —NO$_2$, —CN, —C(R$^5$)=C(R$^5$)$_2$, —C(R$^5$)=C(R$^5$)$_2$(R$^{10}$), —C≡C—R$^5$, —C≡C—R$^{10}$, —OR$^5$, —SR$^6$, —S(O)R$^6$, —SO$_2$R$^6$, —SO$_2$N(R$^4$)$_2$, —N(R$^4$)$_2$, —NR$^4$C(O)R$^5$, —NR$^4$C(O)N(R$^4$)$_2$, —NR$^4$CO$_2$R$^6$, —O—CO$_2$R$^5$, —OC(O)N(R$^4$)$_2$, —O—C(O)R$^5$, —CO$_2$R$^5$, —C(O)—C(O)R$^5$, —C(O)R$^5$, —C(O)N(R$^4$)$_2$, —C(=NR$^4$)—N(R$^4$)$_2$, —C(=NR$^4$)—OR$^5$, —N(R$^4$)—N(R$^4$)$_2$, —N(R$^4$)C(=NR$^4$)—N(R$^4$)$_2$, —N(R$^4$)SO$_2$R$^6$, —N(R$^4$)SO$_2$N(R$^4$)$_2$, —P(O)(R$^5$)$_2$, or —P(O)(OR$^5$)$_2$. Additionally, R$^{2d}$ can be —SO$_3$R$^5$, —C(O)N(R$^4$)C(=NR$^4$)—N(R$^4$)$_2$ or —N(R$^4$)C(=NR$^4$)—N(R$^4$)—C(O)R$^5$.

In some embodiments, Ring C is a monocyclic 5- or 6-membered aryl or heteroaryl ring, which is substituted with 0-2 independently selected substituents R$^d$ and 0-2 independently selected R$^{2d}$ or C$_{1-6}$ aliphatic groups. In some such embodiments, Ring C is an optionally substituted heteroaryl ring selected from the group consisting of pyridyl, pyrimidinyl, pyrazinyl, pyridazinyl, imidazolyl, pyrazolyl, and oxazolyl. In some other embodiments, Ring C is a substituted or unsubstituted phenyl ring. In some embodiments, Ring C is a monocyclic 5- or 6-membered aryl or heteroaryl ring, which is substituted with 0, 1, or 2 substituents R$^d$, as defined above.

In some other embodiments, Ring C is a monocyclic 5- or 6-membered heterocyclyl or cycloaliphatic ring, which is substituted with 0-2 independently selected substituents R$^d$ and 0-2 independently selected R$^{2d}$ or C$_{1-6}$ aliphatic groups.

In some embodiments, the Aurora kinase inhibitor is a compound represented by formula (II):

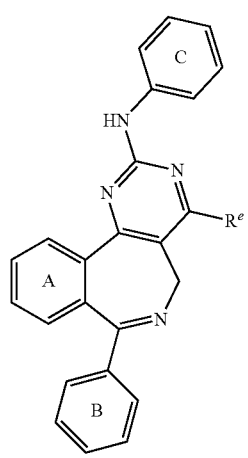

(II)

or a pharmaceutically acceptable salt thereof;
wherein:
R$^e$ is hydrogen or a C$_{1-3}$ aliphatic optionally substituted with R$^3$ or R$^7$;
Ring A is substituted with 0-3 R$^b$;
  each R$^b$ independently is selected from the group consisting of C$_{1-6}$ aliphatic, R$^{2b}$, R$^{7b}$, -T$^1$-R$^{2b}$, and -T$^1$-R$^{7b}$;
  each R$^{2b}$ independently is -halo, —NO$_2$, —CN, —C(R$^5$)=C(R$^5$)$_2$, —C≡C—R$^5$, —OR$^5$, —SR$^6$, —S(O)R$^6$, —SO$_2$R$^6$, —SO$_2$N(R$^4$)$_2$, —N(R$^4$)$_2$, —NR$^4$C(O)R$^5$, —NR$^4$C(O)N(R$^4$)$_2$, —NR$^4$CO$_2$R$^6$, —O—CO$_2$R$^5$, —OC(O)N(R$^4$)$_2$, —O—C(O)R$^5$, —CO$_2$R$^5$, —C(O)—C(O)R$^5$, —C(O)R$^5$, —C(O)N(R$^4$)$_2$, —C(=NR$^4$)—N(R$^4$)$_2$, —C(=NR$^4$)—OR$^5$, —N(R$^4$)—N(R$^4$)$_2$, —N(R$^4$)C(=NR$^4$)—N(R$^4$)$_2$, —N(R$^4$)SO$_2$R$^6$, —N(R$^4$)SO$_2$N(R$^4$)$_2$, —P(O)(R$^5$)$_2$, or —P(O)(OR$^5$)$_2$;
  each R$^{7b}$ independently is an optionally substituted aryl, heterocyclyl, or heteroaryl group;
Ring B is substituted with 0-2 independently selected R$^c$ and 0-2 independently selected R$^{2c}$ or C$_{1-6}$ aliphatic groups;
  each R$^c$ independently is selected from the group consisting of C$_{1-6}$ aliphatic, R$^{2c}$, R$^{7c}$, -T$^1$-R$^{2c}$, and -T$^1$-R$^{7c}$;
  each R$^{2c}$ independently is -halo, —NO$_2$, —CN, —C(R$^5$)=C(R$^5$)$_2$, —C≡C—R$^5$, —OR$^5$, —SR$^6$, —S(O)R$^6$, —SO$_2$R$^6$, —SO$_2$N(R$^4$)$_2$, —N(R$^4$)$_2$, —NR$^4$C(O)R$^5$, —NR$^4$C(O)N(R$^4$)$_2$, —NR$^4$CO$_2$R$^6$, —O—CO$_2$R$^5$, —OC(O)N(R$^4$)$_2$, —O—C(O)R$^5$, —CO$_2$R$^5$, —C(O)—C(O)R$^5$, —C(O)R$^5$, —C(O)N(R$^4$)$_2$, —C(=NR$^4$)—N(R$^4$)$_2$, —C(=NR$^4$)—OR$^5$, —N(R$^4$)—N(R$^4$)$_2$, —N(R$^4$)C(=NR$^4$)—N(R$^4$)$_2$, —N(R$^4$)SO$_2$R$^6$, —N(R$^4$)SO$_2$N(R$^4$)$_2$, —P(O)(R$^5$)$_2$, or —P(O)(OR$^5$)$_2$;
  each R$^{7c}$ independently is an optionally substituted aryl, heterocyclyl, or heteroaryl group;
T$^1$ is a C$_{1-6}$ alkylene chain optionally substituted with R$^3$ or R$^{3b}$, wherein T$^1$ or a portion thereof optionally forms part of a 3- to 7-membered ring;
Ring C is substituted with 0-2 independently selected R$^d$ and 0-3 independently selected R$^{2d}$ or C$_{1-6}$ aliphatic groups;
  each R$^d$ independently is selected from the group consisting of C$_{1-6}$ aliphatic, R$^{2d}$, R$^{7d}$, -T$^2$-R$^{2d}$, -T$^2$-R$^{7d}$, —V-T$^3$-R$^{2d}$, and —V-T$^3$-R$^{7d}$;
T$^2$ is a C$_{1-6}$ alkylene chain optionally substituted with R$^3$ or R$^{3b}$, wherein the alkylene chain optionally is interrupted by —C(R$^5$)=C(R$^5$)—, —C≡C—, —O—, —S—, —S(O)—, —S(O)$_2$—, —SO$_2$N(R$^4$)—, —N(R$^4$)—, —N(R$^4$)C(O)—, —NR$^4$C(O)N(R$^4$)—, —N(R$^4$)CO$_2$—, —C(O)N(R$^4$)—, —C(O)—, —C(O)—C(O)—, —CO$_2$—, —OC(O)—, —OC(O)O—, —OC(O)N(R$^4$)—, —N(R$^4$)—N(R$^4$)—, —N(R$^4$)SO$_2$—, or —SO$_2$N(R$^4$)—, and wherein T$^2$ or a portion thereof optionally forms part of a 3-7 membered ring;
T$^3$ is a C$_{1-6}$ alkylene chain optionally substituted with R$^3$ or R$^{3b}$, wherein the alkylene chain optionally is interrupted by —C(R$^5$)=C(R$^5$)—, —C≡C—, —O—, —S—, —S(O)—, —S(O)$_2$—, —SO$_2$N(R$^4$)—, —N(R$^4$)—, —N(R$^4$)C(O)—, —NR$^4$C(O)N(R$^4$)—, —N(R$^4$)CO$_2$—, —C(O)N(R$^4$)—, —C(O)—, —C(O)—C(O)—, —CO$_2$—, —OC(O)—, —OC(O)O—, —OC(O)N(R$^4$)—, —N(R$^4$)—

$N(R^4)$—, —$N(R^4)SO_2$—, or —$SO_2N(R^4)$—, and wherein $T^3$ or a portion thereof optionally forms part of a 3-7 membered ring;

V is —$C(R^5)$=$C(R^5)$—, —C≡C—, —O—, —S—, —S(O)—, —S(O)$_2$—, —$SO_2N(R^4)$—, —$N(R^4)$—, —$N(R^4)C(O)$—, —$NR^4C(O)N(R^4)$—, —$N(R^4)CO_2$—, —$C(O)N(R^4)$—, —C(O)—, —C(O)—C(O)—, —$CO_2$—, —OC(O)—, —OC(O)O—, —OC(O)$N(R^4)$—, —$C(NR^4)$=N—, —$C(OR^5)$=N—, —$N(R^4)$—$N(R^4)$—, —$N(R^4)SO_2$—, —$N(R^4)SO_2N(R^4)$—, —$P(O)(R^5)$—, —$P(O)(OR^5)$—O—, —P(O)—O—, or —$P(O)(NR^5)$—$N(R^5)$—;

$R^{2d}$ is -halo, —$NO_2$, —CN, —$C(R^5)$=$C(R^5)_2$, —C≡C—$R^5$, —$OR^5$, —$SR^6$, —$S(O)R^6$, —$SO_2R^6$, —$SO_2N(R^4)_2$, —$N(R^4)_2$, —$NR^4C(O)R^5$, —$NR^4C(O)N(R^4)_2$, —$NR^4CO_2R^6$, —O—$CO_2R^5$, —OC(O)$N(R^4)_2$, —O—$C(O)R^5$, —$CO_2R^5$, —C(O)—C(O)$R^5$, —$C(O)R^5$, —$C(O)N(R^4)_2$, —C(=$NR^4$)—$N(R^4)_2$, —C(=$NR^4$)—$OR^5$, —$N(R^4)$—$N(R^4)_2$, —$N(R^4)C$(=$NR^4$)—$N(R^4)_2$, —$N(R^4)SO_2R^6$, —$N(R^4)SO_2N(R^4)_2$, —$P(O)(R^5)_2$, or —$P(O)(OR^5)_2$; and each $R^{7d}$ independently is an optionally substituted aryl, heterocyclyl, or heteroaryl group.

each $R^3$ independently is selected from the group consisting of -halo, —OH, —O($C_{1-3}$ alkyl), —CN, —$N(R^4)_2$, —C(O)($C_{1-3}$ alkyl), —$CO_2H$, —$CO_2$($C_{1-3}$ alkyl), —C(O)$NH_2$, and —C(O)NH($C_{1-3}$ alkyl);

each $R^{3b}$ independently is a $C_{1-3}$ aliphatic optionally substituted with $R^3$ or $R^7$, or two substituents $R^{3b}$ on the same carbon atom, taken together with the carbon atom to which they are attached, form a 3- to 6-membered carbocyclic ring;

each $R^4$ independently is hydrogen or an optionally substituted aliphatic, aryl, heteroaryl, or heterocyclyl group; or two $R^4$ on the same nitrogen atom, taken together with the nitrogen atom, form an optionally substituted 5- to 8-membered heteroaryl or heterocyclyl ring having, in addition to the nitrogen atom, 0-2 ring heteroatoms selected from N, O, and S;

each $R^5$ independently is hydrogen or an optionally substituted aliphatic, aryl, heteroaryl, or heterocyclyl group;

each $R^6$ independently is an optionally substituted aliphatic or aryl group; and each $R^7$ independently is an optionally substituted aryl, heterocyclyl, or heteroaryl group.

Table 1 provides the chemical names for specific examples of compounds of formula (II).

TABLE 1

Examples of Compounds of Formula (II)

| | |
|---|---|
| II-1: | 4-[9-Chloro-7-(2-fluoro-phenyl)-5H-benzo[c]pyrimido[4,5-e]azepin-2-ylamino]-N-(2-methylamino-ethyl)-benzamide |
| II-2: | N-(2-Amino-ethyl)-4-[9-chloro-7-(2-fluoro-phenyl)-5H-benzo[c]pyrimido-[4,5-e]azepin-2-ylamino]-N-methyl-benzamide |
| II-3: | 4-[9-Chloro-7-(2-fluoro-phenyl)-5H-benzo[c]pyrimido[4,5-e]azepin-2-ylamino]-N-methyl-N-(2-methylamino-ethyl)-benzamide |
| II-4: | 4-[9-Chloro-7-(2-fluoro-phenyl)-5H-benzo[c]pyrimido[4,5-e]azepin-2-ylamino]-N-(2-dimethylamino-ethyl)-benzamide |
| II-5: | 4-[9-Chloro-7-(2-fluoro-phenyl)-5H-benzo[c]pyrimido[4,5-e]azepin-2-ylamino]-N-(2-dimethylamino-ethyl)-N-methyl-benzamide |
| II-6: | 4-[9-Chloro-7-(2-fluoro-phenyl)-5H-benzo[c]pyrimido[4,5-e]azepin-2-ylamino]-N-(3-dimethylamino-propyl)-benzamide |
| II-7: | 4-[9-Chloro-7-(2-fluoro-phenyl)-5H-benzo[c]pyrimido[4,5-e]azepin-2-ylamino]-N-(3-dimethylamino-propyl)-N-methyl-benzamide |
| II-8: | {4-[9-Chloro-7-(2-fluoro-phenyl)-5H-benzo[c]pyrimido[4,5-e]azepin-2-ylamino]-phenyl}-piperazin-1-yl-methanone |
| II-9: | {4-[9-Chloro-7-(2-fluoro-phenyl)-5H-benzo[c]pyrimido[4,5-e]azepin-2-ylamino]-phenyl}-(4-methyl-piperazin-1-yl)-methanone |
| II-10: | {4-[9-Chloro-7-(2-chloro-phenyl)-5H-benzo[c]pyrimido[4,5-e]azepin-2-ylamino]-phenyl}-(4-methyl-piperazin-1-yl)-methanone |
| II-11: | [4-(9-Chloro-7-o-tolyl-5H-benzo[c]pyrimido[4,5-e]azepin-2-ylamino)-phenyl]-(4-methyl-piperazin-1-yl)-methanone |
| II-12: | {4-[9-Chloro-7-(2-methoxy-phenyl)-5H-benzo[c]pyrimido[4,5-e]azepin-2-ylamino]-phenyl}-(4-methyl-piperazin-1-yl)-methanone |
| II-13: | {4-[9-Chloro-7-(4-fluoro-phenyl)-5H-benzo[c]pyrimido[4,5-e]azepin-2-ylamino]-phenyl}-(4-methyl-piperazin-1-yl)-methanone |
| II-14: | {4-[7-(2-Fluoro-phenyl)-9-methyl-5H-benzo[c]pyrimido[4,5-e]azepin-2-ylamino]-phenyl}-(4-methyl-piperazin-1-yl)-methanone |
| II-15: | 2-{3-[9-Chloro-7-(2-fluoro-phenyl)-5H-benzo[c]pyrimido[4,5-e]azepin-2-ylamino]-phenyl}-1-(4-methyl-piperazin-1-yl)-ethanone |
| II-16: | 4-[9-Chloro-7-(2-fluoro-phenyl)-5H-benzo[c]pyrimido[4,5-e]azepin-2-ylamino]-N-piperidin-4-yl-benzamide |
| II-17: | (4-amino-piperidin-1-yl)-{4-[9-chloro-7-(2-fluoro-phenyl)-5H-benzo[c]pyrimido[4,5-e]azepin-2-ylamino]-phenyl]-methanone |
| II-18: | {4-[9-Chloro-7-(2-fluoro-phenyl)-5H-benzo[c]pyrimido[4,5-e]azepin-2-ylamino]-phenyl}-(4-dimethylamino-piperidin-1-yl)-methanone |
| II-19: | 4-[9-Chloro-7-(2-fluoro-phenyl)-5H-benzo[c]pyrimido[4,5-e]azepin-2-ylamino]-N-[3-(4-methyl-piperazin-1-yl)-propyl]-benzamide |
| II-20: | 4-[9-Chloro-7-(2-chloro-phenyl)-5H-benzo[c]pyrimido[4,5-e]azepin-2-ylamino]-N-[3-(4-methyl-piperazin-1-yl)-propyl]-benzamide |
| II-21: | 4-(9-Chloro-7-o-tolyl-5H-benzo[c]pyrimido[4,5-e]azepin-2-ylamino)-N-[3-(4-methyl-piperazin-1-yl)-propyl]-benzamide |
| II-22: | 4-[9-Chloro-7-(2-methoxy-phenyl)-5H-benzo[c]pyrimido[4,5-e]azepin-2-ylamino]-N-[3-(4-methyl-piperazin-1-yl)-propyl]-benzamide |
| II-23: | 4-[9-Chloro-7-(4-fluoro-phenyl)-5H-benzo[c]pyrimido[4,5-e]azepin-2-ylamino]-N-[3-(4-methyl-piperazin-1-yl)-propyl]-benzamide |

TABLE 1-continued

Examples of Compounds of Formula (II)

| | |
|---|---|
| II-24: | 4-[7-(2-Fluoro-phenyl)-9-methyl-5H-benzo[c]pyrimido[4,5-e]azepin-2-ylamino]-N-[3-(4-methyl-piperazin-1-yl)-propyl]-benzamide |
| II-25: | 2-{3-[9-Chloro-7-(2-fluoro-phenyl)-5H-benzo[c]pyrimido[4,5-e]azepin-2-ylamino]-phenyl}-N-[3-(4-methyl-piperazin-1-yl)-propyl]-acetamide |
| II-26: | {4-[9-Chloro-7-(2-fluoro-phenyl)-5H-benzo[c]pyrimido[4,5-e]azepin-2-ylamino]-phenyl}-morpholin-4-yl-methanone |
| II-27: | 4-[9-Chloro-7-(2-fluoro-phenyl)-5H-benzo[c]pyrimido[4,5-e]azepin-2-ylamino]-N,N-bis-(2-hydroxy-ethyl)-benzamide |
| II-28: | {4-[9-Chloro-7-(2-chloro-phenyl)-5H-benzo[c]pyrimido[4,5-e]azepin-2-ylamino]-phenyl}-morpholin-4-yl-methanone |
| II-29: | 4-[9-Chloro-7-(2-fluoro-phenyl)-5H-benzo[c]pyrimido[4,5-e]azepin-2-ylamino]-N-(2-morpholin-4-yl-ethyl)-benzamide |
| II-30: | 4-[9-Chloro-7-(2-chloro-phenyl)-5H-benzo[c]pyrimido[4,5-e]azepin-2-ylamino]-N-(2-morpholin-4-yl-ethyl)-benzamide |
| II-31: | 4-(9-Chloro-7-o-tolyl-5H-benzo[c]pyrimido[4,5-e]azepin-2-ylamino)-N-(2-morpholin-4-yl-ethyl)-benzamide |
| II-32: | 4-[9-Chloro-7-(2-methoxy-phenyl)-5H-benzo[c]pyrimido[4,5-e]azepin-2-ylamino]-N-(3-morpholin-4-yl-propyl)-benzamide |
| II-33: | 4-[9-Chloro-7-(4-fluoro-phenyl)-5H-benzo[c]pyrimido[4,5-e]azepin-2-ylamino]-N-(2-morpholin-4-yl-ethyl)-benzamide |
| II-34: | 4-[9-Chloro-7-(2-chloro-phenyl)-5H-benzo[c]pyrimido[4,5-e]azepin-2-ylamino]-2-hydroxy-N-{2-morpholin-4-yl-ethyl-benzamide |
| II-35: | [9-Chloro-7-(2-chloro-phenyl)-5H-benzo[c]pyrimido[4,5-e]azepin-2-yl]-pyridin-2-yl-amine |
| II-36: | [9-Chloro-7-(2-fluoro-phenyl)-5H-benzo[c]pyrimido[4,5-e]azepin-2-yl]-(3,5-dichloro-phenyl)-amine |
| II-37: | [9-Chloro-7-(2-fluoro-phenyl)-5H-benzo[c]pyrimido[4,5-e]azepin-2-yl]-{4-methoxy-phenyl)-amine |
| II-38: | [9-Chloro-7-(2-fluoro-phenyl)-5H-benzo[c]pyrimido[4,5-e]azepin-2-yl]-(4-ethoxy-phenyl)-amine |
| II-39: | [9-Chloro-7-(2-fluoro-phenyl)-5H-benzo[c]pyrimido[4,5-e]azepin-2-yl]-(3-methoxy-phenyl)-amine |
| II-40: | [9-Chloro-7-(2-fluoro-phenyl)-5H-benzo[c]pyrimido[4,5-e]azepin-2-yl]-(2-methoxy-phenyl)-amine |
| II-41: | [9-Chloro-7-(2-fluoro-phenyl)-5H-benzo[c]pyrimido[4,5-e]azepin-2-yl]-(4-chloro-phenyl)-amine |
| II-42: | [9-Chloro-7-(2-chloro-phenyl)-5H-benzo[c]pyrimido[4,5-e]azepin-2-yl]-(4-chloro-phenyl)-amine |
| II-43: | [9-Chloro-7-(2-fluoro-phenyl)-5H-benzo[c]pyrimido[4,5-e]azepin-2-yl]-(3-chloro-phenyl)-amine |
| II-44: | [9-Chloro-7-(2-fluoro-phenyl)-5H-benzo[c]pyrimido[4,5-e]azepin-2-yl]-(2-chloro-phenyl)-amine |
| II-45: | 4-[9-Chloro-7-(2-chloro-phenyl)-5H-benzo[c]pyrimido[4,5-e]azepin-2-ylamino]-phenol |
| II-46: | [9-Chloro-7-(2-fluoro-phenyl)-5H-benzo[c]pyrimido[4,5-e]azepin-2-yl]-(4-morpholin-4-yl-phenyl)-amine |
| II-47: | [9-Chloro-7-(2-fluoro-phenyl)-5H-benzo[c]pyrimido[4,5-e]azepin-2-yl]-[4-(4-methyl-piperazin-1-yl)-phenyl]-amine |
| II-48: | [9-Chloro-7-(2-fluoro-phenyl)-5H-benzo[c]pyrimido[4,5-e]azepin-2-yl]-(4-pyridin-4-ylmethyl-phenyl)-amine |
| II-49: | 4-[9-Chloro-7-(2-fluoro-phenyl)-5H-benzo[c]pyrimido[4,5-e]azepin-2-ylamino]-benzonitrile |
| II-50: | [9-Chloro-7-(2-fluoro-phenyl)-5H-benzo[c]pyrimido[4,5-e]azepin-2-yl]-(4-nitro-phenyl)-amine |
| II-51: | 4-[7-(2-Fluoro-phenyl)-5H-benzo[c]pyrimido[4,5-e]azepin-2-ylamino]-benzoic acid |
| II-52: | 4-[9-Chloro-7-(2-fluoro-phenyl)-5H-benzo[c]pyrimido[4,5-e]azepin-2-ylamino]-benzoic acid |
| II-53: | 4-[9-Chloro-7-(2-chloro-phenyl)-5H-benzo[c]pyrimido[4,5-e]azepin-2-ylamino]-benzoic acid |
| II-54: | 4-(9-Chloro-7-o-tolyl-5H-benzo[c]pyrimido[4,5-e]azepin-2-ylamino)-benzoic acid |
| II-55: | 4-[9-Chloro-7-(2-methoxy-phenyl)-5H-benzo[c]pyrimido[4,5-e]azepin-2-ylamino]-benzoic acid |
| II-56: | 4-[9-Chloro-7-(4-fluoro-phenyl)-5H-benzo[c]pyrimido[4,5-e]azepin-2-ylamino]-benzoic acid |
| II-57: | 4-[9-Fluoro-7-(2-fluoro-phenyl)-5H-benzo[c]pyrimido[4,5-e]azepin-2-ylamino]-benzoic acid |
| II-58: | 4-[7-(2-Fluoro-phenyl)-9-methyl-5H-benzo[c]pyrimido[4,5-e]azepin-2-ylamino]-benzoic acid |
| II-59: | 4-[10-Fluoro-7-(2-fluoro-phenyl)-5H-benzo[c]pyrimido[4,5-e]azepin-2-ylamino]-benzoic acid |
| II-60: | 4-[10-Chloro-7-(2-fluoro-phenyl)-5H-benzo[c]pyrimido[4,5-e]azepin-2-ylamino]-benzoic acid |
| II-61: | 4-[10-Bromo-7-(2-fluoro-phenyl)-5H-benzo[c]pyrimido[4,5-e]azepin-2-ylamino]-benzoic acid |
| II-62: | 4-[7-(2-Fluoro-phenyl)-10-methoxy-5H-benzo[c]pyrimido[4,5-e]azepin-2-ylamino]-benzoic acid |

TABLE 1-continued

Examples of Compounds of Formula (II)

| | |
|---|---|
| II-63: | 4-[9-Chloro-7-(2-chloro-phenyl)-5H-benzo[c]pyrimido[4,5-e]azepin-2-ylamino]-benzamide |
| II-64: | 3-[9-Chloro-7-(2-chloro-phenyl)-5H-benzo[c]pyrimido[4,5-e]azepin-2-ylamino]-benzamide |
| II-65: | {3-[9-Chloro-7-(2-chloro-phenyl)-5H-benzo[c]pyrimido[4,5-e]azepin-2-ylamino]-phenyl}-acetic acid |
| II-66: | 2-{3-[9-Chloro-7-(2-chloro-phenyl)-5H-benzo[c]pyrimido[4,5-e]azepin-2-ylamino]-phenyl}-acetamide |
| II-67: | 4-[9-Chloro-7-(2-fluoro-phenyl)-5H-benzo[c]pyrimido[4,5-e]azepin-2-ylamino]-benzenesulfonic acid |
| II-68: | 4-[9-Chloro-7-(2-fluoro-phenyl)-5H-benzo[c]pyrimido[4,5-e]azepin-2-ylamino]-benzenesulfonamide |
| II-69: | 4-[9-Chloro-7-(2-chloro-phenyl)-5H-benzo[c]pyrimido[4,5-e]azepin-2-ylamino]-N-(5-methyl-isoxazol-3-yl)-benzenesulfonamide |
| II-70: | [9-Chloro-7-(2-fluoro-phenyl)-5H-benzo[c]pyrimido[4,5-e]azepin-2-yl]-(4-trifluoromethanesulfonyl-phenyl)-amine |
| II-71: | [9-Chloro-7-(2-fluoro-phenyl)-5H-benzo[c]pyrimido[4,5-e]azepin-2-yl]-(3,4-dimethoxy-phenyl)-amine |
| II-72: | [9-Chloro-7-(2-fluoro-phenyl)-6,7-dihydro-5H-benzo[c]pyrimido-[4,5-e]azepin-2-yl]-(3,4-dimethoxy-phenyl)-amine |
| II-73: | [9-Chloro-7-(2-chloro-phenyl)-5H-benzo[c]pyrimido[4,5-e]azepin-2-yl]-(3,4-dimethoxy-phenyl)-amine |
| II-74: | (9-Chloro-7-o-tolyl-5H-benzo[c]pyrimido[4,5-e]azepin-2-yl)-(3,4-dimethoxy-phenyl)-amine |
| II-75: | (3,4-Dimethoxy-phenyl)-[7-(2-fluoro-phenyl)-9-methyl-5H-benzo[c]pyrimido[4,5-e]azepin-2-yl]-amine |
| II-76: | (3,4-Dimethoxy-phenyl)-[7-(2-fluoro-phenyl)-9-isopropyl-5H-benzo[c]pyrimido[4,5-e]azepin-2-yl]-amine |
| II-77: | (3,4-Dimethoxy-phenyl)-[10-fluoro-7-(2-fluoro-phenyl)-5H-benzo[c]pyrimido[4,5-e]azepin-2-yl]-amine |
| II-78: | [10-Bromo-7-(2-fluoro-phenyl)-5H-benzo[c]pyrimido[4,5-e]azepin-2-yl]-(3,4-dimethoxy-phenyl)-amine |
| II-79: | (3,4-Dimethoxy-phenyl)-[7-(2-fluoro-phenyl)-10-trifluoromethyl-5H-benzo[c]pyrimido[4,5]azepin-2-yl]-amine |
| II-80: | (3,4-Dimethoxy-phenyl)-[7-(2-fluoro-phenyl)-10-methyl-5H-benzo[c]pyrimido[4,5-e]azepin-2-yl]-amine |
| II-81: | (3,4-Dimethoxy-phenyl)-[7-(2-fluoro-phenyl)-10-methoxy-5H-benzo[c]pyrimido[4,5-e]azepin-2-yl]-amine |
| II-82: | (3,4-Dimethoxy-phenyl)-[7-(2-fluoro-phenyl)-11-methyl-5H-benzo[c]pyrimido[4,5-e]azepin-2-yl]-amine |
| II-83: | [9-Chloro-7-(2-fluoro-phenyl)-5H-benzo[c]pyrimido[4,5-e]azepin-2-yl]-(2,3-dihydro-benzo[1,4]dioxin-6-yl)-amine |
| II-84: | [9-Chloro-7-(2-fluoro-phenyl)-5H-benzo[c]pyrimido[4,5-e]azepin-2-yl]-(4-fluoro-3-methoxy-phenyl)-amine |
| II-85: | 4-[9-Chloro-7-(2-fluoro-phenyl)-5H-benzo[c]pyrimido[4,5-e]azepin-2-ylamino]-2-hydroxy-benzoic acid |
| II-86: | 4-[9-Chloro-7-(2-chloro-phenyl)-5H-benzo[c]pyrimido[4,5-e]azepin-2-ylamino]-2-hydroxy-benzoic acid |
| II-87: | [9-Chloro-7-(2-fluoro-phenyl)-5H-benzo[c]pyrimido[4,5-e]azepin-2-yl]-(3,4-dichloro-phenyl)-amine |
| II-88: | [9-Chloro-7-(2-chloro-phenyl)-5H-benzo[c]pyrimido[4,5-e]azepin-2-yl]-(3,5-dimethoxy-phenyl)-amine |
| II-89: | [9-Chloro-7-(2-fluoro-phenyl)-5H-benzo[c]pyrimido[4,5-e]azepin-2-yl]-(3,5-dimethyl-phenyl)-amine |
| II-90: | [9-Chloro-7-(2-fluoro-phenyl)-5H-benzo[c]pyrimido[4,5-c]azepin-2-yl]-phenyl-amine |
| II-91: | 4-[9-Chloro-7-(2,5-difluoro-phenyl)-5H-benzo[c]pyrimido[4,5-e]azepin-2-ylamino]-benzoic acid |
| II-92: | 4-[9-Chloro-7-(2,3-difluoro-phenyl)-5H-benzo[c]pyrimido[4,5-e]azepin-2-ylamino]-benzoic acid |
| II-93: | (3-Dimethylamino-pyrrolidin-1-yl)-{4-[7-(2-fluoro-phenyl)-9-methoxy-5H-benzo[c]pyrimido[4,5-e]azepin-2-ylamino]-phenyl}-methanone |
| II-94: | 4-[9-Chloro-7-(2,5-dimethoxy-phenyl)-5H-benzo[c]pyrimido-[4,5-e]azepin-2-ylamino]-benzoic acid |
| II-95: | 4-[7-(2-Fluoro-phenyl)-9-methoxy-5H-benzo[c]pyrimido[4,5-e]azepin-2-ylamino]-N,N-bis-(2-hydroxy-ethyl)-benzamide |
| II-96: | 4-[9-Chloro-7-(2,4-difluoro-phenyl)-5H-benzo[c]pyrimido[4,5-e]azepin-2-ylamino]-benzoic acid |
| II-97: | 4-[9-Chloro-7-(2,4-difluoro-phenyl)-7H-benzo[c]pyrimido[4,5-e]azepin-2-ylamino]-benzoic acid |
| II-98: | {4-[9-Chloro-7-(2-fluoro-phenyl)-5H-benzo[c]pyrimido[4,5-e]azepin-2-ylamino]-phenyl}-(3-dimethylamino-azetidin-1-yl)-methanone |
| II-99: | 4-[9-Chloro-7-(2-fluoro-phenyl)-5H-benzo[c]pyrimido[4,5-e]azepin-2-ylamino]-N-methyl-N-(1-methyl-pyrrolidin-3-yl)-benzamide |
| II-100: | {4-[9-Chloro-7-(2-fluoro-phenyl)-5H-benzo[c]pyrimido[4,5-e]azepin-2-ylamino]-phenyl}-(3-dimethylamino-pyrrolidin-1-yl)-methanone |
| II-101: | 4-[9-Chloro-7-(2,4-dimethoxy-phenyl)-5H-benzo[c]pyrimido-[4,5-e]azepin-2-ylamino]-benzoic acid |

TABLE 1-continued

Examples of Compounds of Formula (II)

| | |
|---|---|
| II-102: | {4-[9-Chloro-7-(2-fluoro-phenyl)-5H-benzo[c]pyrimido[4,5-e]azepin-2-ylamino]-phenyl}-(3-methylamino-pyrrolidin-1-yl)-methanone |
| II-103: | (3-Amino-pyrrolidin-1-yl)-{4-[9-chloro-7-(2-fluorophenyl)-5H-benzo[c]pyrimido[4,5-e]azepin-2-ylamino]-phenyl}-methanone |
| II-104: | 4-[9-Chloro-7-(2,3-difluoro-phenyl)-5H-benzo[c]pyrimido[4,5-e]azepin-2-ylamino]-benzoic acid methyl ester |
| II-105: | 4-[9-Chloro-7-(2,5-difluoro-phenyl)-5H-benzo[c]pyrimido[4,5-e]azepin-2-ylamino]-benzoic acid methyl ester |
| II-106: | {4-[9-Chloro-7-(2-fluoro-phenyl)-5H-benzo[c]pyrimido[4,5-e]azepin-2-ylamino]-phenyl}-phosphonic acid |
| II-107: | N-{4-[9-Chloro-7-(2-fluoro-phenyl)-5H-benzo[c]pyrimido[4,5-e]azepin-2-ylamino]-phenyl}-methanesulfonamide |
| II-108: | N-{4-[9-Chloro-7-(2-fluoro-phenyl)-5H-benzo[c]pyrimido[4,5-e]azepin-2-ylamino]-phenyl}-N-methyl-acetamide |
| II-109: | 2-{4-[9-Chloro-7-(2-fluoro-phenyl)-5H-benzo[c]pyrimido[4,5-e]azepin-2-ylamino]-benzoylamino}-succinic acid |
| II-110: | [9-Chloro-7-(2-fluoro-phenyl)-4-methyl-5H-benzo[c]pyrimido-[4,5-e]azepin-2-yl]-(3,4-dimethoxy-phenyl)-amine |
| II-111: | {4-[9-Chloro-7-(2-fluoro-phenyl)-5H-benzo[c]pyrimido[4,5-e]azepin-2-ylamino]-phenyl}-(3,5-dimethyl-piperazin-1-yl)-methanone |
| II-112: | 1-{4-[9-Chloro-7-(2-fluoro-phenyl)-5H-benzo[c]pyrimido[4,5-e]azepin-2-ylamino]-benzoyl)-pyrrolidine-2-carboxylic acid |
| II-113: | {4-[9-Chloro-7-(2-fluoro-phenyl)-5H-benzo[c]pyrimido[4,5-e]azepin-2-ylamino]-phenyl}-(3-methyl-piperazin-1-yl)-methanone |
| II-114: | [9-Chloro-7-(2-fluoro-phenyl)-5H-benzo[c]pyrimido[4,5-e]azepin-2-yl]-[4-(2H-tetrazol-5-yl)-phenyl]-amine |
| II-115: | N-{4-[9-Chloro-7-(2-fluoro-phenyl)-5H-benzo[c]pyrimido[4,5-e]azepin-2-ylamino]-phenyl}-acetamide |
| II-116: | 5-[9-Chloro-7-(2-fluoro-phenyl)-5H-benzo[c]pyrimido[4,5-e]azepin-2-ylamino]-2-fluoro-benzoic acid |
| II-117: | N-(3-Amino-propyl)-4-[9-chloro-7-(2-fluoro-phenyl)-5H-benzo[c]pyrimido[4,5-e]azepin-2-ylamino]-N-methyl-benzamide |
| II-118: | 2-{4-[9-Chloro-7-(2-fluoro-phenyl)-5H-benzo[c]pyrimido[4,5-e]azepin-2-ylamino]-benzoylamino}-propionic acid |
| II-119: | 5-[9-Chloro-7-(2-fluoro-phenyl)-5H-benzo[c]pyrimido[4,5-e]azepin-2-ylamino]-pyridine-2-carboxylic acid |
| II-120: | 2-{4-[9-Chloro-7-(2-fluoro-phenyl)-5H-benzo[c]pyrimido[4,5-e]azepin-2-ylamino]-phenyl}-N-(2-morpholin-4-yl-ethyl)-acetamide |
| II-121: | 5-[9-Chloro-7-(2-fluoro-phenyl)-5H-benzo[c]pyrimido[4,5-e]azepin-2-ylamino]-2-methoxy-benzoic acid |
| II-122: | 5-[9-Chloro-7-(2-fluoro-phenyl)-5H-benzo[c]pyrimido[4,5-e]azepin-2-ylamino]-2-methyl-benzoic acid |
| II-123: | 6-[9-Chloro-7-(2-fluoro-phenyl)-5H-benzo[c]pyrimido[4,5-e]azepin-2-ylamino]-nicotinic acid |
| II-124: | 4-[9-Chloro-7-(2-fluoro-phenyl)-5H-benzo[c]pyrimido[4,5-e]azepin-2-ylamino]-N-(2-morpholin-4-yl-ethyl)-benzenesulfonamide |
| II-125: | 2-Chloro-5-[9-chloro-7-(2-fluoro-phenyl)-5H-benzo[c]pyrimido-[4,5-e]azepin-2-ylamino]-benzoic acid |
| II-126: | {4-[9-Chloro-7-(2-fluoro-phenyl)-5H-benzo[c]pyrimido[4,5-e]azepin-2-ylamino]-phenyl}-acetic acid |
| II-127: | 4-[9-Chloro-7-(2-fluoro-phenyl)-5H-benzo[c]pyrimido[4,5-e]azepin-2-ylamino]-2-trifluoromethyl-benzoic acid |
| II-128: | 4-[9-Chloro-7-(2-fluoro-phenyl)-5H-benzo[c]pyrimido[4,5-e]azepin-2-ylamino]-N-methyl-N-(1-methyl-piperidin-4-yl)-benzamide |
| II-129: | N-(3-Amino-propyl)-4-[9-chloro-7-(2-fluoro-phenyl)-5H-benzo[c]pyrimido[4,5-e]azepin-2-ylamino]-benzamide |
| II-130: | 4-[9-Chloro-7-(2-fluoro-phenyl)-5H-benzo[c]pyrimido[4,5-e]azepin-2-ylamino]-N-(3-methylamino-propyl)-benzamide |
| II-131: | N-(2-Amino-2-methyl-propyl)-4-[9-chloro-7-(2-fluoro-phenyl)-5H-benzo[c]pyrimido[4,5-e]azepin-2-ylamino]-benzamide |
| II-132: | 2-(3,4-Dimethoxy-phenylamino)-7-(2-fluoro-phenyl)-5H-benzo[c]pyrimido[4,5-e]azepine-10-carboxylic acid |
| II-133: | 4-[9-Chloro-7-(2-fluoro-phenyl)-5H-benzo[c]pyrimido[4,5-e]azepin-2-ylamino]-2-methyl-benzoic acid |
| II-134: | 2-Chloro-4-[9-chloro-7-(2-fluoro-phenyl)-5H-benzo[c]pyrimido-[4,5-e]azepin-2-ylamino]-benzoic acid |
| II-135: | 4-[9-Chloro-7-(2,6-difluoro-phenyl)-5H-benzo[c]pyrimido[4,5-e]azepin-2-ylamino]-benzoic acid |
| II-136: | 4-[9-Chloro-7-(2-fluoro-phenyl)-5H-benzo[c]pyrimido[4,5-e]azepin-2-ylamino]-2-fluoro-benzoic acid |
| II-137: | 4-[7-(2-Fluoro-phenyl)-9-methoxy-5H-benzo[c]pyrimido[4,5-e]azepin-2-ylamino]-benzoic acid |
| II-138: | (3,4-Dimethoxy-phenyl)-[7-(2-fluoro-phenyl)-9-methoxy-5H-benzo[c]pyrimido[4,5-e]azepin-2-yl]-amine |
| II-139: | [9,10-Dichloro-7-(2-fluoro-phenyl)-5H-benzo[c]pyrimido[4,5-e]azepin-2-yl]-(3,4-dimethoxy-phenyl)-amine |
| II-140: | 4-[9,10-Dichloro-7-(2-fluoro-phenyl)-5H-benzo[c]pyrimido[4,5-e]azepin-2-ylamino]-benzoic acid |

TABLE 1-continued

Examples of Compounds of Formula (II)

| | |
|---|---|
| II-141: | 4-[9-Chloro-7-(2-fluoro-phenyl)-5H-benzo[c]pyrimido[4,5-e]azepin-2-ylamino]-2-methoxy-benzoic acid |
| II-142: | N-(2-Amino-ethyl)-4-[9-chloro-7-(2-fluoro-phenyl)-5H-benzo[c]pyrimido-[4,5-e]azepin-2-ylamino]-benzamide |
| II-143: | 4-(9-Chloro-7-phenyl-5H-benzo[c]pyrimido[4,5-e]azepin-2-ylamino)-benzoic acid |
| II-144: | [7-(2-Bromo-phenyl)-9-chloro-5H-benzo[c]pyrimido[4,5-e]azepin-2-yl]-(3,4-dimethoxy-phenyl]-amine |
| II-145: | 2-{4-[9-Chloro-7-(2-fluoro-phenyl)-5H-benzo[c]pyrimido[4,5-e]azepin-2-ylamino]-phenyl}-1-(4-methyl-piperazin-1-yl)-ethanone |
| II-146: | 3-[9-Chloro-7-(2-fluoro-phenyl)-5H-benzo[c]pyrimido[4,5-e]azepin-2-ylamino]-benzoic acid |
| II-147: | 4-[9-Chloro-7-(2-fluoro-phenyl)-5H-benzo[c]pyrimido[4,5-e]azepin-2-ylamino]-N-[2-(1H-imidazol-4-yl)-ethyl]-benzamide |
| II-148: | 4-[7-(2-Fluoro-phenyl)-9-methyl-5H-benzo[c]pyrimido[4,5-e]azepin-2-ylamino]-N-(2-morpholin-4-yl-ethyl)-benzamide |
| II-149: | {3-[9-Chloro-7-(2-fluoro-phenyl)-5H-benzo[c]pyrimido[4,5-e]azepin-2-ylamino]-phenyl}-acetic acid |
| II-150: | 4-[9-Chloro-7-(2-fluoro-phenyl)-5H-benzo[c]pyrimido[4,5-e]azepin-2-ylamino]-N-(2-pyridin-4-yl-ethyl)-benzamide |
| II-151: | 4-[9-Chloro-7-(2-fluoro-phenyl)-5H-benzo[c]pyrimido[4,5-e]azepin-2-ylamino]-N-(2-pyridin-3-yl-ethyl)-benzamide |
| II-152: | (9-Chloro-7-phenyl-5H-benzo[c]pyrimido[4,5-e]azepin-2-yl)-(3,4-dimethoxy-phenyl)-amine |
| II-153: | 4-[7-(2-Fluoro-phenyl)-10-methyl-5H-benzo[c]pyrimido[4,5-e]azepin-2-ylamino]-benzoic acid |
| II-154: | (3,4-Dimethoxy-phenyl)-[7-(2-fluoro-phenyl)-5H-benzo[c]pyrimido-[4,5-e]azepin-2-yl]-amine |
| II-155: | 4-[9-Chloro-7-(4-methoxy-phenyl)-5H-benzo[c]pyrimido[4,5-e]azepin-2-ylamino]-benzoic acid |
| II-156: | 4-[9-Chloro-7-(3-methoxy-phenyl)-5H-benzo[c]pyrimido[4,5-e]azepin-2-ylamino]-benzoic acid |
| II-157: | 4-[9-Chloro-7-(3-fluoro-phenyl)-5H-benzo[c]pyrimido[4,5-e]azepin-2-ylamino]-N-[3-(4-methyl-piperazin-1-yl)-propyl]-benzamide |
| II-158: | 4-[9-Chloro-7-(3-fluoro-phenyl)-5H-benzo[c]pyrimido[4,5-e]azepin-2-ylamino]-N-(2-morpholin-4-yl-ethyl)-benzamide |
| II-159: | {4-[9-Chloro-7-(3-fluoro-phenyl)-5H-benzo[c]pyrimido[4,5-e]azepin-2-ylamino]-phenyl}-(4-methyl-piperazin-1-yl)-methanone |
| II-160: | 4-[9-Chloro-7-(2-fluoro-phenyl)-5H-benzo[c]pyrimido[4,5-e]azepin-2-ylamino]-N-methyl-N-(2-pyridin-2-yl-ethyl)-benzamide |
| II-161: | 4-[9-Chloro-7-(2-fluoro-phenyl)-5H-benzo[c]pyrimido[4,5-e]azepin-2-ylamino]-N-(2-pyridin-2-yl-ethyl)-benzamide |
| II-162: | 4-[9-Chloro-7-(3-fluoro-phenyl)-5H-benzo[c]pyrimido[4,5-e]azepin-2-ylamino]-benzoic acid |
| II-163: | {3-[9-Chloro-7-(2-fluoro-phenyl)-5H-benzo[c]pyrimido[4,5-e]azepin-2-ylamino]-phenyl}-(4-methyl-piperazin-1-yl)-methanone |
| II-164: | 9-Chloro-7-(2-fluorophenyl)-N-{4-[(4-pyridin-2-ylpiperazin-1-yl)carbonyl]phenyl}-5H-pyrimido[5,4-d][2]benzazepin-2-amine |
| II-165: | 9-Chloro-7-(2-fluorophenyl)-N-(4-{[4-(2-morpholin-4-yl-2-oxoethyl)piperazin-1-yl]carbonyl}phenyl)-5H-pyrimido-[5,4-d][2]benzazepin-2-amine |
| II-166: | 9-Chloro-7-(2-fluorophenyl-N-(4-{[4-(2-furoyl)piperazin-1-yl]carbonyl}phenyl)-5H-pyrimido[5,4-d][2]benzazepin-2-amine |
| II-167: | Benzyl-4-(4-{[9-chloro-7-(2-fluorophenyl)-5H-pyrimido-[5,4-d][2]benzazepin-2-yl]amino}benzoyl)piperazine-1-carboxylate |
| II-168: | Ethyl-4-(4-{[9-Chloro-7-(2-fluorophenyl)-5H-pyrimido-[5,4-d][2]benzazepin-2-yl]amino}benzoyl)piperazine-1-carboxylate |
| II-169: | 2-[4-(4-{[9-Chloro-7-(2-fluorophenyl)-5H-pyrimido[5,4-d][2]benzazepin-2-yl]amino}benzoyl)piperazin-1-yl]benzoic acid |
| II-170: | 2-[4-(4-{[9-Chloro-7-(2-fluorophenyl)-5H-pyrimido[5,4-d][2]benzazepin-2-yl]amino}benzoyl)piperazin-1-yl]-N-isopropylacetamide |
| II-171: | 9-Chloro-7-(2-fluorophenyl)-N-(4-{[4-(2-pyrrolidin-1-ylethyl)piperazin-1-yl]carbonyl}phenyl)-5H-pyrimido[5,4-d][2]benzazepin-2-amine |
| II-172: | N-[2-(aminocarbonyl)phenyl]-4-{[9-chloro-7-(2-fluorophenyl)-5H-pyrimido[5,4-d][2]benzazepin-2-yl]amino}benzamide |
| II-173: | 9-Chloro-7-(2-fluorophenyl)-N-{4-[(4-pyrimidin-2-ylpiperazin-1-yl)carbonyl]phenyl}-5H-pyrimido[5,4-d][2]benzazepin-2-amine |
| II-174: | 4-{[9-Chloro-7-(2-chloro-6-fluorophenyl)-5H-pyrimido-[5,4-d][2]benzazepin-2-yl]amino}benzoic acid |
| II-175: | 9-Chloro-7-(2,6-difluorophenyl)-N-{4-[(3,5-dimethylpiperazin-1-yl)carbonyl]phenyl}-5H-pyrimido[5,4-d][2]benzazepin-2-amine |
| II-176: | 9-Chloro-7-(2,6-difluorophenyl)-N-(4-{[3-(dimethylamino)pyrrolidin-1-yl]carbonyl}phenyl)-5H-pyrimido[5,4-d][2]benzazepin-2-amine |
| II-177: | 9-Chloro-N-{4-[(3,5-dimethylpiperazin-1-yl)carbonyl]phenyl}-7-(2-fluoro-6-methoxyphenyl)-5H-pyrimido[5,4-d][2]benzazepin-2-amine |
| II-178: | 9-Chloro-N-(4-{[3-(dimethylamino)pyrrolidin-1-yl]carbonyl}phenyl)-7-(2-fluoro-6-methoxyphenyl)-5H-pyrimido[5,4-d][2]benzazepin-2-amine |

TABLE 1-continued

Examples of Compounds of Formula (II)

| | |
|---|---|
| II-179: | 9-Chloro-N-(4-{[3-(dimethylamino)azetidin-1-yl]carbonyl}phenyl)-7-(2-fluoro-6-methoxyphenyl)-5H-pyrimido[5,4-d][2]benzazepin-2-amine |
| II-180: | 9-Chloro-7-(2,6-difluorophenyl)-N-(4-{[3-(dimethylamino)azetidin-1-yl]carbonyl}phenyl)-5H-pyrimido[5,4-d][2]benzazepin-2-amine |
| II-181: | {4-[9-Chloro-7-(2-fluoro-phenyl)-5H-benzo[c]pyrimido[4,5-e]azepin-2-ylamino]-phenyl}-[4-(3-piperidin-1-yl-propyl)-piperazin-1-yl]-methanone |
| II-182: | {4-[9-Chloro-7-(2-fluoro-phenyl)-5H-benzo[c]pyrimido[4,5-e]azepin-2-ylamino]-phenyl}-[4-(2-piperidin-1-yl-ethyl)-piperazin-1-yl]-methanone |
| II-183: | {4-[9-Chloro-7-(2,6-difluoro-phenyl)-5H-benzo[c]pyrimido[4,5-e]azepin-2-ylamino]-phenyl}-(4-dimethylamino-piperidin-1-yl)-methanone |
| II-184: | {4-[9-Chloro-7-(2,6-difluoro-phenyl)-5H-benzo[c]pyrimido[4,5-e]azepin-2-ylamino]-phenyl}-(4-methyl-piperazin-1-yl)-methanone |
| II-185: | 4-[9-Chloro-7-(2,6-difluoro-phenyl)-5H-benzo[c]pyrimido[4,5-e]azepin-2-ylamino]-N-(3-dimethylamino-propyl)-N-methyl-benzamide |
| II-186: | {4-[9-Chloro-7-(2-fluoro-6-methoxy-phenyl)-5H-benzo[c]pyrimido-[4,5-e]azepin-2-ylamino]-phenyl}-(4-dimethylamino-piperidin-1-yl)-methanone |
| II-187: | {4-[9-Chloro-7-(2-fluoro-phenyl)-5H-benzo[c]pyrimido[4,5-e]azepin-2-ylamino]-phenyl}-[4-(2-dipropylamino-ethyl)-piperazin-1-yl]-methanone |
| II-188: | {4-[9-Chloro-7-(2-fluoro-phenyl)-5H-benzo[c]pyrimido[4,5-e]azepin-2-ylamino]-phenyl}-[4-(3-pyrrolidin-1-yl-propyl)-piperazin-1-yl]-methanone |
| II-189: | {4-[9-Chloro-7-(2-fluoro-phenyl)-5H-benzo[c]pyrimido[4,5-e]azepin-2-ylamino]-phenyl}-[4-(2-morpholin-4-yl-ethyl)-piperazin-1-yl]-methanone |
| II-190: | 4-[9-Chloro-7-(2-fluoro-6-methoxy-phenyl)-5H-benzo[c]pyrimido[4,5-e]azepin-2-ylamino]-benzoic acid |
| II-191: | {4-[9-Chloro-7-(2,6-difluoro-phenyl)-5H-benzo[c]pyrimido[4,5-e]azepin-2-ylamino]-phenyl}-(3(S)-methyl-piperazin-1-yl)-methanone |
| II-192: | (3-Amino-azetidin-1-yl)-{4-[9-chloro-7-(2-fluoro-phenyl)-5H-benzo[c]pyrimido[4,5-e]azepin-2-ylamino]-phenyl}-methanone |
| II-193: | {4-[9-Chloro-7-(2-fluoro-phenyl)-5H-benzo[c]pyrimido[4,5-e]azepin-2-ylamino]-phenyl}-(3-dimethylaminomethyl-azetidin-1-yl)-methanone |
| II-194: | {4-[9-Chloro-7-(2,6-difluoro-phenyl)-5H-benzo[c]pyrimido[4,5-e]azepin-2-ylamino]-phenyl}-(3(R)-methyl-piperazin-1-yl)-methanone |
| II-195: | {4-[9-Chloro-7-(2,6-difluoro-phenyl)-5H-benzo[c]pyrimido[4,5-e]azepin-2-ylamino]-phenyl}-piperazin-1-yl-methanone |
| II-196: | (3-Amino-pyrrolidin-1-yl)-{4-[9-chloro-7-(2,6-difluoro-phenyl)-5H-benzo[c]pyrimido[4,5-e]azepin-2-ylamino]-phenyl}-methanone |
| II-197: | {4-[9-Chloro-7-(2,6-difluoro-phenyl)-5H-benzo[c]pyrimido[4,5-e]azepin-2-ylamino]-phenyl}-(3-methylamino-pyrrolidin-1-yl)-methanone |
| II-198: | 4-[9-Chloro-7-(2,6-difluoro-phenyl)-5H-benzo[c]pyrimido[4,5-e]azepin-2-ylamino]-N-methyl-N-(3-methylamino-propyl)-benzamide |
| II-199: | {4-[9-Chloro-7-(2-fluoro-6-methoxy-phenyl)-5H-benzo[c]pyrimido[4,5-e]azepin-2-ylamino]-phenyl}-(3-methylamino-pyrrolidin-1-yl)-methanone |
| II-200: | 4-[9-Chloro-7-(2-fluoro-phenyl)-5H-benzo[c]pyrimido[4,5-e]azepin-2-ylamino]-cyclohexanecarboxylic acid |
| II-201: | 9-chloro-N-(4-{[4-(2-ethoxyphenyl)piperazin-1-yl]carbonyl}phenyl)-7-(2-fluorophenyl)-5H-pyrimido[5,4-d][2]benzazepin-2-amine |
| II-202: | N-[amino(imino)methyl]-4-{[9-chloro-7-(2,6-difluorophenyl)-5H-pyrimido[5,4-d][2]benzazepin-2-yl]amino}benzamide |
| II-203: | 3-{[9-chloro-7-(2,6-difluorophenyl)-5H-pyrimido[5,4-d][2]benzazepin-2-yl]amino}benzoic acid |
| II-204: | 9-chloro-7-(2,6-difluorophenyl)-N-(3-{[3-(dimethylamino)azetidin-1-yl]carbonyl}phenyl)-5H-pyrimido[5,4-d][2]benzazepin-2-amine |
| II-205: | 9-chloro-7-(2,6-difluorophenyl)-N-(3-{[4-(dimethylamino)piperidin-1-yl]carbonyl}phenyl)-5H-pyrimido[5,4-d][2]benzazepin-2-amine |
| II-206: | 9-chloro-7-(2,6-difluorophenyl)-N-(3-{[3-(dimethylamino)pyrrolidin-1-yl]carbonyl}phenyl)-5H-pyrimido[5,4-d][2]benzazepin-2-amine |
| II-207: | N-[2-(aminomethyl)-1,3-benzoxazol-5-yl]-9-chloro-7-(2,6-difluorophenyl)-5H-pyrimido[5,4-d][2]benzazepin-2-amine |
| II-208: | 9-chloro-N-[4-({4-[3-(diethylamino)propyl]piperazin-1-yl}carbonyl)phenyl]-7-(2-fluorophenyl)-5H-pyrimido[5,4-d][2]benzazepin-2-amine |
| II-209: | 9-chloro-N-[4-({4-[2-(diethylamino)ethyl]piperazin-1-yl}carbonyl)phenyl]-7-(2-fluorophenyl)-5H-pyrimido[5,4-d][2]benzazepin-2-amine |
| II-210: | 9-chloro-N-[4-({4-[3-(dimethylamino)propyl]piperazin-1-yl}carbonyl)phenyl]-7-(2-fluorophenyl)-5H-pyrimido[5,4-d][2]benzazepin-2-amine |
| II-211: | 9-chloro-7-(2-fluorophenyl)-N-[4-({4-[(1-methylpiperidin-3-yl)methyl]piperazin-1-yl}carbonyl)phenyl]-5H-pyrimido[5,4-d][2]benzazepin-2-amine |
| II-212: | 9-chloro-7-{2,6-difluorophenyl)-N-(4-nitrophenyl)-5H-pyrimido[5,4-d][2]benzazepin-2-amine |
| II-213: | 9-chloro-N-(3-chloro-4-{[4-(2-pyrrolidin-1-ylethyl)piperazin-1-yl]carbonyl}phenyl)-7-(2-fluorophenyl)-5H-pyrimido[5,4-d][2]benzazepin-2-amine |

TABLE 1-continued

Examples of Compounds of Formula (II)

| | |
|---|---|
| II-214: | 9-chloro-N-{3-chloro-4-[(3-methylpiperazin-1-yl)carbonyl]phenyl}-7-(2-fluorophenyl)-5H-pyrimido[5,4-d][2]benzazepin-2-amine |
| II-215: | 9-chloro-N-(3-chloro-4-{[3-(dimethylamino)pyrrolidin-1-yl]carbonyl}phenyl)-7-(2,6-difluorophenyl)-5H-pyrimido[5,4-d][2]benzazepin-2-amine |
| II-216: | 9-chloro-N-{3-chloro-4-[(3-methylpiperazin-1-yl)carbonyl]phenyl}-7-(2,6-difluorophenyl)-5H-pyrimido[5,4-d][2]benzazepin-2-amine |
| II-217: | N-[9-chloro-7-(2,6-difluorophenyl)-5H-pyrimido[5,4-d][2]benzazepin-2-yl]benzene-1,4-diamine |
| II-218: | methyl 2-chloro-4-{[9-chloro-7-(2,6-difluorophenyl)-5H-pyrimido[5,4-d][2]benzazepin-2-yl]amino}benzoate |
| II-219: | 1-(4-{[9-chloro-7-(2,6-difluorophenyl)-5H-pyrimido[5,4-d][2]benzazepin-2-yl]amino}benzoyl)piperazine-2-carboxylic acid |
| II-220: | 9-chloro-7-(2,6-difluorophenyl)-N-(4-{[4-(methylamino)piperidin-1-yl]carbonyl}phenyl)-5H-pyrimido[5,4-d][2]benzazepin-2-amine |
| II-221: | N-{4-[(3-aminopiperidin-1-yl)carbonyl]phenyl}-9-chloro-7-(2,6-difluorophenyl)-5H-pyrimido[5,4-d][2]benzazepin-2-amine |
| II-222: | 9-chloro-7-(2,6-difluorophenyl)-N-{3-[(3,5-dimethylpiperazin-1-yl)carbonyl]phenyl}-5H-pyrimido[5,4-d][2]benzazepin-2-amine |
| II-223: | 4-{[9-chloro-7-(2,6-difluorophenyl)-5H-pyrimido[5,4-d][2]benzazepin-2-yl]amino}-N-[[4-{dimethylamino)piperidin-1-yl](imino)methyl]benzamide |
| II-224: | 4-{[9-chloro-7-(2,6-difluorophenyl)-5H-pyrimido[5,4-d][2]benzazepin-2-yl]amino}-N-[imino(piperazin-1-yl)methyl]benzamide |
| II-225: | 4-{[9-chloro-7-(2-fluoro-6-methoxyphenyl)-5H-pyrimido[5,4-d][2]benzazepin-2-yl]amino}-N-[3-(dimethylamino)propyl]-N-methylbenzamide |
| II-226: | 3-{[9-Chloro-7-(2-fluoro-6-methoxyphenyl)-5H-pyrimido[5,4-d][2]benzazepin-2-yl]amino}-N-[3-(dimethylamino)propyl]-N-methylbenzamide |
| II-227: | 9-chloro-N-(3-{[3-{dimethylamino}azetidin-1-yl]carbonyl}phenyl)-7-{2-fluoro-6-methoxyphenyl}-5H-pyrimido[5,4-d][2]benzazepin-2-amine |
| II-228: | 9-chloro-N-{3-[(3,5-dimethylpiperazin-1-yl)carbonyl]phenyl}-7-(2-fluoro-6-methoxyphenyl)-5H-pyrimido[5,4-d][2]benzazepin-2-amine |
| II-229: | 9-chloro-N-(3-{[4-(dimethylamino)piperidin-1-yl]carbonyl}phenyl)-7-(2-fluoro-6-methoxyphenyl)-5H-pyrimido[5,4-d][2]benzazepin-2-amine |
| II-230: | N-(4-{[3-(aminomethyl)azetidin-1-yl]carbonyl}phenyl)-9-chloro-7-(2-fluorophenyl)-5H-pyrimido[5,4-d][2]benzazepin-2-amine |
| II-231: | 9-chloro-N-(3-{[3-(dimethylamino)pyrrolidin-1-yl]carbonyl}phenyl)-7-(2-fluoro-6-methoxyphenyl)-5H-pyrimido[5,4-d][2]benzazepin-2-amine |
| II-232: | 9-chloro-7-(2-fluoro-6-methoxyphenyl)-N-{4-[(3-methylpiperazin-1-yl)carbonyl]phenyl}-5H-pyrimido[5,4-d][2]benzazepin-2-amine |
| II-233: | 9-chloro-7-(2-fluoro-6-methoxyphenyl)-N-{4-[(4-methylpiperazin-1-yl)carbonyl]phenyl}-5H-pyrimido[5,4-d][2]benzazepin-2-amine |
| II-234: | 9-chloro-7-(2,6-difluorophenyl)-N-(4-{[3-(methylamino)azetidin-1-yl]carbonyl}phenyl)-5H-pyrimido[5,4-d][2]benzazepin-2-amine |
| II-235: | 9-chloro-7-(2-fluoro-6-methoxyphenyl)-N-(4-{[3-(methylamino)azetidin-1-yl]carbonyl}phenyl)-5H-pyrimido[5,4-d][2]benzazepin-2-amine |
| II-236: | 4-{[9-chloro-7-(2,6-difluorophenyl)-5H-pyrimido[5,4-d][2]benzazepin-2-yl]amino}benzonitrile |
| II-237: | 4-{[9-chloro-7-(2,6-difluorophenyl)-5H-pyrimido[5,4-d][2]benzazepin-2-yl]amino}-N-[[3-(dimethylamino)pyrrolidin-1-yl](imino)methyl]benzamide |
| II-238: | 4-{[9-chloro-7-(2,6-difluorophenyl)-5H-pyrimido[5,4-d][2]benzazepin-2-yl]amino}-N-[(3,5-dimethylpiperazin-1-yl)(imino)methyl]benzamide |
| II-239: | N-{4-[(4-aminopiperidin-1-yl)carbonyl]phenyl}-9-chloro-7-(2,6-difluorophenyl)-5H-pyrimido[5,4-d][2]benzazepin-2-amine |
| II-240: | N-{4-[(3-aminopyrrolidin-1-yl)carbonyl]phenyl}-9-chloro-7-(2-fluoro-6-methoxyphenyl)-5H-pyrimido[5,4-d][2]benzazepin-2-amine |
| II-241: | N-{4-[(4-aminopiperidin-1-yl)carbonyl]phenyl}-9-chloro-7-(2-fluoro-6-methoxyphenyl)-5H-pyrimido[5,4-d][2]benzazepin-2-amine |
| II-242: | 9-chloro-7-(2-fluoro-6-methoxyphenyl)-N-(4-{[4-(methylamino)piperidin-1-yl]carbonyl}phenyl)-5H-pyrimido[5,4-d][2]benzazepin-2-amine |
| II-243: | 9-chloro-7-(2-fluoro-6-methoxyphenyl)-N-[4-(piperazin-1-ylcarbonyl)phenyl]-5H-pyrimido[5,4-d][2]benzazepin-2-amine |
| II-244: | 9-chloro-7-(2,6-difluorophenyl)-N-{4-[[4-(dimethylamino)piperidin-1-yl](imino)methyl]phenyl}-5H-pyrimido[5,4-d][2]benzazepin-2-amine |
| II-245: | N-(4-{[9-chloro-7-(2,6-difluorophenyl)-5H-pyrimido[5,4-d][2]benzazepin-2-yl]amino}phenyl)guanidine |
| II-246: | 4-{[9-chloro-7-(2,6-difluorophenyl)-5H-pyrimido[5,4-d][2]benzazepin-2-yl]amino}-N-methyl-N-[2-(methylamino)ethyl]benzamide |
| II-247: | 4-{[9-chloro-7-(2,6-difluorophenyl)-5H-pyrimido[5,4-d][2]benzazepin-2-yl]amino}-N-[2-(dimethylamino)ethyl]-N-methylbenzamide |
| II-248: | methyl 4-(4-{[9-chloro-7-(2,6-difluorophenyl)-5H-pyrimido[5,4-d][2]benzazepin-2-yl]amino}benzoyl)piperazine-2-carboxylate |
| II-249: | 2-[(4-carboxyphenyl)amino]-7-(2-fluorophenyl)-5H-pyrimido[5,4-d][2]benzazepine-9-carboxylic acid |

TABLE 1-continued

Examples of Compounds of Formula (II)

| | |
|---|---|
| II-250: | 9-chloro-7-(2,6-difluorophenyl)-N-{4-[[3-(dimethylamino)pyrrolidin-1-yl](imino)methyl]phenyl}-5H-pyrimido[5,4-d][2]benzazepin-2-amine |
| II-251: | 9-chloro-7-(2,6-difluorophenyl)-N-{4-[(3,5-dimethylpiperazin-1-yl)(imino)methyl]phenyl}-5H-pyrimido[5,4-d][2]benzazepin-2-amine |
| II-252: | N-(2-aminoethyl)-4-{[9-chloro-7-(2,6-difluorophenyl)-5H-pyrimido[5,4-d][2]benzazepin-2-yl]amino}-N-methylbenzamide |
| II-253: | 9-chloro-7-(2,6-difluorophenyl)-N-(4-{[3-(methylamino)piperidin-1-yl]carbonyl}phenyl)-5H-pyrimido[5,4-d][2]benzazepin-2-amine |
| II-254: | 4-{[9-chloro-7-(2-fluoro-6-methoxyphenyl)-5H-pyrimido[5,4-d][2]benzazepin-2-yl]amino}-N-methyl-N-[2-(methylamino)ethyl]benzamide |
| II-255: | 4-{[9-chloro-7-(2-fluoro-6-methoxyphenyl)-5H-pyrimido[5,4-d][2]benzazepin-2-yl]amino}-N-[2-(dimethylamino)ethyl]-N-methylbenzamide |
| II-256: | 7-(2-fluorophenyl)-2-[(3-methoxyphenyl)amino]-5H-pyrimido[5,4-d][2]benzazepine-9-carboxylic acid |
| II-257: | N-(3-aminopropyl)-4-{[9-chloro-7-(2,6-difluorophenyl)-5H-pyrimido[5,4-d][2]benzazepin-2-yl]amino}-N-methylbenzamide |
| II-258: | 2-chloro-5-{[9-chloro-7-(2,6-difluorophenyl)-5H-pyrimido[5,4-d][2]benzazepin-2-yl]amino}benzoic acid |
| II-259: | 4-{[9-chloro-7-(2,6-difluorophenyl)-5H-pyrimido[5,4-d][2]benzazepin-2-yl]amino}-N-[[3-(dimethylamino)azetidin-1-yl](imino)methyl]benzamide |
| II-260: | N-(2-amino-2-methylpropyl)-4-{[9-chloro-7-(2,6-difluorophenyl)-5H-pyrimido[5,4-d][2]benzazepin-2-yl]amino}benzamide |
| II-261: | 4-{[9-chloro-7-(2-fluoro-6-methoxyphenyl)-5H-pyrimido[5,4-d][2]benzazepin-2-yl]amino}-N-methyl-N-[3-(methylamino)propyl]benzamide |
| II-262: | N-{4-[(3-aminopiperidin-1-yl)carbonyl]phenyl}-9-chloro-7-(2-fluoro-6-methoxyphenyl)-5H-pyrimido[5,4-d][2]benzazepin-2-amine |
| II-263: | 9-chloro-7-(2-fluoro-6-methoxyphenyl)-N-{4-{[3-(methylamino)piperidin-1-yl]carbonyl}phenyl)-5H-pyrimido[5,4-d][2]benzazepin-2-amine |
| II-264: | N-(3-aminopropyl)-4-{[9-chloro-7-(2-fluoro-6-methoxyphenyl)-5H-pyrimido[5,4-d][2]benzazepin-2-ylamino}-N-methylbenzamide |
| II-265: | N-(2-aminoethyl)-4-{[9-chloro-7-(2-fluoro-6-methoxyphenyl)-5H-pyrimido[5,4-d][2]benzazepin-2-yl]amino}-N-methylbenzamide |
| II-266: | 4-(4-{[9-chloro-7-(2,6-difluorophenyl)-5H-pyrimido[5,4-d][2]benzazepin-2-yl]amino}benzoyl)piperazine-2-carboxylic acid |
| II-267: | 9-chloro-7-(2,6-difluorophenyl)-N-{4-[[3-(dimethylamino)azetidin-1-yl](imino)methyl]phenyl}-5H-pyrimido[5,4-d][2]benzazepin-2-amine |
| II-268: | 9-chloro-7-(2,6-difluorophenyl)-N-(4-{imino[3-(methylamino)pyrrolidin-1-yl]methyl}phenyl)-5H-pyrimido[5,4-d][2]benzazepin-2-amine |
| II-269: | 9-chloro-N-(4-chloro-3-{[4-(dimethylamino)piperidin-1-yl]carbonyl}phenyl)-7-(2,6-difluorophenyl)-5H-pyrimido[5,4-d][2]benzazepin-2-amine |
| II-270: | 9-chloro-7-(2,6-difluorophenyl)-N-[4-(5,5-dimethyl-4,5-dihydro-1H-imidazol-2-yl)phenyl]-5H-pyrimido[5,4-d][2]benzazepin-2-amine |
| II-271: | N-[9-chloro-7-(2,6-difluorophenyl)-5H-pyrimido[5,4-d][2]benzazepin-2-yl]-N'-pyrimidin-2-ylbenzene-1,4-diamine |
| II-272: | 4-{[9-(3-aminoprop-1-yn-1-yl)-7-(2,6-difluorophenyl)-5H-pyrimido[5,4-d][2]benzazepin-2-yl]amino}benzoic acid |
| II-273: | 9-bromo-7-(2,6-difluorophenyl)-N-(3-methoxyphenyl)-5H-pyrimido[5,4-d][2]benzazepin-2-amine |
| II-274: | 4-{[9-bromo-7-(2,6-difluorophenyl)-5H-pyrimido[5,4-d][2]benzazepin-2-yl]amino}benzoic acid |
| II-275: | 7-(2,6-difluorophenyl)-N-(3-methoxyphenyl)-9-(3-pyrrolidin-1-ylprop-1-yn-1-yl)-5H-pyrimido[5,4-d][2]benzazepin-2-amine |
| II-276: | 9-(3-aminoprop-1-yn-1-yl)-7-(2,6-difluorophenyl)-N-(3-methoxyphenyl)-5H-pyrimido[5,4-d][2]benzazepin-2-amine |
| II-277: | 4-({9-chloro-7-[2-(trifluoromethyl)phenyl]-5H-pyrimido[5,4-d][2]benzazepin-2-yl}amino)benzoic acid |
| II-278: | N-{4-[(3-aminoazetidin-1-yl)carbonyl]phenyl}-9-chloro-7-(2,6-difluorophenyl)-5H-pyrimido[5,4-d][2]benzazepin-2-amine |
| II-279: | 4-[(9-chloro-7-pyridin-2-yl-5H-pyrimido[5,4-d][2]benzazepin-2-yl)amino]benzoic acid |
| II-280: | N-(4-{[9-chloro-7-(2,6-difluorophenyl)-5H-pyrimido[5,4-d][2]benzazepin-2-yl]amino}phenyl)-4-methylpiperazine-1-carboxamide |
| II-281: | 9-chloro-N-(4-chloro-3-{[3-(methylamino)pyrrolidin-1-yl]carbonyl}phenyl)-7-(2,6-difluorophenyl)-5H-pyrimido[5,4-d][2]benzazepin-2-amine |
| II-282: | 9-chloro-N-(4-chloro-3-{[4-(methylamino)piperidin-1-yl]carbonyl}phenyl)-7-(2,6-difluorophenyl)-5H-pyrimido[5,4-d][2]benzazepin-2-amine |
| II-283: | 2-chloro-5-{[9-chloro-7-(2,6-difluorophenyl)-5H-pyrimido[5,4-d][2]benzazepin-2-yl]amino}-N-methyl-N-[2-(methylamino)ethyl]benzamide |
| II-284: | N-{4-[(3-aminopyrrolidin-1-yl)(imino)methyl]phenyl}-9-chloro-7-(2,6-difluorophenyl)-5H-pyrimido[5,4-d][2]benzazepin-2-amine |

TABLE 1-continued

Examples of Compounds of Formula (II)

| | |
|---|---|
| II-285: | 2-(4-{[9-chloro-7-(2,6-difluorophenyl)-5H-pyrimido[5,4-d][2]benzazepin-2-yl]amino}phenyl)-1,4,5,6-tetrahydropyrimidin-5-ol |
| II-286: | N-{4-[(3-aminoazetidin-1-yl)carbonyl]phenyl}-9-chloro-7-(2-fluoro-6-methoxyphenyl)-5H-pyrimido[5,4-d][2]benzazepin-2-amine |
| II-287: | N-{4-[(4-aminopiperidin-1-yl)carbonyl]phenyl}-9-chloro-7-[2-(trifluoromethyl)phenyl]-5H-pyrimido[5,4-d][2]benzazepin-2-amine |
| II-288: | 9-chloro-N-(4-{[4-(methylamino)piperidin-1-yl]carbonyl}phenyl)-7-[2-(trifluoromethyl)phenyl]-5H-pyrimido[5,4-d][2]benzazepin-2-amine |
| II-289: | N-{4-[(3-aminopyrrolidin-1-yl)carbonyl]phenyl}-9-chloro-7-[2-(trifluoromethyl)phenyl]-5H-pyrimido[5,4-d][2]benzazepin-2-amine |
| II-290: | 9-chloro-N-(4-{[3-(methylamino)pyrrolidin-1-yl]carbonyl}phenyl)-7-[2-(trifluoromethyl)phenyl]-5H-pyrimido[5,4-d][2]benzazepin-2-amine |
| II-291: | 9-chloro-N-(4-chloro-3-{[3-(methylamino)azetidin-1-yl]carbonyl}phenyl)-7-(2,6-difluorophenyl)-5H-pyrimido[5,4-d][2]benzazepin-2-amine |
| II-292: | N-{3-[(4-aminopiperidin-1-yl)carbonyl]-4-chlorophenyl}-9-chloro-7-(2,6-difluorophenyl)-5H-pyrimido[5,4-d][2]benzazepin-2-amine |
| II-293: | 9-Chloro-7-(2,6-difluorophenyl)-N-(4-{[3-(dimethylamino)piperidin-1-yl]carbonyl}phenyl)-5H-pyrimido[5,4-d][2]benzazepin-2-amine |
| II-294: | methyl 4-amino-1-(4-{[9-chloro-7-(2,6-difluorophenyl)-5H-pyrimido[5,4-d][2]benzazepin-2-yl]amino}benzoyl)piperidine-4-carboxylate |
| II-295: | 4-amino-1-(4-{[9-chloro-7-(2,6-difluorophenyl)-5H-pyrimido[5,4-d][2]benzazepin-2-yl]amino}benzoyl)piperidine-4-carboxylic acid |
| II-296: | N-{4-[(3-aminoazetidin-1-yl)carbonyl]phenyl}-9-chloro-7-[2-(trifluoromethyl)phenyl]-5H-pyrimido[5,4-d][2]benzazepin-2-amine |
| II-297: | 9-chloro-N-(4-{[3-(methylamino)azetidin-1-yl]carbonyl}phenyl)-7-[2-(trifluoromethyl)phenyl]-5H-pyrimido[5,4-d][2]benzazepin-2-amine |
| II-298: | N-{4-[(4-aminopiperidin-1-yl)carbonyl]phenyl}-9-chloro-7-pyridin-2-yl-5H-pyrimido[5,4-d][2]benzazepin-2-amine |
| II-299: | N-{4-[(3-aminopyrrolidin-1-yl)carbonyl]phenyl}-9-chloro-7-pyridin-2-yl-5H-pyrimido[5,4-d][2]benzazepin-2-amine |
| II-300: | ethyl 2-amino-4-[(4-{[9-chloro-7-(2,6-difluorophenyl)-5H-pyrimido[5,4-d][2]benzazepin-2-yl]amino}benzoyl)amino]butanoate |
| II-301: | 4-{[9-chloro-7-(3-fluoropyridin-2-yl)-5H-pyrimido[5,4-d][2]benzazepin-2-yl]amino}benzoic acid |
| II-302: | 9-{[3-(dimethylamino)azetidin-1-yl]carbonyl}-7-(2-fluorophenyl)-N-(3-methoxyphenyl)-5H-pyrimido[5,4-d][2]benzazepin-2-amine |
| II-303: | 7-(2-fluorophenyl)-2-[(3-methoxyphenyl)amino]-N-methyl-N-[3-(methylamino)propyl]-5H-pyrimido[5,4-d][2]benzazepine-9-carboxamide |
| II-304: | N-{4-[(4-aminopiperidin-1-yl)carbonyl]phenyl}-9-chloro-7-(3-fluoropyridin-2-yl)-5H-pyrimido[5,4-d][2]benzazepin-2-amine |
| II-305: | N-{4-[(3-aminopyrrolidin-1-yl)carbonyl]phenyl}-9-chloro-7-(3-fluoropyridin-2-yl)-5H-pyrimido[5,4-d][2]benzazepin-2-amine |
| II-306: | 2-{4-{[9-chloro-7-(2,6-difluorophenyl)-5H-pyrimido[5,4-d][2]benzazepin-2-yl]amino}phenyl)-4,5-dihydro-1H-imidazole-5-carboxylic acid |
| II-307: | N-(4-{[9-chloro-7-(2,6-difluorophenyl)-5H-pyrimido[5,4-d][2]benzazepin-2-yl]amino}phenyl)-2-(dimethylamino)acetamide |
| II-308: | 2-amino-N-(4-{[9-chloro-7-(2,6-difluorophenyl)-5H-pyrimido[5,4-d][2]benzazepin-2-yl]amino}phenyl)-2-methylpropanamide |
| II-309: | ethyl (2R)-4-amino-2-[(4-{[9-chloro-7-(2,6-difluorophenyl)-5H-pyrimido[5,4-d][2]benzazepin-2-yl]amino}benzoyl)amino]butanoate |
| II-310: | 4-(4-{[9-chloro-7-(2,6-difluorophenyl)-5H-pyrimido[5,4-d][2]benzazepin-2-yl]amino}benzoyl)-N-methylpiperazine-2-carboxamide |
| II-311: | 7-(2-fluorophenyl)-2-[(3-methoxyphenyl)amino]-N-(3-morpholin-4-ylpropyl)-5H-pyrimido[5,4-d][2]benzazepine-9-carboxamide |
| II-312: | 9-[(3,5-dimethylpiperazin-1-yl)carbonyl]-7-(2-fluorophenyl)-N-(3-methoxyphenyl)-5H-pyrimido[5,4-d][2]benzazepin-2-amine |
| II-313: | 9-chloro-N-(3-chloro-4-{[4-(dimethylamino)piperidin-1-yl]carbonyl}phenyl)-7-(2,6-difluorophenyl)-5H-pyrimido[5,4-d][2]benzazepin-2-amine |
| II-314: | ethyl 2-(4-{[9-chloro-7-(2,6-difluorophenyl)-5H-pyrimido[5,4-d][2]benzazepin-2-yl]amino}phenyl)-4,5-dihydro-1H-imidazole-5-carboxylate |
| II-315: | 9-chloro-N-(4-{[3-(methylamino)pyrrolidin-1-yl]carbonyl}phenyl)-7-pyridin-2-yl-5H-pyrimido[5,4-d][2]benzazepin-2-amine |
| II-316: | 9-chloro-N-(4-{[4-(methylamino)piperidin-1-yl]carbonyl}phenyl)-7-pyridin-2-yl-5H-pyrimido[5,4-d][2]benzazepin-2-amine |
| II-317: | 4-(4-{[9-chloro-7-(2,6-difluorophenyl)-5H-pyrimido[5,4-d][2]benzazepin-2-yl]amino}benzoyl)piperazine-2-carboxamide |
| II-318: | N-{4-[(3-aminopyrrolidin-1-yl)carbonyl]-3-chlorophenyl}-9-chloro-7-(2,6-difluorophenyl)-5H-pyrimido[5,4-d][2]benzazepin-2-amine |
| II-319: | N-(4-{[9-chloro-7-(2,6-difluorophenyl)-5H-pyrimido[5,4-d][2]benzazepin-2-yl]amino}phenyl)piperidine-4-carboxamide |
| II-320: | 4-{[9-chloro-7-(2-fluoro-6-{methyl[2-(methylamino)ethyl]amino}phenyl)-5H-pyrimido[5,4-d][2]benzazepin-2-yl]amino}benzoic acid |
| II-321: | 9-chloro-7-(2,4-difluorophenyl)-N-{4-[(3,5-dimethylpiperazin-1-yl)carbonyl]phenyl}-5H-pyrimido[5,4-d][2]benzazepin-2-amine |
| II-322: | 9-chloro-7-(2,4-dimethoxyphenyl)-N-{4-[(3,5-dimethylpiperazin-1-yl)carbonyl]phenyl}-5H-pyrimido[5,4-d][2]benzazepin-2-amine |

TABLE 1-continued

Examples of Compounds of Formula (II)

II-323: 9-chloro-7-(2-chloro-6-fluorophenyl)-N-{4-[(3-methylpiperazin-1-yl)carbonyl]phenyl}-5H-pyrimido[5,4-d][2]benzazepin-2-amine
II-324: 9-chloro-7-(2-chloro-6-fluorophenyl)-N-{4-[(3,5-dimethylpiperazin-1-yl)carbonyl]phenyl}-5H-pyrimido[5,4-d][2]benzazepin-2-amine
II-325: 9-chloro-7-(2-chloro-6-fluorophenyl)-N-(4-{[4-(methylamino)piperidin-1-yl]carbonyl}phenyl)-5H-pyrimido[5,4-d][2]benzazepin-2-amine
II-326: 9-chloro-7-(2-chloro-6-fluorophenyl)-N-(4-{[3-(methylamino)piperidin-1-yl]carbonyl}phenyl)-5H-pyrimido[5,4-d][2]benzazepin-2-amine
II-327: 9-chloro-7-(2-chloro-6-fluorophenyl)-N-(4-{[3-(methylamino)pyrrolidin-1-yl]carbonyl}phenyl)-5H-pyrimido[5,4-d][2]benzazepin-2-amine
II-328: 9-chloro-N-(3,4-dimethoxyphenyl)-7-{2-[(dimethylamino)methyl]phenyl}-5H-pyrimido[5,4-d][2]benzazepin-2-amine
II-329: 9-chloro-7-(2-methoxyphenyl)-N-{4-[(3-methylpiperazin-1-yl)carbonyl]phenyl}-5H-pyrimido[5,4-d][2]benzazepin-2-amine
II-330: 9-chloro-N-{4-[(3,5-dimethylpiperazin-1-yl)carbonyl]phenyl}-7-(2-methoxyphenyl)-5H-pyrimido[5,4-d][2]benzazepin-2-amine
II-331: 9-chloro-7-(2-methoxyphenyl)-N-(4-{[4-(methylamino)piperidin-1-yl]carbonyl}phenyl)-5H-pyrimido[5,4-d][2]benzazepin-2-amine
II-332: 9-chloro-7-(2-methoxyphenyl)-N-(4-{[3-(methylamino)pyrrolidin-1-yl]carbonyl}phenyl)-5H-pyrimido[5,4-d][2]benzazepin-2-amine
II-333: 9-chloro-7-(2-methoxyphenyl)-N-(4-{[3-(methylamino)piperidin-1-yl]carbonyl}phenyl)-5H-pyrimido[5,4-d][2]benzazepin-2-amine
II-334: 4-{[9-chloro-7-(2,6-difluorophenyl)-5H-pyrimido[5,4-d][2]benzazepin-2-yl]amino}-N-methylbenzamide
II-335: 4-{[9-chloro-7-(2-fluoro-6-{methyl[3-(methylamino)propyl]amino}phenyl)-5H-pyrimido[5,4-d][2]benzazepin-2-yl]amino}benzoic acid
II-336: 4-{[9-chloro-7-(2-fluoro-6-{methyl[3-(methylamino)propyl]amino}phenyl)-5H-pyrimido[5,4-d][2]benzazepin-2-yl]amino}-N-methylbenzamide
II-337: 1-(4-{[9-chloro-7-(2,6-difluorophenyl)-5H-pyrimido[5,4-d][2]benzazepin-2-yl]amino}phenyl)ethanone
II-338: N-[3-(3-aminoprop-1-yn-1-yl)phenyl]-9-chloro-7-(2,6-difluorophenyl)-5H-pyrimido[5,4-d][2]benzazepin-2-amine
II-339: 4-[(9-chloro-7-{2-fluoro-6-[(2-hydroxyethyl)amino]phenyl}-5H-pyrimido[5,4-d][2]benzazepin-2-yl)amino]-N-methylbenzamide
II-340: 4-[(7-{2-[(2-aminoethyl)amino]-6-fluorophenyl}-9-chloro-5H-pyrimido[5,4-d][2]benzazepin-2-yl)amino]-N-methylbenzamide
II-341: 4-amino-1-(4-{[9-chloro-7-(2,6-difluorophenyl)-5H-pyrimido[5,4-d][2]benzazepin-2-yl]amino}benzoyl)-N-methylpiperidine-4-carboxamide
II-342: 4-[(9-chloro-7-{2-[4-(dimethylamino)piperidin-1-yl]-6-fluorophenyl}-5H-pyrimido[5,4-d][2]benzazepin-2-yl)amino]-N-methylbenzamide
II-343: 9-chloro-7-(2,6-difluorophenyl)-N-{3-[3-(dimethylamino)prop-1-yn-1-yl]phenyl}-5H-pyrimido[5,4-d][2]benzazepin-2-amine
II-344: 9-chloro-7-(2,6-difluorophenyl)-N-(3-iodophenyl)-5H-pyrimido[5,4-d][2]benzazepin-2-amine
II-345: 4-{[9-chloro-7-(2-{[2-(dimethylamino)ethyl]amino}-6-fluorophenyl)-5H-pyrimido[5,4-d][2]benzazepin-2-yl]amino}-N-methylbenzamide
II-346: 4-[(9-chloro-7-{2-[[2-(dimethylamino)ethyl](methyl)amino]-6-fluorophenyl}-5H-pyrimido[5,4-d][2]benzazepin-2-yl)amino]-N-methylbenzamide
II-347: 4-{[9-chloro-7-(2-fluoro-6-{methyl[2-(methylamino)ethyl]amino}phenyl)-5H-pyrimido[5,4-d][2]benzazepin-2-yl]amino}-N-methylbenzamide
II-348: 4-({7-[2-(4-aminopiperidin-1-yl)-6-fluorophenyl]-9-chloro-5H-pyrimido[5,4-d][2]benzazepin-2-yl}amino)-N-methylbenzamide
II-349: 7-(2-fluorophenyl)-2-[(3-methoxyphenyl)amino]-N-methyl-N-[2-(methylamino)ethyl]-5H-pyrimido[5,4-d][2]benzazepine-9-carboxamide
II-350: 4-amino-1-(4-{[9-chloro-7-(2,6-difluorophenyl)-5H-pyrimido[5,4-d][2]benzazepin-2-yl]amino}benzoyl)piperidine-4-carboxamide
II-351: 9-chloro-7-(2-chloro-6-fluorophenyl)-N-(4-{[3-(methylamino)azetidin-1-yl]carbonyl}phenyl)-5H-pyrimido[5,4-d][2]benzazepin-2-amine
II-352: 9-chloro-7-(2,6-difluorophenyl)-N-(4-methyl-1,3-thiazol-2-yl)-5H-pyrimido[5,4-d][2]benzazepin-2-amine
II-353: 7-(2,6-difluorophenyl)-2-[(3-methoxyphenyl)amino]-5H-pyrimido[5,4-d][2]benzazepine-9-carboxylic acid
II-354: 4-({9-chloro-7-[2-fluoro-6-(methylamino)phenyl]-5H-pyrimido[5,4-d][2]benzazepin-2-yl}amino)-N-methylbenzamide
II-355: 2-{[9-chloro-7-(2,6-difluorophenyl)-5H-pyrimido[5,4-d][2]benzazepin-2-yl]amino}-N-methyl-1,3-thiazole-4-carboxamide
II-356: N-1H-benzimidazol-2-yl-9-chloro-7-(2,6-difluorophenyl)-5H-pyrimido[5,4-d][2]benzazepin-2-amine
II-357: 7-(2,6-difluorophenyl)-2-[(4-methyl-1,3-thiazol-2-yl)amino]-5H-pyrimido[5,4-d][2]benzazepine-9-carboxylic acid
II-358: 3-amino-1-(3-{[9-chloro-7-(2,6-difluorophenyl)-5H-pyrimido[5,4-d][2]benzazepin-2-yl]amino}phenyl)propan-1-one
II-359: 1-(3-{[9-chloro-7-(2,6-difluorophenyl)-5H-pyrimido[5,4-d][2]benzazepin-2-yl]amino}phenyl)-3-(dimethylamino)propan-1-one TABLE 1-continued Examples of Compounds of Formula (II)

| | |
|---|---|
| II-360: | 2-{[9-chloro-7-(2,6-difluorophenyl)-5H-pyrimido[5,4-d][2]benzazepin-2-yl]amino}-1,3-thiazole-4-carboxylic acid |
| II-361: | ethyl 2-{[9-chloro-7-(2,6-difluorophenyl)-5H-pyrimido[5,4-d][2]benzazepin-2-yl]amino}-1,3-thiazole-4-carboxylate |
| II-362: | 9-chloro-7-(2,6-difluorophenyl)-N-{4-[(3,5-dimethylpiperazin-1-yl)carbonyl]-1,3-thiazol-2-yl}-5H-pyrimido[5,4-d][2]benzazepin-2-amine |
| II-363: | ethyl 2-{[9-chloro-7-(2,6-difluorophenyl)-5H-pyrimido[5,4-d][2]benzazepin-2-yl]amino}-1,3-oxazole-5-carboxylate |
| II-364: | 2-{[9-chloro-7-(2,6-difluorophenyl)-5H-pyrimido[5,4-d][2]benzazepin-2-yl]amino}-1,3-oxazole-5-carboxylic acid |
| II-365: | 9-chloro-7-(2,6-difluorophenyl)-N-(4-{[(3R)-3-methylpiperazin-1-yl]carbonyl}-1,3-thiazol-2-yl)-5H-pyrimido[5,4-d][2]benzazepin-2-amine |
| II-366: | 9-chloro-7-(2,6-difluorophenyl)-N-(4-{[(2R)-2-methylpiperazin-1-yl]carbonyl}phenyl)-5H-pyrimido[5,4-d][2]benzazepin-2-amine |
| II-367: | 9-chloro-7-{2,6-difluorophenyl)-N-(4-{[3-(methylamino)pyrrolidin-1-yl]carbonyl}-1,3-thiazol-2-yl)-5H-pyrimido[5,4-d][2]benzazepin-2-amine |
| II-368: | 2-{[9-chloro-7-(2,6-difluorophenyl)-5H-pyrimido[5,4-d][2]benzazepin-2-yl]amino}-1,3-oxazole-4-carboxylic acid |
| II-369: | 9-chloro-7-(2,6-difluorophenyl)-N-{5-[(3,5-dimethylpiperazin-1-yl)carbonyl]-1,3-oxazol-2-yl}-5H-pyrimido[5,4-d][2]benzazepin-2-amine |
| II-370: | 9-chloro-7-(2,6-difluorophenyl)-N-(5-{[3-(methylamino)pyrrolidin-1-yl]carbonyl}-1,3-oxazol-2-yl)-5H-pyrimido[5,4-d][2]benzazepin-2-amine |
| II-371: | 4-{[9-chloro-7-(2,6-difluorophenyl)-5-methyl-5H-pyrimido[5,4-d][2]benzazepin-2-yl]amino}benzoic acid |
| II-372: | 9-chloro-7-(2,6-difluorophenyl)-N-{3-[3-(dimethylamino)propyl]phenyl}-5H-pyrimido[5,4-d][2]benzazepin-2-amine |
| II-373: | N-[3-(3-aminopropyl)phenyl]-9-chloro-7-(2,6-difluorophenyl)-5H-pyrimido[5,4-d][2]benzazepin-2-amine |
| II-374: | 9-chloro-7-(2,6-difluorophenyl)-N-{4-[(3,5-dimethylpiperazin-1-yl)carbonyl]-1,3-oxazol-2-yl}-5H-pyrimido[5,4-d][2]benzazepin-2-amine |
| II-375: | 9-chloro-7-(2,6-difluorophenyl)-N-(4-{[3-(methylamino)pyrrolidin-1-yl]carbonyl}-1,3-oxazol-2-yl)-5H-pyrimido[5,4-d][2]benzazepin-2-amine |
| II-376: | 7-(2,6-difluorophenyl)-2-({4-[(3,5-dimethylpiperazin-1-yl)carbonyl]phenyl}amino)-N-methyl-5H-pyrimido[5,4-d][2]benzazepine-9-carboxamide |
| II-377: | 2-{[4-(aminocarbonyl)phenyl]amino}-7-(2,6-difluorophenyl)-5H-pyrimido[5,4-d][2]benzazepine-9-carboxylic acid |
| II-378: | 1-(4-{[9-chloro-7-(2,6-difluorophenyl)-5H-pyrimido[5,4d][2]benzazepin-2-yl]amino}benzoyl)-N-methyl-4-(methylamino)piperidine-4-carboxamide |
| II-379: | N-{4-[(3-amino-3-methylpyrrolidin-1-yl)carbonyl]phenyl}-9-chloro-7-(2,6-difluorophenyl)-5H-pyrimido[5,4-d][2]benzazepin-2-amine |
| II-380: | 9-chloro-7-(2,6-difluorophenyl)-N-(4-{[3-methyl-3-(methylamino)pyrrolidin-1-yl]carbonyl}phenyl)-5H-pyrimido[5,4-d][2]benzazepin-2-amine |
| II-381: | 1-(4-{[9-chloro-7-(2,6-difluorophenyl)-5H-pyrimido[5,4-d][2]benzazepin-2-yl]amino}benzoyl)-4-(methylamino)piperidine-4-carboxamide |
| II-382: | 9-chloro-7-(2,6-difluorophenyl)-N-{4-[(3,3,5-trimethylpiperazin-1-yl)carbonyl]phenyl}-5H-pyrimido[5,4-d][2]benzazepin-2-amine |
| II-383: | N-1-azabicyclo[2.2.2]oct-3-yl-4-{[9-chloro-7-(2,6-difluorophenyl)-5H-pyrimido[5,4-d][2]benzazepin-2-yl]amino}-N-methylbenzamide |
| II-384: | N-1-azabicyclo[2.2.2]oct-3-yl-4-{[9-chloro-7-(2,6-difluorophenyl)-5H-pyrimido[5,4-d][2]benzazepin-2-yl]amino}benzamide |
| II-385: | 4-{[9-chloro-7-(2,6-difluorophenyl)-5H-pyrimido[5,4-d][2]benzazepin-2-yl]amino}-N-hydroxybenzamide |
| II-386: | N-{4-[(aminooxy)carbonyl]phenyl}-9-chloro-7-(2,6-difluorophenyl)-5H-pyrimido[5,4-d][2]benzazepin-2-amine |
| II-387: | 4-{[9-chloro-7-(2,6-difluorophenyl)-7H-pyrimido[5,4-d][2]benzazepin-2-yl]amino}benzoic acid |
| II-388: | 4-{[9-chloro-7-(2,3-difluorophenyl)-7H-pyrimido[5,4-d][2]benzazepin-2-yl]amino}benzoic acid |
| II-389: | 3-amino-1-(4-{[9-chloro-7-(2,6-difluorophenyl)-5H-pyrimido[5,4-d][2]benzazepin-2-yl]amino}benzoyl)-N-methylpyrrolidine-3-Icarboxamide |
| II-390: | 3-amino-1-(2-chloro-4-{[9-chloro-7-(2,6-difluorophenyl)-5H-pyrimido[5,4-d][2]benzazepin-2-yl]amino}benzoyl)pyrrolidine-3-carboxamide |
| II-391: | 9-chloro-7-(2,6-difluorophenyl)-N-{4-[(3,3-dimethylpiperazin-1-yl)carbonyl]phenyl}-5H-pyrimido[5,4-d][2]benzazepin-2-amine |
| II-392: | 4-{[9-chloro-7-(2,6-difluorophenyl)-5H-pyrimido[5,4-d][2]benzazepin-2-yl]amino}-N-(8-methyl-8-azabicyclo[3.2.1]oct-3-yl)benzamide |
| II-393: | 9-chloro-7-(2,6-difluorophenyl)-N-(4-{[3-(dimethylamino)-3-methylpyrrolidin-1-yl]carbonyl}phenyl)-5H-pyrimido[5,4-d][2]benzazepin-2-amine |
| II-394: | 9-chloro-7-(2,6-difluorophenyl)-N-(3-methyl-1H-pyrazol-5-yl)-5H-pyrimido[5,4-d][2]benzazepin-2-amine |
| II-395: | 2-chloro-4-{[9-chloro-7(2,6-difluorophenyl)-5H-pyrimido[5,4-d][2]benzazepin-2-yl]amino}benzoic acid |

TABLE 1-continued

Examples of Compounds of Formula (II)

| | |
|---|---|
| II-396: | 4-amino-1-(2-chloro-4-{[9-chloro-7-(2,6-difluorophenyl)-5H-pyrimido[5,4-d][2]benzazepln-2-yl]amino}benzoyl)-N-methylpiperidine-4-carboxamide |
| II-397: | 4-amino-1-(2-chloro-4-{[9-chloro-7-(2,6-difluorophenyl)-5H-pyrimido[5,4-d][2]benzazepin-2-yl]amino}benzoyl)-N,N-dimethylpiperidine-4-carboxamide |
| II-398: | 4-[(9-methoxy-7-oxo-6,7-dihydro-5H-pyrimido[5,4-d][2]benzazepin-2-yl)amino]benzoic acid |
| II-399: | 2-({4-[(3,5-dimethylpiperazin-1-yl)carbonyl]phenyl}amino)-9-methoxy-5,6-dihydro-7H-pyrimido[5,4-d][2]benzazepin-7-one |
| II-400: | 9-methoxy-2-[(4-{[3-(methylamino)pyrrolidin-1-yl]carbonyl}phenyl)amino]-5,6-dihydro-7H-pyrimido[5,4-d][2]benzazepin-7-one |
| II-401: | 4-[(8-methyl-7-oxo-5,6,7,8-tetrahydropyrimido[5,4-c]pyrrolo[3,2-e]azepin-2-yl)amino]benzoic acid |
| II-402: | 2-({4-[(3,5-dimethylpiperazin-1-yl)carbonyl]phenyl}amino)-8-methyl-5,8-dihydropyrimido[5,4-c]pyrrolo[3,2-e]azepin-7(6H)-one |
| II-403: | 2-[(3-methoxyphenyl)amino]-8-methyl-5,8-dihydropyrimido[5,4-c]pyrrolo[3,2-e]azepin-7(6H)-one |
| II-404: | 9-chloro-2-[(3,4-dimethoxyphenyl)amino]-5,6-dihydro-7H-pyrimido[5,4-d][2]benzazepin-7-one |
| II-405: | 4-{[4-amino-9-chloro-7-(2,6-difluorophenyl)-5H-pyrimido[5,4-d][2]benzazepin-2-yl]amino}benzoic acid |
| II-406: | 9-chloro-N-(3-chloro-4-{[4-(methylamino)piperidin-1-yl]carbonyl}phenyl)-7-(2,6-difluorophenyl)-5H-pyrimido[5,4-d][2]benzazepin-2-amine |
| II-407: | 9-chloro-N-(3-chloro-4-{[4-(methylamino)piperidin-1-yl]carbonyl}phenyl)-7-(2-fluoro-6-methoxyphenyl)-5H-pyrimido[5,4-d][2]benzazepin-2-amine |
| II-408: | 4-{[9-chloro-7-(2-fluoro-6-hydroxyphenyl)-5H-pyrimido[5,4-d][2]benzazepin-2-yl]amino}benzoic acid |
| II-409: | 9-chloro-N-[4-(1,7-diazaspiro[4.4]non-7-ylcarbonyl)phenyl]-7-(2,6-difluorophenyl)-5H-pyrimido[5,4-d][2]benzazepin-2-amine |
| II-410: | 9-chloro-7-(2,6-difluorophenyl)-N-(4-{[2-(methylamino)-7-azabicyclo[2.2.1]hept-7-yl]carbonyl}phenyl)-5H-pyrimido[5,4-d][2]benzazepin-2-amine |
| II-411: | 1-(4-{[9-chloro-7-(2,6-difluorophenyl)-5H-pyrimido[5,4-d][2]benzazepin-2-yl]amino}benzoyl)-N-methyl-3-(methylamino)pyrrolidine-3-carboxamide |
| II-412: | 1-(4-{[9-chloro-7-(2,6-difluorophenyl)-5H-pyrimido[5,4-d][2]benzazepin-2-yl]amino}benzoyl)-3-(methylamino)pyrrolidine-3-carboxamide |
| II-413: | 1-(2-chloro-4-{[9-chloro-7-(2,6-difluorophenyl)-5H-pyrimido[5,4-d][2]benzazepin-2-yl]amino)benzoyl)-N-methyl-3-(methylamino)piperidine-3-carboxamide |
| II-414: | 9-chloro-7-(2,6-difluorophenyl)-N-(4-{[3-methyl-3-(methylamino)piperidin-1-yl]carbonyl}phenyl)-5H-pyrimido[5,4-d][2]benzazepin-2-amine |
| II-415: | 9-chloro-7-(2-fluoro-6-methoxyphenyl)-N-(4-{[3-methyl-3-(methylamino)piperidin-1-yl]carbonyl}phenyl)-5H-pyrimido[5,4-d][2]benzazepin-2-amine |
| II-416: | {2-Chloro-4-[9-chloro-7-(2-fluoro-6-methoxy-phenyl)-5H-benzo[c]pyrimido[4,5-e]azepin-2-ylamino]-phenyl}-(3-methyl-3-methylamino-piperidin-1-yl)-methanone |
| II-417: | 9-chloro-7-(2,6-difluorophenyl)-N-(4-{[4-methyl-4-(methylamino)piperidin-1-yl]carbonyl}phenyl)-5H-pyrimido[5,4-d][2]benzazepin-2-amine |
| II-418: | 9-chloro-7-(2,6-difluorophenyl)-N-(4-{[4-(dimethylamino)-4-methylpiperidin-1-yl]carbonyl}phenyl)-5H-pyrimido[5,4-d][2]benzazepin-2-amine |
| II-419: | N-{4-[(4-amino-4-methylpiperidin-1-yl)carbonyl]phenyl}-9-chloro-7-(2,6-difluorophenyl)-5H-pyrimido[5,4-d][2]benzazepin-2-amine |
| II-420: | 9-chloro-N-(3-chloro-4-{[4-methyl-4-(methylamino)piperidin-1-yl]carbonyl}phenyl)-7-(2,6-difluorophenyl)-5H-pyrimido[5,4-d][2]benzazepin-2-amine |
| II-421: | 9-chloro-7-(2-fluoro-6-methoxyphenyl)-N-(4-{[4-methyl-4-(methylamino)piperidin-1-yl]carbonyl}phenyl)-5H-pyrimido[5,4-d][2]benzazepin-2-amine |
| II-422: | 2-Chloro-4-[9-chloro-7-(2-fluoro-6-methoxy-phenyl)-5H-benzo[c]pyrimido[4,5-e]azepin-2-ylamino]-phenyl}-(4-methyl-4-methylamino-piperidin-1-yl)-methanone |
| II-423: | 9-chloro-7-(2-fluoro-6-methoxyphenyl)-N-(3-fluoro-4-{[4-methyl-4-(methylamino)piperidin-1-yl]carbonyl}phenyl)-5H-pyrimido[5,4-d][2]benzazepin-2-amine |
| II-424: | 9-chloro-N-{3-chloro-4-[(3,3,5,5-tetramethylpiperazin-1-yl)carbonyl]phenyl}-7-(2-fluoro-6-methoxyphenyl)-5H-pyrimido[5,4-d][2]benzazepin-2-amine |
| II-425: | N-1-azabicyclo[2.2.2]oct-3-yl-4-{[9-chloro-7-(2,6-difluorophenyl)-5H-pyrimido[5,4-d][2]benzazepin-2-yl]amino}-2-fluoro-N-methylbenzamide |

TABLE 1-continued

Examples of Compounds of Formula (II)

| | |
|---|---|
| II-426: | N-1-azabicyclo[2.2.2]oct-3-yl-4-{[9-chloro-7-(2-fluoro-6-methoxyphenyl)-5H-pyrimido[5,4-d][2]benzazepin-2-yl]amino}-N-methylbenzamide |
| II-427: | N-8-azabicyclo[3.2.1]oct-3-yl-4-{[9-chloro-7-(2,6-difluorophenyl)-5H-pyrimido[5,4-d][2]benzazepin-2-yl]amino}-N-methylbenzamide |
| II-428: | 9-chloro-7-{2,6-difluorophenyl}-N-(4-{[3-(methylamino)-8-azabicyclo[3.2.1]oct-8-yl]carbonyl}phenyl)-5H-pyrimido[5,4-d][2]benzazepin-2-amine |
| II-429: | 9-chloro-7-(2-fluoro-6-methoxyphenyl)-N-(4-{[3-(methylamino)-8-azabicyclo[3.2.1]oct-8-yl]carbonyl}phenyl)-5H-pyrimido[5,4-d][2]benzazepin-2-amine |
| II-430: | 4-{[7-(2,6-difluorophenyl)-9-methyl-5H-pyrimido[5,4-c]thieno[2,3-e]azepin-2-yl]amino}benzoic acid |
| II-431: | 7-(2,6-difluorophenyl)-N-{4-[(3,3,5,5-tetramethylpiperazin-1-yl)carbonyl]phenyl}-5H-pyrimido[5,4-c]thieno[2,3-e]azepin-2-amine |
| II-432: | N-{4-[(3-amino-3-methylpyrrolidin-1-yl)carbonyl]phenyl}-7-(2,6-difluorophenyl)-10-methyl-5,10-dihydropyrimido[5,4-d]pyrrolo[2,3-e]azepin-2-amine |
| II-433: | 7-(2,6-difluorophenyl)-9-methyl-N-(4-{[3-(methylamino)pyrrolidin-1-yl]carbonyl}phenyl)-5H-furo[2,3-c]pyrimido[4,5-e]azepin-2-amine |
| II-434: | 4-(2,6-difluorophenyl)-2-methyl-N-(4-{[3-methyl-3-(methylamino)pyrrolidin-1-yl]carbonyl}phenyl)-6H-pyrimido[5,4-c][1,3]thiazolo[4,5-e]azepin-9-amine |
| II-435: | N-{4-[{3-amino-3-methylpyrrolidin-1-yl]carbonyl]phenyl}-7-(2-fluoro-6-methoxyphenyl)-5,9-dihydropyrimido[5,4-c]pyrrolo[3,4-e]azepin-2-amine |
| II-436: | 4-{[4-(2,6-difluorophenyl)-1-methyl-1,6-dihydropyrazolo[4,3-c]pyrimido[4,5-e]azepin-9-yl]amino}benzoic acid |
| II-437: | 1-{4-[4-(2,6-Difluoro-phenyl)-2-methyl-6H-3-thia-5,8,10-triaza-benzo[e]azulen-9-ylamino]-benzoyl}-4-dimethylamino-piperidine-4-carboxylic acid methylamide |
| II-438: | 4-(4-{[7-(2,6-difluorophenyl)-5H-furo[3,2-c]pyrimido[4,5-e]azepin-2-yl]amino}benzoyl)-N-methylpiperazine-2-carboxamide |
| II-439: | 4-(4-{[4-(2,6-difluorophenyl)-6H-isoxazolo[4,5-c]pyrimido[4,5-e]azepin-9-yl]amino}benzoyl)-N-methylpiperazine-2-carboxamide |
| II-440: | 4-(2,6-difluorophenyl)-9-[(4-{[3-methyl-3-(methylamino)pyrrolidin-1-yl]carbonyl}phenyl)amino]-3,6-dihydroimidazo[4,5-c]pyrimido[4,5-e]azepin-2(1H)-one |
| II-441: | 2-amino-N-(3-{[7-(2,6-difluorophenyl)-8,10-dimethyl-5H-pyrimido[5,4-c]thieno[3,4-e]azepin-2-yl]amino}phenyl)-N,2-dimethylpropanamide |
| II-442: | 9-chloro-7-(2,6-difluorophenyl)-N-{3-[(2,2,6,6-tetramethylpiperidin-4-yl)oxy]phenyl}-5H-pyrimido[5,4-d][2]benzazepin-2-amine |
| II-443: | 4-(4-{[9-chloro-7-(2,6-difluorophenyl)-5H-pyrimido[5,4-d][2]benzazepin-2-yl]amino}phenyl)-N-methyl-1-(methylamino)cyclohexanecarboxamide |
| II-444: | 7-(3-{[7-(2-fluoro-6-methoxyphenyl)-9-methoxy-5H-pyrimido[5,4-d][2]benzazepin-2-yl]amino}phenyl)-1,7-diazaspiro[4.4]nonan-6-one |
| II-445: | 9-chloro-N-[4-(3,8-diazabicyclo[3.2.1]oct-3-ylcarbonyl)phenyl]-7-(2,6-difluorophenyl)-5H-pyrimido[5,4-d][2]benzazepin-2-amine |
| II-446: | 1-(3-{[9-chloro-7-(2,6-difluorophenyl)-5H-pyrimido[5,4-d][2]benzazepin-2-yl]amino}phenyl)-3,5,5-trimethylpiperazin-2-one |
| II-447: | 9-chloro-N-[4-(2,6-dimethylpiperidin-4-yl)phenyl]-7-(2-fluoro-6-methoxyphenyl)-5H-pyrimido[5,4-d][2]benzazepin-2-amine |
| II-448: | N-[4-(1-amino-1-methylethyl)phenyl]-9-chloro-7-(2,6-difluorophenyl)-5H-pyrimido[5,4-d][2]benzazepin-2-amine |
| II-449: | N-[4-(2,5-diazaspiro[3.4]oct-2-ylcarbonyl)phenyl]-7-(2,6-difluorophenyl)-10-methyl-5H-isothiazolo[5,4-c]pyrimido[4,5-e]azepin-2-amine |
| II-450: | 4-(2,6-difluorophenyl)-1-methyl-9-[(4-{[4-methyl-4-(methylamino)piperidin-1-yl]carbonyl}phenyl)amino]-1,6-dihydro-2H-pyrimido[5,4-c][1,3]thiazolo[4,5-e]azepin-2-one |
| II-451: | 4-(2,6-difluorophenyl)-N-[4-(1H-imidazol-2-yl)phenyl]-1-methyl-1,6-dihydroimidazo[4,5-c]pyrimido[4,5-e]azepin-9-amine |
| II-452: | 4-{[7-(2,6-difluorophenyl)-5H-[1]benzofuro[2,3-c]pyrimido[4,5-e]azepin-2-yl]amino}benzoic acid |
| II-453: | 7-(2-fluorophenyl)-N-{4-[(3,3,5,5-tetramethylpiperazin-1-yl)carbonyl]phenyl}-8,9,10,11-tetrahydro-5H-pyrido[4',3':4,5]thieno[3,2-c]pyrimido[4,5-e]azepin-2-amine |
| II-454: | 9-bromo-7-(2-fluorophenyl)-N-(4-{[3-(methylamino)pyrrolidin-1-yl]carbonyl}phenyl)-5,8-dihydropyrimido[5,4-c]pyrrolo[3,2-e]azepin-2-amine |
| II-455: | 7-(2-fluorophenyl)-N-(3-methyl-1H-indazol-6-yl)-5,12-dihydropyrimido[4',5':5,6]azepino[4,3-b]indol-2-amine |
| II-456: | 1-{4-{[7-(2,6-difluorophenyl)-9,10-dimethyl-5,8-dihydropyrimido[5,4-c]pyrrolo[3,2-e]azepin-2-yl]amino}benzoyl)-3-(methylamino)pyrrolidine-3-carboxamide |
| II-457: | (3-[9-Chloro-7-(2-fluoro-6-methoxy-phenyl)-5H-benzo[c]pyrimido-[4,5-e]azepin-2-ylamino]-phenyl}-(4-methyl-piperazin-l-yl)-methanone |
| II-458: | [9-Chloro-7-(2,6-difluoro-phenyl)-5H-benzo[c]pyrimido[4,5-e]azepin-2-yl]-(2-methylaminomethyl-benzothiazol-6-yl)-amine |
| II-459: | 4-[9-Chloro-7-(2-isopropoxy-phenyl)-5H-benzo[c]pyrimido[4,5-e]azepin-2-ylamino]-benzoic acid |

TABLE 1-continued

Examples of Compounds of Formula (II)

| | |
|---|---|
| II-460: | 4-[9-Chloro-7-(2-fluoro-6-isopropoxy-phenyl)-5H-benzo[c]pyrimido-[4,5-e]azepin-2-ylamino]-benzoic acid |
| II-461: | 4-[9-Chloro-7-(2-ethoxy-phenyl)-5H-benzo[c]pyrimido[4,5-e]azepin-2-ylamino]-benzoic acid |
| II-462: | 4-[9-Chloro-7-(2-ethoxy-6-fluoro-phenyl)-5H-benzo[c]pyrimido-[4,5-e]azepin-2-ylamino]-benzoic acid |
| II-463: | 4-[9-Chloro-7-(2-fluoro-6-methyl-phenyl)-5H-benzo[c]pyrimido-[4,5-e]azepin-2-ylamino]-benzoic acid |
| II-464: | 4-[9-Chloro-7-(2-trifluoromethoxy-phenyl)-5H-benzo[c]pyrimido-[4,5-e]azepin-2-ylamino]-benzoic acid |
| II-465: | 4-[9-Chloro-7-(2-fluoro-6-trifluoromethoxy-phenyl)-5H-benzo[c]pyrimido[4,5-e]azepin-2-ylamino]-benzoic acid |
| II-466: | 4-[9-Chloro-7-(3-fluoro-2-trifluoromethoxy-phenyl)-5H-benzo[c]pyrimido[4,5-e]azepin-2-ylamino]-benzoic acid |
| II-467: | 4-[9-Chloro-7-(2,3-dimethoxy-phenyl)-5H-benzo[c]pyrimido-[4,5-e]azepin-2-ylamino]-benzoic acid |
| II-468: | 4-[9-Chloro-7-(2-isobutyl-phenyl)-5H-benzo[c]pyrimido[4,5-e]azepin-2-ylamino]-benzoic acid |
| II-469: | 4-(7-Benzofuran-2-yl-9-chloro-5H-benzo[c]pyrimido[4,5-e]azepin-2-ylamino)-benzoic acid |
| II-470: | 4-[9-Chloro-7-(1-methyl-1H-pyrrol-2-yl)-5H-benzo[c]pyrimido-[4,5-e]azepin-2-ylamino]-benzoic acid |
| II-471: | 4-[9-Chloro-7-(1-methyl-1H-imidazol-2-yl)-5H-benzo[c]pyrimido-[4,5-e]azepin-2-ylamino]-benzoic acid |
| II-472: | 4-(9-Chloro-7-thiophen-2-yl-5H-benzo[c]pyrimido[4,5-e]azepin-2-ylamino)-benzoic acid |
| II-473: | 4-[9-Chloro-7-(2H-pyrazol-3-yl)-5H-benzo[c]pyrimido[4,5-e]azepin-2-ylamino]-benzoic acid |
| II-474: | 4-[9-Chloro-7-(2-ethynyl-phenyl)-5H-benzo[c]pyrimido[4,5-e]azepin-2-ylamino]-benzoic acid |
| II-475: | 4-[7-(2-aminomethyl-phenyl)-9-chloro-5H-benzo[c]pyrimido-[4,5-e]azepin-2-ylamino]-benzoic acid |
| II-476: | 4-[9-Chloro-7-(5-fluoro-2-methoxy-phenyl)-5H-benzo[c]pyrimido-[4,5-e]azepin-2-ylamino]-benzoic acid |
| II-477: | 4-[9-Chloro-7-(3-methoxy-pyridin-2-yl)-5H-benzo[c]pyrimido-[4,5-e]azepin-2-ylamino]-benzoic acid |
| II-478: | 4-[8-Fluoro-7-(2-fluoro-phenyl)-5H-benzo[c]pyrimido[4,5-e]azepin-2-ylamino]-benzoic acid |
| II-479: | 4-[8-Chloro-7-(2-fluoro-phenyl)-5H-benzo[c]pyrimido[4,5-e]azepin-2-ylamino]-benzoic acid |
| II-480: | 4-[11-Fluoro-7-(2-fluoro-phenyl)-5H-benzo[c]pyrimido[4,5-e]azepin-2-ylamino]-benzoic acid |
| II-481: | 4-[11-Chloro-7-(2-fluoro-phenyl)-5H-benzo[c]pyrimido[4,5-e]azepin-2-ylamino]-benzoic acid |
| II-482: | 6-[9-Chloro-7-(2-fluoro-phenyl)-5H-benzo[c]pyrimido[4,5-e]azepin-2-ylamino]-pyridazine-3-carboxylic acid |
| II-483: | 2-[9-Chloro-7-(2-fluoro-phenyl)-5H-benzo[c]pyrimido[4,5-e]azepin-2-ylamino]-1H-imidazole-4-carboxylic acid |
| II-484: | 4-[9-Chloro-7-(2-fluoro-phenyl)-4-methyl-5H-benzo[c]pyrimido-[4,5-e]azepin-2-ylamino]-benzoic acid |
| II-485: | 4-[4-Aminomethyl-9-chloro-7-(2-fluoro-phenyl)-5H-benzo[c]pyrimido-[4,5-e]azepin-2-ylamino]-benzoic acid |
| II-486: | 4-(9-Aminomethyl-7-phenyl-5H-benzo[c]pyrimido[4,5-e]azepin-2-ylamino)-benzoic acid |
| II-487: | 9-Chloro-7-(2-fluorophenyl)-N-{4-[(2-methylpiperazin-1-yl)carbonyl]phenyl}-5H-pyrimido[5,4-d][2]benzazepin-2-amine |
| II-488: | 4-{[9-Chloro-7-(2-fluorophenyl)-5H-pyrimido[5,4-d][2]benzazepin-2-yl]amino}-N-[{3-[(dimethylamino)methyl]azetidin-1-yl}(imino)methyl]benzamide |
| II-489: | 4-{[9-Chloro-7-(2-fluorophenyl)-5H-pyrimido[5,4-d][2]benzazepin-2-yl]amino}-N-[amino(piperazin-1-yl)methyl]benzamide |
| II-490: | 4-{[9-Chloro-7-(2-fluorophenyl)-5H-pyrimido[5,4-d][2]benzazepin-2-yl]amino}-N-[imino(3-methylpiperazin-1-yl)methyl]benzamide |
| II-491: | 4-{[9-Chloro-7-(2-fluorophenyl)-5H-pyrimido[5,4-d][2]benzazepin-2-yl]amino}-N-[[3-(dimethylamino)pyrrolidin-1-yl](imino)methyl]benzamide |
| II-492: | 4-{[9-Chloro-7-(2-fluorophenyl)-5H-pyrimido[5,4-d][2]benzazepin-2-yl]amino}-N-[imino(4-methylpiperazin-1-yl)methyl]benzamide |
| II-493: | 4-{[9-Chloro-7-(2-fluorophenyl)-5H-pyrimido[5,4-d][2]benzazepin-2-yl]amino}-N-[(3,5-dimethylpiperazin-1-yl)(imino)methyl]benzamide |
| II-494: | 1-[[(4-{[9-Chloro-7-(2-fluorophenyl)-5H-pyrimido[5,4-d][2]benzazepin-2-yl]amino}benzoyl)amino](imino)methyl]pyrrolidine-3-carboxamide |
| II-495: | 1-[[(4-{[9-Chloro-7-(2-fluorophenyl)-5H-pyrimido[5,4-d][2]benzazepin-2-yl]amino}benzoyl)amino](imino)methyl]piperidine-3-carboxamide |
| II-496: | 4-{[9-Chloro-7-(2-fluorophenyl)-5H-pyrimido[5,4-d][2]benzazepin-2-yl]amino}-N-[{4-[(cyclopropylcarbonyl)amino]piperidin-1-yl}(imino)methyl]benzamide |

TABLE 1-continued

Examples of Compounds of Formula (II)

| | |
|---|---|
| II-497: | 4-{[9-Chloro-7-(2-fluorophenyl)-5H-pyrimido[5,4-d][2]benzazepin-2-yl]amino}-N-[(dimethylamino)(imino)methyl]benzamide |
| II-498: | N-[[(4-{[9-Chloro-7-(2-fluorophenyl)-5H-pyrimido[5,4-d][2]benzazepin-2-yl]amino}phenyl)amino](imino)methyl]cyclopropanecarboxamide |
| II-499: | N-[[(4-{[9-Chloro-7-(2-fluorophenyl)-5H-pyrimido[5,4-d][2]benzazepin-2-yl]amino}phenyl)amino](imino)methyl]-3-(dimethylamino)cyclopentanecarboxamide |
| II-500: | 4-({9-Chloro-7-[2-fluoro-6-(trifluoromethyl)phenyl]-5H-pyrimido-[5,4-d][2]benzazepin-2-yl}amino)benzoic acid |
| II-501: | 4-{[9-Chloro-7-(2,6-dichlorophenyl)-5H>-pyrimido[5,4-d][2]benzazepin-2-yl]amino}benzoic acid |
| II-502: | 4-{[9-Chloro-7-(2-fluoro-6-methylphenyl)-5H-pyrimido-[5,4-d][2]benzazepin-2-yl]amino}benzoic acid |
| II-503: | 4-{[7-(2-Bromo-6-chlorophenyl)-9-chloro-5H-pyrimido-[5,4-d][2]benzazepin-2-yl]amino}benzoic acid |
| II-504: | 9-Chloro-7-(2,6-difluorophenyl)-N-{4-[(3,5-dimethylpiperazin-1-yl)carbonyl]-3-fluorophenyl}-5H-pyrimido[5,4-d][2]benzazepin-2-amine |
| II-505: | 4-{[9-Chloro-7-(2,6-difluorophenyl)-5H-pyrimido[5,4-d][2]benzazepin-2-yl]amino}-N-[(3,5-dimethylpiperazin-1-yl)(imino)methyl]-N-methylbenzamide |
| II-506: | 4-{[9-Chloro-7-(2,6-difluorophenyl)-5H-pyrimido[5,4-d][2]benzazepin-2-yl]amino}-N-[[3-(dimethylamino)azetidin-1-yl](imino)methyl]-N-methylbenzamide |
| II-507: | 3-{[9-Chloro-7-(2,6-difluorophenyl)-5H-pyrimido[5,4-d][2]benzazepin-2-yl]imino}-N-[(3,5-dimethylpiperazin-1-yl)(imino)methyl]benzamide |
| II-508: | 3-{[9-Chloro-7-(2,6-difluorophenyl)-5H-pyrimido[5,4-d][2]benzazepin-2-yl]amino}-N-[[3-(dimethylamino)pyrrolidin-1-yl](imino)methyl]benzamide |
| II-509: | 9-Chloro-7-(2,6-difluorophenyl)-N-{3-[(3,5-dimethylpiperazin-1-yl)carbonyl]-4-fluorophenyl}-5H-pyrimido[5,4-d][2]benzazepin-2-amine |
| II-510: | N-[[(4-{[9-Chloro-7-(2,6-difluorophenyl)-5H-pyrimido-[5,4-d][2]benzazepin-2-yl]amino}phenyl)amino](imino)methyl]-3-(dimethylamino)cyclopentanecarboxamide |
| II-511: | N-[[(4-{[9-Chloro-7-(2,6-difluorophenyl)-5H-pyrimido-[5,4-d][2]benzazepin-2-yl]amino}-2-fluorophenyl)amino](imino)methyl]-3-(dimethylamino)cyclopentanecarboxamide |
| II-512: | N-[[(5-{[9-Chloro-7-(2,6-difluorophenyl)-5H-pyrimido-[5,4-d][2]benzazepin-2-yl]amino}-2-fluorophenyl)amino](imino)methyl]-3-(dimethylamino)cyclopentanecarboxamide |
| II-513: | N-(4-{[9-Chloro-7-(2,6-difluorophenyl)-5H-pyrimido[5,4-d][2]benzazepin-2-yl]amino}phenyl)-3,5-dimethylpiperazine-1-carboximidamide |
| II-514: | 4-{[9-Chloro-7-(2,6-difluorophenyl)-5H-pyrimido[5,4-d][2]benzazepin-2-yl]amino}-N-[[3-(dimethylamino)pyrrolidin-1-yl](imino)methyl]-N-methylbenzamide |
| II-515: | N-(3-{[9-Chloro-7-(2,6-difluorophenyl)-5*H*-pyrimido-[5,4-d][2]benzazepin-2-yl]amino}phenyl)-3,5-dimethylpiperazine-1-carboximidamide |
| II-516: | N-(3-{[9-Chloro-7-(2,6-difluorophenyl)-5H-pyrimido[5,4-d][2]benzazepin-2-yl]amino}phenyl)-N,3,5-trimethylpiperazine-1-carboximidamide |
| II-517: | 3-{[9-Chloro-7-(2,6-difluorophenyl)-5H-pyrimido[5,4-d][2]benzazepin-2-yl]amino}-N-[[3-(dimethylamino)azetidin-1-yl](imino)methyl]benzamide |
| II-518: | N-(5-{[9-Chloro-7-(2,6-difluorophenyl)-5H-pyrimido[5,4-d][2]benzazepin-2-yl]amino}-2-fluorophenyl)-N,3,5-trimethylpiperazine-1-caboximidamide |
| II-519: | N-[[(3-{[9-Chloro-7-(2,6-difluorophenyl)-5H-pyrimido-[5,4-d][2]benzazepin-2-yl]amino}phenyl)amino](imino)methyl]-3-(dimethylamino)cyclopentanecarboxamide |
| II-520: | 9-Chloro-7-(2,6-difluorophenyl)-N-{3-[(3,5-dimethylpiperazin-1-yl)(imino)methyl]phenyl}-5H-pyrimido[5,4-d][2]benzazepin-2-amine |
| II-521: | N-(4-{[9-Chloro-7-(2,6-difluorophenyl)-5H-pyrimido[5,4-d][2]benzazepin-2-yl]amino}phenyl)-N,3,5-trimethylpiperazine-1-carboximidamide |
| II-522: | N-(4-{[9-Chloro-7-(2,6-difluorophenyl)-5H-pyrimido[5,4-d][2]benzazepin-2-yl]amino}-2-fluorophenyl)-3,5-dimethylpiperazine-1-carboximidamide |
| II-523: | 9-Chloro-7-(2,6-difluorophenyl)-N-{4-[(3,5-dimethylpiperazin-1-yl)(imino)methyl]-3-fluorophenyl}-5H-pyrimido[5,4-d][2]benzazepin-2-amine |
| II-524: | 5-{[9-Chloro-7-(2,6-difluorophenyl)-5H-pyrimido[5,4-d][2]benzazepin-2-yl]amino}-2-(2,6-dimethylpiperidin-4-yl)-1H-isoindole-1,3(2H)-dione |
| II-525: | N-[2-(Aminomethyl)-1H-benzimidazol-6-yl]-9-chloro-7-(2-fluorophenyl)-5H-pyrimido[5,4-d][2]benzazepin-2-amine |
| II-526: | 9-Chloro-7-(2-fluorophenyl)-N-{2-[(methylamino)methyl]-1H-benzimidazol-6-yl}-5H-pyrimido[5,4-d][2]benzazepin-2-amine |
| II-527: | 9-Chloro-N-{2-[(dimethylamino)methyl]-1H-benzimidazol-6-yl}-7-(2-fluorophenyl)-5H-pyrimido[5,4-d][2]benzazepin-2-amine |
| II-528: | 9-Chloro-7-(2-fluorophenyl)-N-{2-[(methylamino)methyl]-1,3-benzothiazol-6-yl}-5H-pyrimido[5,4-d][2]benzazepin-2-amine |
| II-529: | 9-Chloro-7-(2,6-difluorophenyl)-N-{2-[(methylamino)methyl]-1H-benzimidazol-6-yl}-5H-pyrimido[5,4-d][2]benzazepin-2-amine |

TABLE 1-continued

Examples of Compounds of Formula (II)

II-530: 9-Chloro-7-(2,6-difluorophenyl)-N-{2-[(methylamino)methyl]-1,3-benzoxazol-6-yl}-5H-pyrimido[5,4-d][2]benzazepin-2-amine
II-531: 9-Chloro-7-(2-fluorophenyl)-N-{2-[(methylamino)methyl]-1,3-benzoxazol-6-yl}-5H-pyrimido[5,4-d][2]benzaazepin-2-amine
II-532: 9-Chloro-7-(2,6-difluorophenyl)-N-{3-[(3,5-dimethylpiperazin-1-yl)(imino)methyl]-4-fluorophenyl}-5H-pyrimido[5,4-d][2]benzazepin-2-amine
II-533: 9-Chloro-7-(2,6-difluorophenyl)-N-{2-[(methylamino)methyl]-1,3-benzothiazol-6-yl}-5H-pyrimido[5,4-d][2]benzazepin-2-amine
II-534: {3-[9-Chloro-7-(2,6-difluorophenyl)-5H-benzo[c]pyrimido[4,5-e]azepin-2-ylamino]-phenyl}-(4-methyl-piperazin-1-yl)-methanone
II-535: 3-[9-Chloro-7-(2,6-difluoro-phenyl)-5H-benzo[c]pyrimido[4,5-e]azepin-2-ylamino]-N-methyl-N-(4-methyl-pentyl)-benzamide In some embodiments, the Aurora kinase inhibitor is represented by formula (III):

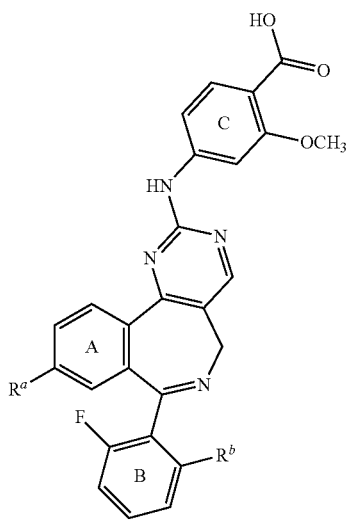

(III)

or a pharmaceutically acceptable salt thereof;
wherein:
$R^a$ is selected from the group consisting of $C_{1-3}$ aliphatic, $C_{1-3}$ fluoroaliphatic, —$R^1$, -T-$R^1$, —$R^2$, and -T-$R^2$;
T is a $C_{1-3}$ alkylene chain optionally substituted with fluoro;
$R^1$ is an optionally substituted aryl, heteroaryl, or heterocyclyl group;
$R^2$ is selected from the group consisting of halo, —C≡C—$R^3$, —CH=CH—$R^3$, —N($R^4$)$_2$, and —O$R^5$;
$R^3$ is hydrogen or an optionally substituted aliphatic, aryl, heteroaryl, or heterocyclyl group;

each $R^4$ independently is hydrogen or an optionally substituted aliphatic, aryl, heteroaryl, or heterocyclyl group; or two $R^4$ on the same nitrogen atom, taken together with the nitrogen atom form an optionally substituted 5- to 6-membered heteroaryl or 4- to 8-membered heterocyclyl ring having, in addition to the nitrogen atom, 0-2 ring heteroatoms selected from N, O, and S;
$R^5$ is hydrogen or an optionally substituted aliphatic, aryl, heteroaryl, or heterocyclyl group; and
$R^b$ is selected from the group consisting of fluoro, chloro, —CH$_3$, —CF$_3$, —OH, —OCH$_3$, —OCF$_3$, —OCH$_2$CH$_3$, and —OCH$_2$CF$_3$.

In some embodiments, $R^1$ is a 5- or 6-membered aryl, heteroaryl, or heterocyclyl ring optionally substituted with one or two substituents independently selected from the group consisting of halo, $C_{1-3}$ aliphatic, and $C_{1-3}$ fluoroaliphatic. In certain embodiments, $R^1$ is a phenyl, furyl, pyrrolidinyl, or thienyl ring optionally substituted with one or two substituents independently selected from the group consisting of halo, $C_{1-3}$ aliphatic, and $C_{1-3}$ fluoroaliphatic.

In some embodiments, $R^3$ is hydrogen, $C_{1-3}$ aliphatic, $C_{1-3}$ fluoroaliphatic, or —CH$_2$—OCH$_3$.

In some embodiments, $R^5$ is hydrogen, $C_{1-3}$ aliphatic, or $C_{1-3}$ fluoroaliphatic.

In certain embodiments, $R^a$ is halo, $C_{1-3}$ aliphatic, $C_{1-3}$ fluoroaliphatic, —OH, —O($C_{1-3}$ aliphatic), —O($C_{1-3}$ fluoroaliphatic), —C≡C—$R^3$, —CH=CH—$R^3$, or an optionally substituted pyrrolidinyl, thienyl, furyl, or phenyl ring, wherein $R^3$ is hydrogen, $C_{1-3}$ aliphatic, $C_{1-3}$ fluoroaliphatic, or —CH$_2$—OCH$_3$. In certain particular embodiments, $R^a$ is selected from the group consisting of chloro, fluoro, $C_{1-3}$ aliphatic, $C_{1-3}$ fluoroaliphatic, —OCH$_3$, —OCF$_3$, —C≡C—H, —C≡C—CH$_3$, —C≡C—CH$_2$OCH$_3$, —CH=CH$_2$, —CH=CHCH$_3$, N-methylpyrrolidinyl, thienyl, methylthienyl, furyl, methylfuryl, phenyl, fluorophenyl, and tolyl.

Table 2 provides the chemical names for specific examples of compounds of formula (III).

TABLE 2

Examples of Compounds of Formula (III)

Chemical Name

III-1 4-{[9-chloro-7-(2-fluoro-6-methoxyphenyl)-5H-pyrimido[5,4-d][2]benzazepin-2-yl]amino}-2-methoxybenzoic acid
III-2 4-{[9-ethynyl-7-(2-fluoro-6-methoxyphenyl)-5H-pyrimido[5,4-d][2]benzazepin-2-yl]amino}-2-methoxybenzoic acid
III-3 4-({9-chloro-7-[2-fluoro-6-(trifluoromethoxy)phenyl]-5H-pyrimido[5,4-d][2]benzazepin-2-yl}amino)-2-methoxybenzoic acid TABLE 2-continued Examples of Compounds of Formula (III)

| | Chemical Name |
|---|---|
| III-4 | 4-{[7-(2-fluoro-6-methoxyphenyl)-9-(1-methyl-1H-pyrrol-2-yl)-5H-pyrimido[5,4-d][2]benzazepin-2-yl]amino}-2-methoxybenzoic acid |
| III-5 | 4-{[7-(2-fluoro-6-methoxyphenyl)-9-(4-methyl-3-thienyl)-5H-pyrimido[5,4-d][2]benzazepin-2-yl]amino}-2-methoxybenzoic acid |
| III-6 | 4-{[7-(2-fluoro-6-methoxyphenyl)-9-(3-methyl-2-furyl)-5H-pyrimido[5,4-d][2]benzazepin-2-yl]amino}-2-methoxybenzoic acid |
| III-7 | 4-({9-ethynyl-7-[2-fluoro-6-(2,2,2-trifluoroethoxy)phenyl]-5H-pyrimido[5,4-d][2]benzazepin-2-yl}amino)-2-methoxybenzoic acid |
| III-8 | 4-{[9-chloro-7-(2,6-difluorophenyl)-5H-pyrimido[5,4-d][2]benzazepin-2-yl]amino}-2-methoxybenzoic acid |
| III-9 | 4-{[7-(2-fluoro-6-methoxyphenyl)-9-(2-methylphenyl)-5H-pyrimido[5,4-d][2]benzazepin-2-yl]amino}-2-methoxybenzoic acid |
| III-10 | 4-{[7-(2-fluoro-6-methoxyphenyl)-9-prop-1-yn-1-yl-5H-pyrimido[5,4-d][2]benzazepin-2-yl]amino)-2-methoxybenzoic acid |
| III-11 | 4-{[7-(2-fluoro-6-methoxyphenyl)-9-vinyl-5H-pyrimido[5,4-d][2]benzazepin-2-yl]amino}-2-methoxybenzoic acid |
| III-12 | 4-{[7-(2-fluoro-6-methoxyphenyl)-9-(2-fluorophenyl)-5H-pyrimido[5,4-d][2]benzazepin-2-yl]amino)-2-methoxybenzoic acid |
| III-13 | 4-{[7-(2-fluoro-6-methoxyphenyl)-9-(3-methoxyprop-1-yn-1-yl)-5H-pyrimido[5,4-d][2]benzazepin-2-yl]amino}-2-methoxybenzoic acid |
| III-14 | 4-({7-(2-fluoro-6-methoxyphenyl)-9-[(1E)-prop-1-en-1-yl]-5H-pyrimido[5,4-d][2]benzazepin-2-yl}amino)-2-methoxybenzoic acid |
| III-15 | 4-({9-chloro-7-[2-fluoro-6-(2,2,2-trifluoroethoxy)phenyl]-5H-pyrimido[5,4-d][2]benzazepin-2-yl}amino)-2-methoxybenzoic acid |
| III-16 | 4-{[7-{2-fluoro-6-methoxyphenyl)-9-(2-furyl)-5H-pyrimido[5,4-d][2]benzazepin-2-yl]amino}-2-methoxybenzoic acid |
| III-17 | 4-{[9-chloro-7-(2-fluoro-6-hydroxyphenyl)-5H-pyrimido[5,4-d][2]benzazepin-2-yl]amino}-2-methoxybenzoic acid |
| III-18 | 4-{[7-(2-fluoro-6-methoxyphenyl)-9-phenyl-5H-pyrimido[5,4-d][2]benzazepin-2-yl]amino}-2-methoxybenzoic acid |

In one embodiment, the compound of formula (III) is 4-{[9-chloro-7-(2-fluoro-6-methoxyphenyl)-5H-pyrimido[5,4-d][2]benzazepin-2-yl]amino}-2-methoxybenzoic acid or a pharmaceutically acceptable salt thereof. In a particular embodiment, the compound of formula (III) is sodium 4-{[9-chloro-7-(2-fluoro-6-methoxyphenyl)-5H-pyrimido[5,4-d][2]benzazepin-2-yl]amino}-2-methoxybenzoate.

Any antibody capable of binding the CD20 antigen may be used in the methods of the instant invention. Antibodies which bind the CD20 antigen include, for example: C2B8 (rituximab; RITUXAN®) (U.S. Pat. No. 5,736,137, expressly incorporated herein by reference); the yttrium-[90]-labeled 2138 murine antibody designated Y2B8 (U.S. Pat. No. 5,736,137, expressly incorporated herein by reference); murine IgG2a 131 optionally labeled with 131 1 to generate the 131 1-B1 antibody (BEXXARTM®) (U.S. Pat. No. 5,595,721, expressly incorporated herein by reference); murine monoclonal antibody 1F5 (Press et al. Blood 69(2): 584-591 (1987)); chimeric 2H7 antibody (U.S. Pat. No. 5,677,180 expressly incorporated herein by reference); and monoclonal antibodies L27, G28-2, 93-1 133, B—C1 or NU—B2 available from the International Leukocyte Typing Workshop (Valentine et al., In: Leukocyte TypingIII (McMichael, Ed., p. 440, Oxford University Press (1987)).

In some embodiments, the anti-CD20 antibody is rituximab. Rituximab is a genetically engineered chimeric murine/human monoclonal antibody. Rituximab is an IgG, kappa immunoglobulin containing murine light and heavy chain variable region sequences and human constant region sequences. Rituximab has a binding affinity for the CD20 antigen of approximately 8.0 nM. It is commercially available, e.g., from Genentech (South San Francisco, Calif.).

In some embodiments, the anti-CD20 antibody used in the present invention may be administered along with standard of care chemotherapeutic agents/combinations, such as, for example, CHOP chemotherapy regimen, which is a regimen consisting of the combination of cyclophosphamide, doxorubicin, vincristine and prednisolone. Rituximab has been approved in combination with CHOP chemotherapy for the treatment of certain types of lymphomas and this combination has become known as RCHOP chemotherapy.

Compounds of formulas (I), (II) and (III), as well as compounds disclosed in, for example, WO 05/111039, US2005/0256102, US2007/0185087, WO 08/021038, US2008/0045501, WO 08/063525, US2008/0167292, WO 07/113212, EP1644376, US2005/0032839, WO 05/005427, WO 06/070192, WO 06/070198, WO 06/070202, WO 06/070195, WO 06/003440, WO 05/002576, WO 05/002552, WO 04/071507, WO 04/058781, WO 06/055528, WO 06/055561, WO 05/118544, WO 05/013996, WO 06/036266, US2006/0160874, US2007/0142368, WO 04/043953, WO 07/132220, WO 07/132221, WO 07/132228, WO 04/00833 and WO 07/056164 are inhibitors of Aurora kinase. The compounds can be assayed in vitro or in vivo for their ability to bind to and/or inhibit an Aurora kinase. In vitro assays include assays to determine inhibition of the ability of an Aurora kinase to phosphorylate a substrate protein or peptide. Alternate in vitro assays quantitate the ability of the compound to bind to an Aurora kinase. Inhibitor binding may be measured by radiolabelling the inhibitor prior to binding, isolating the inhibitor/Aurora kinase complex and determining the amount of radiolabel bound. Alternatively, inhibitor binding may be determined by running a competition experiment in which new inhibitors are incubated with Aurora kinase bound to a known radioligand. The compounds also can be assayed for their ability to affect cellular or physiological functions mediated by Aurora kinase activity. Assays for each of these activities are known in the art.

In another aspect, therefore, the invention provides a method for inhibiting cellular growth/cellular proliferation comprising contacting a cell with an Aurora kinase inhibitor in combination with an anti-CD20 antibody, such as, e.g., rituximab. In an another embodiment, the invention provides a method for inhibiting cellular growth/cellular proliferation comprising contacting a cell with an Aurora kinase inhibitor in combination RCHOP chemotherapy.

Preferably, the method according to the invention causes an inhibition of cell proliferation of the contacted cells. The phrase "inhibiting cell proliferation" is used to denote an ability of an inhibitor of Aurora kinase and/or anti-CD20 antibody to inhibit cell number or cell growth in contacted cells as compared to cells not contacted with the inhibitor and/or antibody. An assessment of cell proliferation can be made by counting cells using a cell counter or by an assay of cell viability, e.g., a BrdU, MTT, XTT, or WST assay. Where the cells are in a solid growth (e.g., a solid tumor or organ), such an assessment of cell proliferation can be made by measuring the growth, e.g., with calipers, and comparing the size of the growth of contacted cells with non-contacted cells.

Preferably, the growth of cells contacted with an Aurora kinase inhibitor and an anti-CD20 antibody is retarded by at least about 50% as compared to growth of non-contacted cells. In various embodiments, cell proliferation of contacted cells is inhibited by at least about 75%, at least about 90%, or at least about 95% as compared to non-contacted cells. In some embodiments, the phrase "inhibiting cell proliferation" includes a reduction in the number of contacted cells, as compare to non-contacted cells. Thus, an inhibitor of Aurora kinase and/or an anti-CD20 antibody that inhibits cell proliferation in a contacted cell may induce the contacted cell to undergo growth retardation, to undergo growth arrest, to undergo programmed cell death (i.e., apoptosis), or to undergo necrotic cell death.

In another aspect, the invention provides a pharmaceutical composition comprising i) an Aurora kinase inhibitor; and ii) an anti-CD20 antibody. In some embodiments the Aurora kinase inhibitor is selected from the group consisting of i) the compounds of formulas (I), (II) and (III); ii) the compounds disclosed in, for example, WO 05/111039, US2005/0256102, US2007/0185087, WO 08/021038, US2008/0045501, WO 08/063525, US2008/0167292, WO 07/113212, EP1644376, US2005/0032839, WO 05/005427, WO 06/070192, WO 06/070198, WO 06/070202, WO 06/070195, WO 06/003440, WO 05/002576, WO 05/002552, WO 04/071507, WO 04/058781, WO 06/055528, WO 06/055561, WO 05/118544, WO 05/013996, WO 06/036266, US2006/0160874, US2007/0142368, WO 04/043953, WO 07/132220, WO 07/132221, WO 07/132228, WO 04/00833 and WO 07/056164; and pharmaceutically acceptable salts thereof.

If a pharmaceutically acceptable salt of the Aurora kinase inhibitor is utilized in these compositions, the salt preferably is derived from an inorganic or organic acid or base. For reviews of suitable salts, see, e.g., Berge et al, *J. Pharm. Sci.* 66:1-19 (1977) and *Remington: The Science and Practice of Pharmacy*, 20th Ed., ed. A. Gennaro, Lippincott Williams & Wilkins, 2000.

Nonlimiting examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Suitable base addition salts include, without limitation, ammonium salts, alkali metal salts, such as sodium and potassium salts, alkaline earth metal salts, such as calcium and magnesium salts, salts with organic bases, such as dicyclohexylamine, N-methyl-D-glucamine, t-butylamine, ethylene diamine, ethanolamine, and choline, and salts with amino acids such as arginine, lysine, and so forth.

Also, basic nitrogen-containing groups may be quaternized with such agents as lower alkyl halides, such as methyl, ethyl, propyl, and butyl chlorides, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The term "pharmaceutically acceptable carrier" is used herein to refer to a material that is compatible with a recipient subject, preferably a mammal, more preferably a human, and is suitable for delivering an active agent to the target site without terminating the activity of the agent. The toxicity or adverse effects, if any, associated with the carrier preferably are commensurate with a reasonable risk/benefit ratio for the intended use of the active agent.

The terms "carrier", "adjuvant", or "vehicle" are used interchangeably herein, and include any and all solvents, diluents, and other liquid vehicles, dispersion or suspension aids, surface active agents, isotonic agents, thickening or emulsifying agents, preservatives, solid binders, lubricants and the like, as suited to the particular dosage form desired. *Remington: The Science and Practice of Pharmacy, 20th Ed.*, ed. A. Gennaro, Lippincott Williams & Wilkins, 2000 discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as disodium hydrogen phosphate, potassium hydrogen phosphate, sodium carbonate, sodium bicarbonate, potassium carbonate, potassium bicarbonate, magnesium hydroxide and aluminum hydroxide, glycine, sorbic acid, or potassium sorbate, partial glyceride mixtures of saturated vegetable fatty acids, water, pyrogen-free water, salts or electrolytes such as protamine sulfate, disodium hydrogen phosphate, potassium hydrogen phosphate, sodium chloride, and zinc salts, colloidal silica, magnesium trisilicate, polyvinyl pyrrolidone, polyacrylates, waxes, polyethylene-polyoxypropylene-block polymers, wool fat, sugars such as lactose, glucose, sucrose, starches such as corn starch and potato starch, cellulose and its derivatives such as sodium carboxymethyl cellulose, ethyl cellulose and cellulose acetate, powdered tragacanth; malt, gelatin, talc, excipients such as cocoa butter and suppository waxes, oils such as peanut oil, cottonseed oil, safflower oil, sesame oil, olive oil, corn oil and soybean oil, glycols such as propylene glycol and polyethylene glycol, esters such as ethyl oleate and ethyl laurate, agar, alginic acid, isotonic saline, Ringer's solution, alcohols such as ethanol, isopropyl alcohol, hexadecyl alcohol, and glycerol, cyclodextrins, lubricants such as sodium lauryl sulfate and magnesium stearate, petroleum hydrocarbons such as mineral oil and petrolatum. Coloring agents, releasing agents, coating agents, sweetening, flavoring and perfuming agents, preservatives and antioxidants can also be present in the composition, according to the judgment of the formulator.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain solvents, diluents, and other liquid vehicles, dispersion or suspension aids, surface active agents, pH modifiers, isotonic agents, thickening or emulsifying agents, stabilizers and preservatives, solid binders, lubricants and the like, as suited to the particular dosage form desired.

According to a preferred embodiment, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intravenously, or subcutaneously. The formulations of the invention may be designed to be short-acting, fast-releasing, or long-acting. Still further, compounds can be administered in a local rather than systemic means, such as administration (e.g., by injection) at a tumor site.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, cyclodextrins, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Compositions formulated for parenteral administration may be injected by bolus injection or by timed push, or may be administered by continuous infusion.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or Vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents such as phosphates or carbonates.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredients) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredients) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Formulation of an antibody or fragment to be administered will vary according to the route of administration and formulation (e.g., solution, emulsion, capsule) selected. An appropriate pharmaceutical composition comprising an antibody or functional fragment thereof to be administered can be prepared in a physiologically acceptable vehicle or carrier. A mixture of antibodies and/or fragments can also be used. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. A variety of appropriate aqueous carriers are known to the skilled artisan, including water, buffered water, buffered saline, polyols (e.g., glycerol, propylene glycol, liquid polyethylene glycol), dextrose solution and glycine. Intravenous vehicles can include various additives, preservatives, or fluid, nutrient or electrolyte replenishers (See, generally, *Remington's Pharmaceutical Science*, 16th Edition, Mack, Ed. 1980). The compositions can optionally contain pharmaceutically acceptable auxiliary substances as required to approximate physiological conditions such as pH adjusting and buffering agents and toxicity adjusting agents, for example, sodium acetate, sodium chloride, potassium chloride, calcium chloride and sodium lactate. The antibodies and fragments of this invention can be lyophilized for storage and reconstituted in a suitable carrier prior to use according to art-known lyophilization and reconstitution techniques. The optimum concentration of the active ingredient(s) in the chosen medium can be determined empirically, according to procedures well known to the skilled artisan, and will depend on the ultimate pharmaceutical formulation desired. For inhalation, the antibody or fragment can be solubilized and loaded into a suitable dispenser for administration (e.g., an atomizer, nebulizer or pressurized aerosol dispenser).

The antibody or fragment can be administered in a single dose or multiple doses. The dosage can be determined by methods known in the art and is dependent, for example, upon the antibody or fragment chosen, the subject's age, sensitivity and tolerance to drugs, and overall well-being. Antibodies and antigen-binding fragments thereof, such as human, humanized and chimeric antibodies and antigen-binding fragments can often be administered with less frequency than other types of therapeutics. For example, an effective amount of an antibody can range from about 0.01 mg/kg to about 5 or 10 mg/kg administered daily, weekly, biweekly or monthly.

The present invention provides new combination therapies for the treatment of hematological malignancies. As used herein, the term "hematological malignancies" includes any malignancy associated with cells in the bloodstream; bone marrow; and the lymphoid system including in the liver, spleen, and lymph nodes. Nonlimiting examples of hematological malignancies include B and T cell lymphomas and leukemias. Nonlimiting examples of B and T cell lymphomas include, for example, low grade/follicular non-Hodgkin's lymphoma (NHL), small lymphocytic (SL) NHL, T or B prolymphocytic leukemia, diffuse large B cell NHL, peripheral T cell lymphomas, mantle cell lymphoma, marginal zone lymphomas, B or T cell lymphoblastic lymphoma, Burkitt's lymphoma, primary thyroid lymphoma, Waldenstrom's Macroglobulinemia or lymphoplasmacytic lymphoma. Nonlimiting examples of leukemia include, for example, chronic leukocytic leukemia, acute myelogenous leukemia (AML), acute lymphoblastic leukemia, chronic lymphocytic leukemia (CLL), chronic myelogenous leukemia, lymphoblastic leukemia, lymphocytic leukemia, monocytic leukemia, myelogenous leukemia and promyelocytic leukemia. Nonlimiting examples of hematological malignancies additionally include, for example, multiple myeloma, myelodysplastic syndromes (MDS), including refractory anemia (RA), refractory anemia with ringed sideriblasts (RARS), (refractory anemia with excess blasts (RAEB), and RAEB in transformation (RAEB-T); and myeloproliferative syndromes. It should be clear to those of skill in the art that these pathological conditions may often have different names due to differing/changing classification systems.

In some embodiments, the hematological malignancy to be treated by the method of the invention is one in which the activity of an Aurora kinase is amplified and in which the CD20 antigen is expressed. In some embodiments, the hematological malignancy is selected from the group consisting of lymphoma, leukemia and multiple myeloma. In certain embodiments, the lymphoma is selected from the group consisting of B cell lymphoma, non-Hodgkin's lymphoma and mantle cell lymphoma.

The term "patient", as used herein, means an animal, preferably a mammal, more preferably a human. In some embodiments, the patient has been treated with an agent, e.g., an Aurora kinase inhibitor or an anti-CD20 antibody, prior to initiation of treatment according to the method of the invention. In some embodiments, the patient is a patient at risk of developing or experiencing a recurrence of a hematological malignancy.

The expression "therapeutically effective amount" refers to an amount of a drug substance (e.g., Aurora kinase inhibitor and/or anti-CD20 antibody) effective for treatment or prophylaxis or amelioration of symptoms of a hematological malignancy discussed herein.

Compositions for use in the method of the invention may be formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present invention will be decided by the attending physician within the scope of sound medical judgment. A unit dosage form for parenteral administration may be in ampoules or in multi-dose containers.

The Aurora kinase inhibitor may be administered with the anti-CD20 antibody in a single dosage form or as a separate dosage form. When administered as a separate dosage form, the anti-CD20 antibody may be administered prior to, at the same time as, or following administration of the Aurora kinase inhibitor of the invention.

As specifically contemplated herein, the instant invention includes the following methods: A method to treat a patient suffering from a hematological malignancy comprising administering to said patient a therapeutically effective amount of a Aurora kinase inhibitor simultaneously with or consecutively with (e.g., before or after) an anti-CD20 antibody; A method to treat a patient suffering from a hematological malignancy comprising administering to said patient a therapeutically effective amount of a Aurora kinase inhibitor simultaneously with or consecutively with (e.g. before or after) rituximab; A method to treat a patient suffering from lymphoma comprising administering to said patient a therapeutically effective amount of a Aurora kinase inhibitor simultaneously with or consecutively with (e.g. before or after) an anti-CD20 antibody; A method to treat a patient suffering from lymphoma comprising administering to said patient a therapeutically effective amount of a Aurora kinase inhibitor simultaneously with or consecutively with (e.g. before or after) rituximab; A method to treat a patient suffering from leukemia comprising administering to said patient a therapeutically effective amount of a Aurora kinase inhibitor simultaneously with or consecutively with (e.g. before or after) an anti-CD20 antibody; A method to treat a patient suffering from leukemia comprising administering to said patient a therapeutically effective amount of a Aurora kinase inhibitor simultaneously with or consecutively with (e.g. before or after) rituximab; A method to treat a patient suffering from multiple myeloma comprising administering to said patient a therapeutically effective amount of a Aurora kinase inhibitor simultaneously with or consecutively with (e.g. before or after) an anti-CD20 antibody; and A method to treat a patient suffering from multiple myeloma comprising administering to said patient a therapeutically effective amount of a Aurora kinase inhibitor simultaneously with or consecutively with (e.g. before or after) rituximab.

In some particular embodiments, the method of the invention comprises administering to a patient suffering from a hematological malignancy a therapeutically effective amount of an Aurora kinase inhibitor of Formula (I), (II) or (III) as defined herein simultaneously with or consecutively with (e.g., before or after) rituximab.

Additionally, the invention relates to use of an Aurora kinase inhibitor for the manufacture of a medicament for the treatment of a hematological malignancy. In other particular embodiments, the invention relates to the use of an Aurora kinase inhibitor of Formula (I), (II) or (III) as defined herein, in the manufacture of a medicament for use in combination therapy with rituximab for the treatment of a hematological malignancy.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices and materials are herein described. All publications mentioned herein are hereby incorporated by reference in their entirety for the purpose of describing and disclosing the materials and methodologies that are reported in the publication which might be used in connection with the invention.

EXAMPLES

Definitions

| | |
|---|---|
| ANOVA | Analysis of variance |
| ΔAUC | difference in the area under the curve |
| BID | twice daily |
| DLBCL | diffuse large B-cell lymphoma |
| IV | intravenous(ly) |
| MTD | maximum tolerated dose |
| SCID | severe combined immunodeficiency |
| po. | Orally (by mouth, per os) |
| QD | once daily |
| QW or Q7D | once weekly |
| SC | subcutaneous(ly) |
| TG | treatment group |
| TGI | tumor growth inhibition |

Experimental Overview

The Ly19-Luc, WSU-DLBCL2-Luc and PHTX-22-06 models described in these studies are human DLBCL cell lines, transfected with luciferase. These models were grown in immununocomprimised mice subcutaneously on the flank, or disseminated throughout the body by tail vain injection. 4-{[9-chloro-7-(2-fluoro-6-methoxyphenyl)-5H-pyrimido[5,4-d][2]benzazepin-2-yl]amino}-2-methoxybenzoic acid (III-1) was administered orally in both daily and twice daily dosing regimens and rituximab was administered by IV injection QD7×3. The efficacy, tumor growth and post-treatment survival of mice treated with Compound III-1 and rituximab were compared as single agents or in combination.

Sub-Cutaneous Models

Example 1: Combination of Aurora a Kinase Specific Inhibitor (Compound III-1) and Rituximab in a Sub-Cutaneous Ly19 Lymphoma Model Grown in Female SCID Mice Experimental Overview This is an in vivo experiment looking at tumor volume after treatment with the combination of Compound III-1 and rituximab. Tumor growth was monitored with vernier calipers. The mean tumor volume was calculated using the formula $V=W^2 \times L/2$. When the mean tumor volume reached approximately 200 mm$^3$, the animals were randomized into the following eight treatment groups, with each cohort made up of ten mice:

Vehicle
3 mg/kg Compound III-1 (qd)
10 mg/kg Compound III-1 (qd)
10 mg/kg Compound III-1 (bid)
10 mg/kg rituximab (qw)
3 mg/kg Compound III-1 (qd)+10 mg/kg rituximab (qw)
10 mg/kg Compound III-1 (qd)+10 mg/kg rituximab (qw)
10 mg/kg Compound III-1 (bid)+10 mg/kg rituximab (qw)

The animals were inoculated with $4.0 \times 10^6$ cells from cell line Ly-19 at implant site Flank (cell suspension). Compounds were administered for 21 days, and tumor volumes were measured on days 0, 5, 13, 15, 18, and 21. After treatment ended, the surviving mice continued to be evaluated on days 25, 28, 33, 36, 40, 43, 47, 50, 54, 60, and 62.

There were several endpoints in this experiment. The primary goal was to determine whether the combination of Compound III-1 and rituximab was more effective at reducing tumor volume than either treatment alone. The second endpoint was to evaluate the rates of tumor regrowth among the groups after treatment was completed.

Statistical Methodology

Statistical analysis was performed using a linear mixed effects regression model. This model takes into account the differences in trends of tumor growth between control and treated samples. The statistical modeling was conducted in two steps: model fitting and model selection. In the first step, a family of ten closely related mixed-effects regression models was fitted to the study data. Data from all time points in the study were used, including mice that were sacrificed before the end of the study. Each treatment group was fitted to a quadratic trend line for tumor growth that consisted of up to three terms for tumor growth: zero-order (intercept), first-order (slope) and second-order (curvature). Each drug treatment was then modeled by up to two interaction terms, one describing the difference in slope and the other describing the difference in curvature due to drug treatments. In addition, mouse-specific variability was accounted for by including random effects for each mouse with up to three terms: a mouse-specific intercept, slope or curvature effect. Repeated measurements of tumor growth for a given mouse were modeled using a compound symmetry covariance structure.

Model selection was performed by first filtering models that the model-fitting algorithm was unable to fit in a numerically stable way (specifically by removing models that demonstrated sensitivity to the starting value of the autocorrelation coefficient, and those for whom the variance-covariance matrix of random effects was not positive definite). The best fit model was then selected using a statistical criterion called the Bayes Information Criterion (BIC), which is a measure of a model's goodness of fit that takes into account the number of parameters used by the model and the magnitude of the residuals—the difference between fitted and observed values. The BIC favors models that are parsimonious and that fit the underlying data well.

The model fitting and selection procedure were performed twice, once on the original (untransformed) data, and once on $\log_{10}$-transformed data. Once the automated model-fitting and selection procedure were completed, two best-fit models were generated, one on log-transformed data and the other on untransformed data. An investigator then studied the diagnostic plots generated by the two statistical models and chose one of them as the appropriate model for the study. This choice was made on the basis of the distribution of the residuals as well as their behavior with respect to the fitted values. Obvious trends in the residuals were indicative of a poor model fit, suggesting trends remaining in the data that the model had failed to take into account.

Once an appropriate statistical model was selected, the effect size was calculated as the difference between areas under the model-fitted curves ($\Delta$AUC) for treated and control groups, relative to the area under the model-fitted curve for the control group. A $\Delta$AUC of 0 meant that the curves for the treatment and control groups were the same, whereas a negative $\Delta$AUC indicated tumor growth inhibition upon treatment.

The significance of an effect size for a given pairwise comparison was assessed using permutation analysis. During this procedure, the assignment of mice to treatment and control groups were randomly shuffled. The $\Delta$AUC metric was calculated for comparisons between these new simulated groups, and the process was repeated ~2000 times. This gave rise to an empirical distribution of the $\Delta$AUC values for the null hypothesis, which stated that there was no difference in $\Delta$AUC values between treatment and control groups. The reported p-value was the proportion of permuted $\Delta$AUC values which were greater than the $\Delta$AUC of the original group assignments. P-values <0.05 were considered significant.

For combination studies a synergy measure was also reported (in addition to the measures of tumor growth inhibition for each arm of the trial relative to control). For the synergy measure, the approach and the results described here were essentially equivalent, except that effect size was defined differently and permutation testing was performed over four groups rather than two. The effect size for combinations was defined as: $\Delta\text{AUC}=[\text{AUC}_{A \times B}-\text{AUC}_{ctl}-(\text{AUC}_A-\text{AUC}_{ctl}+\text{AUC}_B-\text{AUC}_{ctl})]/\text{AUC}_{ctl}$ (where A×B is the combination treatment, ctl is the control, and A and B are the agents used singly). A $\Delta$AUC of less than zero meant that a combination treatment led to a greater decrease in area under the curve than the sum of individual treatments, indicating a synergistic tumor growth inhibition. Permutation testing was performed to compare the difference between control and combination treatment against the difference that would have been observed if the treatments were purely additive. Synergy measures disclosed herein are provided based on $\Delta$AUC calculations and based on TGI calculations. Because $\Delta$AUC calculations capture the entire treatment period within an experiment, such calculations are deemed more comprehensive and more accurate than the TGI calculations.

Results

In this study, all animals in all of the treatment groups endured the 21 days of treatment.

The average tumor volume in the vehicle group increased almost sixteen fold from 180 mm$^3$ at day 0 to over 2850 mm$^3$ on day 21, and this resulted in a mean area under the log(fold change) over time curve (AUC) of 12.9. The AUCs, and therefore the tumor volumes, were smaller in each of the treatment groups compared to vehicle (Table 3a). The results of the linear regression model revealed that all of these differences relative to the vehicle group were significant (Table 3b).

TABLE 3a

Efficacy Analysis (Days 0 through 21)

| Treatment | Pct Decrease in AUC Relative to Mean Vehicle AUC |
| --- | --- |
| Vehicle | — |
| Compound III-1 (3 mg/kg qd) | 22.9 |
| Compound III-1 (10 mg/kg qd) | 79.3 |
| Compound III-1 (10 mg/kg bid) | 105.6 |
| Rituximab (10 mg/kg) | 71.8 |
| Compound III-1 (3 mg/kg qd) + Rituximab (10 mg/kg) | 130.0 |
| Compound III-1 (10 mg/kg qd) + Rituximab (10 mg/kg) | 151.4 |
| Compound III-1 (10 mg/kg bid) + Rituximab (10 mg/kg) | 186.2 |

Average percent change in the area under the log$_{10}$ fold change vs day curves (AUC) relative to the mean AUC of the vehicle group.

TABLE 3b

Efficacy Analysis (Days 0 through 21)

| Treatment Group | Reference | P-value |
| --- | --- | --- |
| Compound III-1 (3 mg/kg qd) | Vehicle | <0.01 |
| Compound III-1 (10 mg/kg qd) | | <0.01 |
| Compound III-1 (10 mg/kg bid) | | <0.01 |
| Rituximab (10 mg/kg) | | <0.01 |
| Compound III-1 (3 mg/kg qd) + Rituximab (10 mg/kg) | | <0.01 |
| Compound III-1 (10 mg/kg qd) + Rituximab (10 mg/kg) | | <0.01 |
| Compound III-1 (10 mg/kg bid) + Rituximab (10 mg/kg) | | <0.01 |
| Compound III-1 (3 mg/kg) + Rituximab (10 mg/kg) | Compound III-1 (3 mg/kg) | <0.01 |
| | Rituximab (10 mg/kg) | <0.01 |
| Compound III-1 (10 mg/kg qd) + Rituximab (10 mg/kg) | Compound III-1 (10 mg/kg qd) | <0.01 |
| | Rituximab (10 mg/kg) | <0.01 |
| Compound III-1 (10 mg/kg bid) + Rituximab (10 mg/kg) | Compound III-1 (10 mg/kg bid) | <0.01 |
| | Rituximab (10 mg/kg) | <0.01 |

Summary of mixed-effects linear regression results.

The three combination groups showed consistent decreases in tumor volume and were all significantly lower than their respective single agents alone. The Compound III-1 (3 mg/kg qd)+rituximab (10 mg/kg) group was synergistic, while the other two combinations were additive when examining AUC values (Table 4). All three combinations were sub-additive when looking at tumor growth inhibition (Table 5, Table 6).

TABLE 4

Synergy Analysis (AUC, Days 0 through 21)

| Combination | Synergy Score | 95% Confidence Interval | Assessment |
| --- | --- | --- | --- |
| Compound III-1 (3 mg/kg qd) + Rituximab (10 mg/kg) | −0.35 | (−0.55, −0.15) | Synergistic |
| Compound III-1 (10 mg/kg qd) + Rituximab (10 mg/kg) | 0.00 | (−0.19, 0.18) | Additive |
| Compound III-1 (10 mg/kg bid) + Rituximab (10 mg/kg) | −0.09 | (−0.32, 0.14) | Additive |

Synergistic: score < 0, Additive: score = 0, Sub-additive: score > 0. Assessment based on whether 95% confidence interval included the value 0.

TABLE 5

Tumor Growth Inhibition (Day 21)

| Treatment | Pct Tumor Growth Inhibition Relative to Vehicle Mean |
| --- | --- |
| Vehicle | — |
| Compound III-1 (3 mg/kg qd) | 54.7 |
| Compound III-1 (10 mg/kg qd) | 97.1 |
| Compound III-1 (10 mg/kg bid) | 102.2 |
| Rituximab (10 mg/kg) | 94.5 |
| Compound III-1 (3 mg/kg qd) + Rituximab (10 mg/kg) | 103.7 |
| Compound III-1 (10 mg/kg qd) + Rituximab (10 mg/kg) | 105.3 |
| Compound III-1 (10 mg/kg bid) + Rituximab (10 mg/kg) | 105.8 |

Average percent decrease in tumor growth relative to the mean tumor volume of the vehicle group.

TABLE 6

Synergy Analysis (Tumor Growth Inhibition, Day 21)

| Combination | Synergy Score | 95% Confidence Interval | Assessment |
| --- | --- | --- | --- |
| Compound III-1 (3 mg/kg qd) + Rituximab (10 mg/kg) | 0.46 | (0.35, 0.56) | Sub-Additive |
| Compound III-1 (10 mg/kg qd) + Rituximab (10 mg/kg) | 0.86 | (0.81, 0.91) | Sub-Additive |
| Compound III-1 (10 mg/kg bid) + Rituximab (10 mg/kg) | 0.91 | (0.86, 0.96) | Sub-Additive |

Synergistic: score < 0, Additive: score = 0, Sub-additive: score > 0. Assessment based on whether 95% confidence interval included the value 0.

To determine if tumors began to regrow after treatment ended, mixed-effects piecewise linear regression models were built to compare the slope of the log tumor volume between days 9 and day 21 to the slope between days 21 and 62 (or earlier if all animals in a group died). All of the examined groups showed increases in slope after treatment which were at least marginally significant (Table 7), suggesting that tumor volumes stopped shrinking or, in the cases of Compound III-1 (10 mg/kg qd) and rituximab (10 mg/kg), began to grow again.

TABLE 7

Difference in Tumor Growth Rates

| Treatment Group | Change in Slope | P-value |
|---|---|---|
| Compound III-1 (10 mg/kg qd) | 0.040 | 0.05 |
| Compound III-1 (10 mg/kg bid) | 0.018 | <0.01 |
| Rituximab (10 mg/kg) | 0.039 | <0.01 |
| Compound III-1 (3 mg/kg qd) + Rituximab (10 mg/kg) | 0.012 | 0.02 |
| Compound III-1 (10 mg/kg qd) + Rituximab (10 mg/kg) | 0.053 | <0.01 |
| Compound III-1 (10 mg/kg bid) + Rituximab (10 mg/kg) | 0.091 | <0.01 |

Breakpoint was set at day 21. Change in slope was calculated as slope (day 21 to 62) − slope (day 13 to 21). P-values < 0.05 indicate that the difference in slope was significantly different than zero.

Conclusions

The effects of Compound III-1 in combination with rituximab upon tumor volumes were investigated in an in vivo sub-cutaneous xenograft study. 3 mg/kg Compound III-1 dosed qd, 10 mg/kg Compound III-1 dosed qd, and 10 mg/kg Compound III-1 dosed bid were administered as both single agents and in combination with 10 mg/kg of rituximab. All treatment groups had significantly lower mean areas under the log(fold change) vs time curves relative to the vehicle group during the first 21 days. Additionally, the mean AUC of the 3 mg/kg Compound III-1 rituximab combination group was significantly lower than that for the respective individual treatment groups. Surprisingly, the combination of Compound III-1 with rituximab was demonstrated to have a synergistic therapeutic effect in this sub-cutaneous lymphoma model. Once treatment was completed, tumor volumes ceased to continue diminishing, and in some cases began to regrow.

Example 2: Combination of Aurora a Kinase Specific Inhibitor (Compound III-1) and Rituximab in a Subcutaneous WSU-Luc Lymphoma Model Grown in Female SCID Mice Experimental Overview This is an in vivo experiment looking at tumor volume after treatment with the combination of Compound III-1 and rituximab. Tumor growth was monitored with vernier calipers. The mean tumor volume was calculated using the formula $V=W^2 \times L/2$. When the mean tumor volume reached approximately 250 mm$^3$, the animals were randomized into the following six treatment groups, with each group made up of ten mice:

Vehicle
3 mg/kg Compound III-1 (P.O., qd)
10 mg/kg Compound III-1 (P.O., qd)
10 mg/kg rituximab (I.V., q7d)
3 mg/kg Compound III-1+10 mg/kg rituximab
10 mg/kg Compound III-1+10 mg/kg rituximab The animals were inoculated with $4.0 \times 10^6$ cells from cell line WSU-DLCL2 at implant site Flank (cell suspension). Compounds were administered for 21 days, and tumor volumes were measured on days 0, 4, 7, 11, 15, 18, and 20. The primary goal was to investigate whether the combination of Compound III-1 and Rituximab was synergistic.

Statistical Methodology

The statistical methodology used in these experiments was the same as that described in Example 1 above.

Results

The average tumor volume in the vehicle group increased over nine-fold from 201 mm$^3$ at day 0 to 1903 mm$^3$ on day 20. The tumor volumes were smaller in each of the treatment groups compared to vehicle (Table 8).

TABLE 8

Efficacy Analysis (Days 0 through 20)

| Treatment | Pct Decrease in AUC Relative to Mean Vehicle AUC |
|---|---|
| Vehicle | — |
| Compound III-1 (3 mg/kg, PO, qd) | 19.4 |
| Compound III-1 (10 mg/kg, PO, qd) | 48.5 |
| Rituximab (10 mg/kg, IV, q7d) | 43.2 |
| Compound III-1 (3 mg/kg) + Rituximab (10 mg/kg, IV, q7d) | 60.5 |
| Compound III-1 (10 mg/kg) + Rituximab (10 mg/kg, IV, q7d) | 86.6 |

Average percent change in the area under the $\log_{10}$ fold change vs day curves (AUC) relative to the mean AUC of the vehicle group.

Both combination groups were additive relative to their respective individual treatments when comparing AUC values (Table 9).

TABLE 9

Synergy Analysis of AUC values (Days 0 through 20)

| Combination | Synergy Score | Approx. 95% Confidence Interval | Assessment |
|---|---|---|---|
| Compound III-1 (3 mg/kg) + Rituximab (10 mg/kg, IV, q7d) | 0.02 | (−0.12, 0.16) | Additive |
| Compound III-1 (10 mg/kg) + Rituximab (10 mg/kg, IV, q7d) | 0.05 | (−0.08, 0.18) | Additive |

Synergistic: score < 0, Additive: score = 0, Sub-additive: score > 0. Assessment based on whether 95% confidence interval included the value 0

Both treatment groups were sub-additive when looking at tumor growth inhibition (Table 10, and Table 11).

TABLE 10

Tumor Growth Inhibition (Day 20)

| Treatment | Pct Tumor Growth Inhibition Relative to Vehicle Mean |
|---|---|
| Vehicle | — |
| Compound III-1 (3 mg/kg, PO, qd) | 33.1 |
| Compound III-1 (10 mg/kg, PO, qd) | 68.9 |
| Rituximab (10 mg/kg, IV, q7d) | 67.1 |
| Compound III-1 (3 mg/kg) + Rituximab (10 mg/kg, IV, q7d) | 78.5 |
| Compound III-1 (10 mg/kg) + Rituximab (10 mg/kg, IV, q7d) | 95.5 |

Average percent decrease in tumor growth relative to the mean tumor volume of the vehicle group.

TABLE 11

Synergy Analysis of Tumor Growth Inhibition (Day 20)

| Combination | Synergy Score | Approx. 95% Confidence Interval | Assessment |
| --- | --- | --- | --- |
| Compound (3 mg/kg) + Rituximab (10 mg/kg, IV, q7d) | 0.21 | (0.08, 0.35) | Sub-Additive |
| Compound (10 mg/kg) + Rituximab (10 mg/kg, IV, q7d) | 0.40 | (0.30, 0.51) | Sub-Additive |

Synergistic: score < 0, Additive: score = 0, Sub-additive: score > 0. Assessment based on whether 95% confidence interval included the value 0.

Conclusions

The effects of Compound III-1 in combination with rituximab upon tumor volumes were investigated in an in vivo sub-cutaneous xenograft study. 3 mg/kg and 10 mg/kg Compound III-1, dosed PO and qd, and 10 mg/kg rituximab, dosed IV and q7d, were administered as both single agents and in combination. Neither combination group showed a synergistic interaction relative to their respective single agents when looking at AUC or tumor growth inhibition.

Example 3: Combination of Aurora a Kinase Specific Inhibitor (Compound III-1) and Rituximab in a Sub-Cutaneous Primary Diffuse Large B-Cell Lymphoma Model (PHTX-22-06) Grown in Female SCID Mice Experimental Overview This is an in vivo experiment looking at tumor volume after treatment with the combination of Compound III-1, and rituximab. Tumor growth was monitored with vernier calipers. The mean tumor volume was calculated using the formula $V = W^2 \times L/2$. When the mean tumor volume reached approximately 200 mm$^3$, the animals were randomized into the following six treatment groups, with each group made up of ten mice:

Vehicle 10 mg/kg Compound III-1 (P.O., bid)

20 mg/kg Compound III-1 (P.O., bid)

10 mg/kg rituximab (I.V., q7d)

10 mg/kg Compound III-1 + 10 mg/kg rituximab 20 mg/kg Compound III-1 + 10 mg/kg rituximab The animals were inoculated with 2×5 mm$^3$ tumor mass from primary PHTX-22L-6 tumor chunk at implant site Flank (trocar). Compounds were administered for 21 days, and tumor volumes taken on days 0, 3, 7, 10, 14, 17, 21, 24, and 27 were analyzed. The primary goal was to investigate whether the combination of Compound III-1 and rituximab was synergistic.

Statistical Methodology

The statistical methodology used in these experiments was the same as that described in Example 1 above.

Results

The average tumor volume in the vehicle group increased over nine-fold from 268 mm$^3$ at day 0 to 2563 mm$^3$ on day 27. The tumor volumes were smaller in each of the treatment groups compared to vehicle (Table 12).

TABLE 12

Efficacy Analysis (Days 0 through 27)

| Treatment | Pct Decrease in AUC Relative to Mean Vehicle AUC |
| --- | --- |
| Vehicle | — |
| Compound III-1 (10 mg/kg, PO, bid) | 52.3 |
| Compound III-1 (20 mg/kg, PO, bid) | 79.3 |
| Rituximab (10 mg/kg, IV, q7d) | 41.9 |
| Compound III-1 (10 mg/kg) + Rituximab (10 mg/kg, IV, q7d) | 75.8 |
| Compound III-1 (20 mg/kg) + Rituximab (10 mg/kg, IV, q7d) | 146.8 |

Average percent change in the area under the log$_{10}$ fold change vs day curves (AUC) relative to the mean AUC of the vehicle group.

Both combinations groups were additive relative to their respective individual treatments when comparing AUC values (Table 13).

TABLE 13

Synergy Analysis of AUC values (Days 0 through 27)

| Combination | Synergy Score | Approx. 95% Confidence Interval | Assessment |
| --- | --- | --- | --- |
| Compound III-1 (3 mg/kg) + Rituximab (10 mg/kg, IV, q7d) | 0.18 | (−0.05, 0.42) | Additive |
| Compound III-1 (10 mg/kg) + Rituximab (10 mg/kg, IV, q7d) | −0.26 | (−0.80, 0.29) | Additive |

Synergistic: score < 0, Additive: score = 0, Sub-additive: score > 0. Assessment based on whether 95% confidence interval included the value 0.

Both treatment groups were sub-additive when looking at tumor growth inhibition (Table 14, and Table 15).

TABLE 14

Tumor Growth Inhibition (Days 0 through 27)

| Treatment | Pct Tumor Growth Inhibition Relative to Vehicle Mean |
| --- | --- |
| Vehicle | — |
| Compound III-1 (10 mg/kg, PO, bid) | 86.3 |
| Compound III-1 (20 mg/kg, PO, bid) | 95.1 |
| Rituximab (10 mg/kg, IV, q7d) | 57.3 |
| Compound III-1 (10 mg/kg) + Rituximab (10 mg/kg, IV, q7d) | 97.3 |
| Compound III-1 (20 mg/kg) + Rituximab (10 mg/kg, IV, q7d) | 105.1 |

Average percent decrease in tumor growth relative to the mean tumor volume of the vehicle group.

TABLE 15

Synergy Analysis of Tumor Growth Inhibition (Days 0 through 27)

| Combination | Synergy Score | Approx. 95% Confidence Interval | Assessment |
| --- | --- | --- | --- |
| Compound III-1 (10 mg/kg) + Rituximab (10 mg/kg, IV, q7d) | 0.46 | (0.26, 0.67) | Sub-Additive |

TABLE 15-continued

Synergy Analysis of Tumor Growth Inhibition (Days 0 through 27)

| Combination | Synergy Score | Approx. 95% Confidence Interval | Assessment |
|---|---|---|---|
| Compound III-1 (20 mg/kg) + Rituximab (10 mg/kg, IV, q7d) | 0.47 | (0.27, 0.68) | Sub-Additive |

Synergistic: score < 0, Additive: score = 0, Sub-additive: score > 0. Assessment based on whether 95% confidence interval included the value 0.

Conclusions:

The effects of Compound III-1 in combination with rituximab upon tumor volumes were investigated in an in vivo sub-cutaneous xenograft study. 10 mg/kg and 20 mg/kg Compound III-1, dosed PO and bid, and 10 mg/kg rituximab, dosed IV and q7d, were administered as both single agents and in combination. Neither combination examined showed a synergistic interaction relative to their respective single agents when looking at AUC or tumor growth inhibition, which may be attributable to the significant single agent activity observed in this model.

Disseminated Models

Example 4: Combination of Aurora a Kinase Specific Inhibitor (Compound III-1) and Rituximab in a Disseminated Lymphoma Model of Ly19-Luc Cell Line Grown in Female SCID Mice Experimental Overview The in vivo experiments using the disseminated Ly19-Luc lymphoma model were performed in duplicate. The experiments consisted of looking at tumor volume after treatment with the combination of Compound III-1 and rituximab. Tumor volumes were estimated once weekly throughout the inoculation and treatment period using the Xenogen IVIS® imaging system (Xenogen Corporation, Alameda, Calif.). To image the mice, an intraperitoneal (IP) injection of luciferase (15 mg/ml), was administered 10 minutes prior to procedure and mice were anesthetized with 2% isofluorane 2-5 minutes throughout the scanning procedure. For Xenogen imaging, each mouse was imaged on dorsal and ventral views. The sum of 2 photon flux measurements was used for the analysis.

The antitumor effects of each treatment group were determined by calculating the percent TGI ([Δ control mean tumor volume−Δ treated mean tumor volume]×100/Δ control mean tumor volume) at the end of treatment. Mice were weighed once weekly for the duration of the study and the maximal percent body weight change was determined during the treatment period. Animals were monitored for survival up to 132 days following treatment. Animals were removed from the study when they reached humane endpoints (>20%, body weight loss or paralysis of either both front or hind limbs), the medial survival for each group was determined and the survival rate of treatment groups were compared to control. Treatment groups were evaluated to determine if the effects of combination treatment were synergistic, additive or sub-additive relative to control.

Statistical Analysis

Tumor Growth Inhibition (TGI):

The photon flux data was $\log_{10}$ transformed, and these values over the treatment period were compared across treatment groups to assess if the differences in the trends over time were statistically significant. A mixed-effects linear regression model using a restricted maximum likelihood was fit to the data. An ANOVA test was performed to determine if there was a statistically significant difference between the treatment groups and control.

Area Under the Curve (AUC):

$\log_{10}$-transformed fold change photon flux values (tumor burden) from baseline were also used to calculate AUC values for each animal. The AUC values from the mice in a given treatment group were then averaged together to generate mean AUC values and associated standard errors.

Synergy Effects:

A synergy score calculation was used to address the question of whether the effects of the combination treatment were synergistic, additive, or sub-additive relative to the individual treatments. The effect of the combination treatment was considered synergistic if the synergy score was less than 0, additive if the synergy score equaled 0, and sub-additive if the synergy score was greater than 0. Standard errors and 95% confidence intervals (calculated as 2*SE) were used to determine if the synergy scores were significantly different from zero.

Tumor Regrowth:

To compare the tumor regrowth rates after stopping treatment, mixed-effects piecewise linear regression models were built separately for each treatment group with mice monitored beyond treatment period. All P-values <0.05 were called significant in this report.

Survival Rate:

The survival rates of the animals in each treatment group were plotted using Kaplan-Meier curves and the log rank test was used to compare survival rates among pairs of treatment groups.

Experiment #1: Disseminated Ly19-Luc Lymphoma Model

Animals bearing Ly19-Luc xenografts were treated with Compound III-1 and rituximab as single agents and in combination. The TGI, calculated on Day 24 was similar between treatment groups (89.6%-100.3%). Tumor growth was significantly inhibited in all single agent and combination treatment groups compared to vehicle (p<0.001, Table 16).

TABEL 16

Dosing regimen for mice in first disseminated Ly19 experimental group

| Study/ Treatment Group[a] | Dose (mg/kg)[b] | Route and Dose Regimen | Maximum Percent Body Weight Change (%) | TGI Mean[c] (%) | p Value[d] | Survival Median Survival (Days) | p Value[e] |
|---|---|---|---|---|---|---|---|
| Vehicle | 0 | Po/QD × 21 days | −5.9, Day 24 | N/A | N/A | 25 | N/A |
| Compound III-1 | 3 | Po/QD × 21 days | +6.2, Day 24 | 89.6, Day 24 | <0.001 | 40 | <0.001 |

TABEL 16-continued

Dosing regimen for mice in first disseminated Ly19 experimental group

| Study/ Treatment Group[a] | Dose (mg/kg)[b] | Route and Dose Regimen | Maximum Percent Body Weight Change (%) | TGI Mean[c] (%) | p Value[d] | Survival Median Survival (Days) | p Value[e] |
|---|---|---|---|---|---|---|---|
| Compound III-1 | 10 | Po/QD × 21 days | +3.3, Day 24 | 100, Day 24 | <0.001 | 63.5 | <0.001 |
| Compound III-1 | 3 | po/QD × 21 days | +8.7, Day 24 | 100, Day 24 | <0.001 | >100 | <0.001* |
| Rituximab | 10 | IV/QW × 3 doses | | | | | |
| Compound III-1 | 10 | po/QD × 21 days | +4.5, Day 24 | 100.3, Day 24 | <0.001 | >100 | <0.001* |
| Rituximab | 10 | IV/QW × 3 doses | | | | | |
| Rituximab | 10 | IV/QW × 3 doses | +9.4, Day 24 | 99.6, Day 24 | <0.001 | 66 | <0.001 |

[a]There were 10 mice in each treatment group.
[b]For each dose, mice received 100 µL of Compound III-1 and/or rituximab dosing solution prepared at 0.75, 2.5, 5.0 and 7.5 mg/mL (3, 10, 20, 30 mg/kg Compound III-1) or 2.0 mg/mL (10 mg/kg rituximab). These dosing solutions were prepared routinely based on historical mouse body weights of 25 or 20 grams respectively. All doses were approximate.
[c]Mean tumor volumes, and TGI values were calculated on Day 24 of treatment.
[d]TGI = TGI calculation B – tumor growth inhibition (TGI = [(Δ control average volume – Δ treated average volume) × 100/Δ control average volume]. p values were calculated with an ANOVA, $p < 0.05$ considered statistically significant. TGI values will be greater than 100% when the average volume of the treatment group is smaller at the end of treatment than at the beginning of treatment
[e]Log-rank analysis was used to compare the survival rate of each treatment group to the vehicle group test, $p < 0.05$ considered statistically significant. *= Combination treatment groups had significantly longer survival than the corresponding individual treatment groups ($p \leq 0.004$).
[f]Animals dosed with Compound III-1 at 10 mg/kg BID and 30 mg/kg QD received a 5 day dose holiday from Day 13 to Day 17.
[g]The vehicle used in TG1 and the treatment groups was 10% HP-β-CD plus 1% NaHCO$_3$. The vehicle used in the rituximab treatment groups was 0.9% saline Individual whole body bioluminescence images were taken of all mice in all treatment groups using the Xenogen IVIS® imaging system. Any bioluminescence observed in these whole body images represents tumor presence in the mouse model. Tumor presence/growth in each mouse was assessed using this system prior to treatment on Day 0; after the end of treatment on Day 24; and of mice remaining in the study on Day 52, On Day 24 there is a striking reduction in the fluorescent signal of the tumor as a result of treatment with Compound III-1 at 10 mg/kg, with the combination Compound III-1 at 3 mg/kg with rituximab and with the combination Compound III-1 at 10 mg/kg with rituximab. Mice receiving combination treatments show little or no evidence of the disseminated lymphoma tumor. At Day 52 however, tumor growth was evident in the mice remaining in the single agent Compound III-1 10 mg/kg and rituximab 10 mg/kg groups.

Photon flux values (tumor burden) from baseline to Day 24 were also used to calculate AUC values for each animal and the percent decrease in the AUC relative to the mean vehicle AUC was calculated (Table 17a). A synergy score calculation was applied to the AUC data to determine whether the effects of the combination treatment were synergistic, additive or sub-additive relative to the individual treatments. This analysis showed that the combination treatment of Compound III-1 at 3 mg/kg QD with rituximab at 10 mg/kg QW was synergistic when comparing the $\log_{10}$-transformed fold changes and the combination treatment of Compound III-1 at 10 mg/kg with rituximab at 10 mg/kg QW displayed an additive effect (Table 17b).

TABLE 17a

Average percent change in the area under the $\log_{10}$ fold change versus day curves (AUC) relative to the mean AUC of the vehicle group for each treatment group. Values greater than 100 indicate decreased tumor burden.

| Treatment | Percent Decrease in AUC Relative to Mean Vehicle AUC |
|---|---|
| Vehicle | N/A |
| Compound III-1 (3 mg/kg-QD) | 59.3 |
| Compound III-1 (10 mg/kg-QD) | 108.2 |
| Rituximab (10 mg/kg-QW) | 103.3 |
| Compound III-1 (3 mg/kg) + Rituximab (10 mg/kg) | 121.2 |
| Compound III-1 (10 mg/kg) + Rituximab (10 mg/kg) | 121.4 |

TABLE 17b

| Combination | Synergy Score | 95% Confidence Interval | Assessment |
|---|---|---|---|
| Compound III-1 (3 mg/kg) + Rituximab (10 mg/kg) | −25.5 | (−35.9, −15.0) | Synergistic |
| Compound III-1 (10 mg/kg) + Rituximab (10 mg/kg) | −4.3 | (−11.5, 2.9) | Additive |

Synergistic: score < 0, Additive: score = 0, Sub-Additive: score > 0. Assessment based on whether 95% confidence interval included the value 0.

All vehicle treated mice reached the pre-defined endpoint of paralysis and were euthanized between Day 21 and Day 31, however all mice in the two combination treatment groups were alive up to Day 1.32. By the end of the study (Day 132), the number of mice remaining in the single agent Compound III-1 3 mg/kg, Compound III-1 10 mg/kg and rituximab 10 mg/kg groups was 1 out of 10, 3 out of 10 and 1 out of 10 respectively. The median survival in days for each group is presented in Table 18. Log rank analysis, conducted to compare the survival rates between groups, showed that all treatment groups had significantly longer survival than the vehicle group, and all combination groups had significantly longer survival than each of the individual treatments (Table 16). Table 16 also shows the mean maximum body weight change of the groups from Day 0 to Day 24. The maximum body weight loss for vehicle group was 5.9% on Day 24. All other treatment groups gained weight during the study, including the single agent and combination agent groups. Treatment with Compound III-1 at 3 or 10 mg/kg on a QD schedule or rituximab at 10 mg/kg on a QW schedule was well tolerated.

TABLE 18

| Study/Cell Line/Treatment | Dose (mg/kg) | Method of Administration/ Frequency | Endpoints | Noteworthy Findings |
|---|---|---|---|---|
| Ly19-Luc Vehicle (10% HP-β-CD plus 1% NaHCO$_3$) | 0 | po/QD × 21 days | TGI[a] Median Survival (Days) BW change[b] | N/A 25 −5.9, Day 24 |
| Compound III-1 | 3 | po/QD × 21 days | TGI Median Survival (Days) BW change | 89.6, p < 0.001 40, p < 0.01[c] +6.2, Day 24 |
| Compound III-1 | 10 | po/QD × 21 days | TGI Median Survival (Days) BW change | 100, p < 0.001 63.5, p < 0.01 +3.3%, Day 24 |
| Compound III-1 + Rituximab | 3 10 | po/QD × 21 days IV/QW × 3 doses | TGI Median Survival (Days) BW change | 100, p < 0.001 >100, p < 0.01 +8.7%, Day 24 |
| Compound III-1 + Rituximab | 10 10 | po/QD × 21 days IV/QW × 3 doses | TGI Median Survival (Days) BW change | 100.3, p < 0.001 >100, p < 0,01 +4.5%, Day 24 |
| Rituximab | 10 | IV/QW × 3 doses | TGI Median Survival (Days) BW change | 99.6, p < 0.001 66, p < 0.01 +9.4%, Day 24 |

[a]TGI was calculated on Day 24, p values were calculated using a one-way ANOVA with p < 0.05 considered statistically significant
[b]Maximum body-weight change.
[c]Log-rank analysis was used to compare the survival rate of each treatment group to the vehicle group, p < 0.05 considered statistically significant, Experiment #2: Disseminated Ly19-Luc Lymphoma Model Mice were dosed according to the following treatment groups:

TABLE 19

Dosing regimen for mice in second disseminated Ly19 experimental group.

| Group | Test Article | Animals/ group | Dose Route | Dose (mg/kg) | Dose Regimen | Dose Solution (mg/ml) | Dose Volume (ml) |
|---|---|---|---|---|---|---|---|
| 1 | Vehicle | 10 | PO | 0 | QD | | 100 |
| 2 | Compound III-1 | 10 | PO | 3 | QD | 0.75 | 100 |
| 3 | Compound III-1 + Rituximab | 10 | PO/IV | 3/10 | QD/Q7D×3 | 0.75/2.5 | 100 |
| 4 | Rituximab | 10 | IV | 10 | Q7D×3 | 2.5 | 100 |
| 5 | Rituximab | 10 | IV | 5 | Q7D×3 | 1.25 | 100 |
| 6 | Rituximab | 10 | IV | 1 | Q7D×3 | 0.25 | 100 |
| 7 | Rituximab | 10 | IV | 0.5 | Q7D×3 | 0.025 | 100 |

Results

Mice were weighed and tumor volumes were estimated with Xenogen signal (average photon flux) calculation once a week throughout the inoculation and the treatment period and after the treatment until the end of study.

Treatment started 7 days following the inoculation of tumor cells into the tail vein, with an average photon flux measurement of $1\times10^7$ on treatment Day 0. The TGI, calculated on Day 23 (2 days post dose) was similar between treatment groups (75.8-100%). Tumor growth was significantly inhibited (P<0.001) in all groups including the single agents (Compound III-1 or rituximab) the combination of Compound III-1+ rituximab treatment group when compared to control (Table 20).

A clear dose response in the AUC values was observed in the rituximab treatment groups. The results of the linear regression model revealed that all of these differences relative to the vehicle group were significant (P<0.01, Table 21b). Additionally, the combination treatment group (Compound III-1 3 mg/kg+rituximab 10 mg/kg) showed a consistent decrease in tumor burden (−20.0), that was significantly lower than either of the respective single agents alone (Compound III-1 3 mg/kg and rituximab 10 mg/kg, P<0.01). In fact, the mice in this group had photon flux values that were in the un-inoculated, baseline range (photon flux=4-$7\times10^{\wedge}5$), suggesting the tumors had disappeared.

TABLE 20

TGI, tumor growth inhibition (TGI = 100 − [(MTV treated/MTV control) × 100];

| Group/Test Article | Dose (mg/kg) | N | Route & Schedule | Mean Photon Flux (Day 23) | TGI Day 23 | P-value |
|---|---|---|---|---|---|---|
| Group 1/Vehicle | — | 10 | PO QD × 3 wks | 1.84E+09 | — | |
| Group 2/Compound III-1 | 3 mg/kg | 10 | PO QD × 3 wks | 2.34E+08 | 87.7% | P < 0.001 |
| Group 3/Compound III-1/Rituximab | 3/10 mg/kg | 10 | PO QD × 3 wks IV Q7D × 3 wks | 9.13E+05 | 100% | P < 0.001 |
| Group 4/Rituximab | 10 mg/kg | 10 | IV Q7D × 3 dose | 8.43E+07 | 95.9% | P < 0.001 |
| Group 5/Rituximab | 5 mg/kg | 10 | IV Q7D × 3 dose | 1.57E+08 | 91.9% | P < 0.001 |
| Group 6/Rituximab | 1 mg/kg | 10 | IV Q7D × 3 dose | 3.52E+08 | 81.3% | P < 0.001 |
| Group 7/Rituximab | 0.1 mg/kg | 10 | IV Q7D × 3 dose | 4.52E+08 | 75.8 | P < 0.001 |

P < 0.001 as determined by ANOVA

To better compare tumor growth and the response to treatment between groups, mean AUC values were calculated for each group based on photon flux levels representing tumor burden. The AUC values from each group during the treatment period up to Day 23 (2 days post-treatment) are summarized in Table 21a.

TABLE 21a

Mean area under the $\log_{10}$ fold change vs day curves (AUC) for each treatment group. Negative values indicate decreased tumor burden.

| Treatment | Mean AUC |
|---|---|
| Vehicle | 30.4 |
| Rituximab (0.5 mg/kg Q7D) | 24.7 |
| Rituximab (1 mg/kg Q7D) | 18.8 |
| Rituximab (5 mg/kgQ7D) | 8.1 |
| Rituximab (10 mg/kg Q7D)) | 8.4 |
| Compound III-1 (3 mg/kg QD) | 18.2 |
| Compound III-1 (3 mg/kg QD + Rituximab 10 mg/kg Q7D) | −20.0 |

Average photon flux measurements increased approximately two logs in the vehicle group during the 23-day period, which was an average increase in tumor burden of nearly two-fold and resulted in a mean AUC of 30.4 (Table 21a). The AUCs, and therefore the tumor burden, were smaller in each of the treatment groups compared to vehicle.

TABLE 21b

Summary of mixed-effects linear regression results

| Treatment Group | Reference | P-value |
|---|---|---|
| Compound III-1 (3 mg/kg-QD) | Vehicle | <0.01 |
| Rituximab (0.5 mg/kg Q7D) | | 0.02 |
| Rituximab (1 mg/kg Q7D) | | 0.01 |
| Rituximab (5 mg/kg Q7D) | | <0.01 |
| Compound III-1 (3 mg/kg QD) + Rituximab (10 mg/kg Q7D) | | <0.01 |
| Compound III-1 (3 mg/kg QD) + Rituximab (10 mg/kg Q7D) | Compound III-1 (3 mg/kg QD) | <0.01 |
| Compound III-1 (3 mg/kg QD) + Rituximab (10 mg/kg Q7D) | Rituximab (10 mg/kg Q7D) | <0.01 |

A synergy score calculation was applied to these data to determine whether the effects of the combination treatment were synergistic, additive or sub-additive relative to the individual treatments. This analysis showed that the combination treatment with Compound III-1 at 3 mg/kg plus rituximab at 10 mg/kg was synergistic when comparing the $\log_{10}$-transformed fold changes (Table 22).

TABLE 22

| Combination | Synergy Score | 95% Confidence Interval | Assessment |
|---|---|---|---|
| Compound III-1 (3 mg/kg + Rituximab 10 mg/kg) | −46.6 | (−56.2, −37.0) | Synergistic |

Synergistic: score < 0, Additive: score = 0, Sub-Additive: score > 0. Assessment based on whether 95% confidence interval included the value 0.

Following treatment, tumor growth was monitored in remaining mice up to Day 125 to determine if tumors would re-grow after treatment ended. Mixed-effects piecewise linear regression models were built to compare the slope of the log flux between Days 9 and 23 to the slope between Days 23 and 125 (or earlier if all animals in a group died). Due to loss of mice from paralysis in many groups, only the combination Compound III-1 and rituximab group and the rituximab 10 and 5 mg/kg groups were evaluated. None of the groups had significantly different changes in slopes after treatment stopped on Day 23 (Table 23), indicating that tumor growth/inhibition did not significantly change following the cessation of treatment. These data suggest that the inhibitory effects of each of the respective treatments appear to continue up to 104 days following treatment.

TABLE 23

Breakpoint was set at Day 23. Difference was calculated as slope (Day 23 to 125) − slope (Day 9 to 23). P-values < 0.05 indicate that the difference in slope was significantly different than zero.

| Treatment Group | Difference in Slope | P-value |
|---|---|---|
| Rituximab (5 mg/kg) | −0.01 | 0.49 |
| Rituximab (10 mg/kg) | −0.01 | 0.40 |
| Compound III-1 (3 mg/kg + Rituximab 10 mg/kg) | 0.00 | 0.86 |

Individual whole body bioluminescence images were taken of all mice in all treatment groups using the Xenogen IVIS® imaging system. Tumor presence/growth in each mouse was assessed using this system prior to treatment on Day 0; 3 days before the end of treatment (Day 18); and 104 days following the end of treatment (Day 125). On Day 18 there is a striking reduction in the fluorescent signal of the tumor as a result of treatment with the combination Compound III-1 at 3 mg/kg with rituximab as compared to any of the other treatment groups or control group. Mice receiving combination treatments show little or no evidence of the disseminated lymphoma tumor, whereas tumor growth was evident in the single agent Compound III-13 mg/kg group and all of the single agent rituximab treatment groups. Bioluminescence images of mice in the combination treatment group, i.e., Compound III-1 at 3 mg/kg with rituximab, on Day 125, show no evidence of tumor growth. Due to the loss of mice from paralysis in the other treatment groups, bioluminescence imaging was not conducted in these groups.

All vehicle treated mice reached the pre-defined endpoint of paralysis and were euthanized between Day 21 and Day 31. A dose response was observed in the survival rate of rituximab treated mice with 3/10, 1/10, 1/10 and 0/10 mice remaining by Day 125 in the 10, 5, 1 and 0.5 mg/kg groups respectively. Log rank analysis, conducted to compare the survival rates between groups, demonstrates that all treatment groups had significantly longer survival than the vehicle group, and the combination group had significantly longer survival than each of the individual treatments. None of the mice in the combination treatment group were removed during the 125 days of the study Table 24 shows the mean maximum body weight change of the groups from Day 0 to Day 22 of the study. The maximum body weight loss for vehicle group was 1.75% on Day 22. All other treatment groups gained weight during the study, including the single agent and combination agent groups. Treatment with Compound III-1 at 3 mg/kg on a QD schedule, or rituximab up to 10 mg/kg on a Q7D schedule, were well tolerated.

TABLE 24

Body weight (BW) change

| Test Article | Dose (mg/kg) | N | Route & Schedule | Mean BW Day 0 | Mean BW Day 22 | Maximum BW Change (%) Day 22 |
|---|---|---|---|---|---|---|
| Vehicle | — | 10 | PO QD × 3 wks | 19.46 | 19.12 | −1.75 |
| Compound III-1 | 3 mg/kg | 10 | PO QD × 3 wks | 19.20 | 19.81 | +3.1 |
| Compound III-1/ Rituximab | 3 mg/kg 10 mg/kg | 10 | PO QD × 3 wks/ IV Q7D × 3 dose | 18.02 | 18.21 | +1.05 |
| Rituximab | 10 mg/kg | 10 | IV Q7D × 3 dose | 19.11 | 19.72 | +3.19 |
| Rituximab | 5 mg/kg | 10 | IV Q7D × 3 dose | 18.55 | 19.55 | +5.39 |
| Rituximab | 1 mg/kg | 10 | IV Q7D × 3 dose | 19.43 | 20.25 | +4.22 |
| Rituximab | 0.5 mg/kg | 10 | IV Q7D × 3 dose | 19.30 | 20.27 | +5.02 |

Conclusions

In vivo imaging experiments in SCID mice bearing Ly19-Luc disseminated lymphoma tumors were performed in duplicate in order to confirm the effects of Compound III-1 and rituximab as single agents and as combination treatment. Tumor burden and TGI were determined using quantitative Xenogen imaging in mice receiving various doses of Compound III-1 with and without 10 mg/kg of rituximab. Tumor growth was significantly inhibited in all treatment groups (P<0.001). Tumor burden, presented as the AUC of photon flux values during the treatment period, was significantly lower in all treatment groups compared to control. Combination treatment with Compound III-1 at 3 mg/kg and rituximab at 10 mg/kg appears to provide a synergistic effect that significantly lowered tumor burden when compared to either of the agents alone, thereby corroborating the synergistic effect observed in the sub-cutaneous Ly19 lymphoma model discussed above (refer to Example 1). The survival of the animals was significantly higher in each of the treatment groups compared to the vehicle group and significantly higher in the combination groups compared to the respective individual treatments. Following treatment, there were no significant changes in tumor growth rates in any of the groups up to 52 days in the first replicate and 125 days in the second replicate. In summary, results from the two experiments are consistent with one another and these data confirm that a combination of Compound III-1 and rituximab is the most effective treatment for disseminated Ly19-Luc lymphoma in SCID mice, resulting in a reduction of tumor burden to undetectable levels.

Experiment 5: Combination of Aurora a Kinase Specific Inhibitor (Compound III-1) and Rituximab in a Disseminated Lymphoma Model of WSU-DLBCL2-Luc Cell Line Grown in Female SCID Mice Experimental Overview Two separate studies were conducted in the WSU-DLBCL2-luc model. Compound III-1 was administered initially at low doses (3 or 10 mg/kg on a QD schedule) alone and in combination with rituximab, or at higher doses (10 or 20 mg/kg on a BID schedule) alone or in combination with rituximab. After treatment, animals were monitored up to Day 132 to compare the survival between treatment groups and vehicle.

In the first WSU-DLBCL2 study, Compound III-1 when dosed alone at either 3 mg/kg or 10 mg/kg QD did not significantly inhibit tumor growth in this model (TGI=50.9%, p>0.05, TGI=88.2%, p>0.05 respectively). Rituximab dosed alone (10 mg/kg QW) or in combination with Compound III-1 at 3 or 10 mg/kg significantly inhibited tumor growth (TGI=83.6%, p<0.05, TGI=91.8%, p<0.05, TGI=99.0%, p<0.001 respectively) in SCID mice bearing WSU-DLCL2-Luc xenografts (Table 25). In the second study, when Compound III-1 was dosed alone at either 10 mg/kg or 20 mg/kg BID, tumor growth was significantly inhibited in this model (TGI=99.7%, p<0.001, for both groups). Rituximab dosed alone at 10 mg/kg QW (TGI=88.4%, p<0.001) and in combination with Compound III-1 at 10 or 20 mg/kg BID resulted in significant tumor growth inhibition (TGI=99.6% and 99.9% respectively, p<0.001 for both), (Table 25).

TABLE 25

Tumor Growth Inhibition, Body Weight Change and Survival

| | Dose (mg/kg)[b] | Route and Dose Regimen | Maximum Percent Body Weight Change (%) | TGI Mean (%)[c] | TGI p Value[d] | Survival Median Survival (Days) | Survival p Value[d] |
|---|---|---|---|---|---|---|---|
| 1st WSU-DLBCL2 Study/Treatment Group[a] | | | | | | | |
| Vehicle[f] | 0 | po/QD × 21 days | −0.3, Day 21 | N/A | N/A | 37 | N/A |
| Compound III-1 | 3 | po/QD × 21 days | −3.1, Day 21 | 50.9, Day 21 | >0.05 | 46.5 | 0.040 |
| Compound III-1 Rituximab | 3 10 | po/QD × 21 days IV/QW × 3 doses | −2.4, Day 21 | 91.8, Day 21 | <0.05 | 73 | 0.003 |
| Compound III-1 | 10 | po/QD × 21 days | −4.5, Day 21 | 88.2, Day 21 | >0.05 | 44 | 0.017 |
| Compound III-1 Rituximab | 10 10 | po/QD × 21 days IV/QW × 3 doses | −2.8, Day 21 | 99.0, Day 21 | <0.001 | 52.5 | <0.001 |
| Rituximab | 10 | IV/QW × 3 doses | +1.7, Day 21 | 83.6, Day 21 | <0.05 | 61 | <0.001 |
| 2nd WSU-DLBCL2 study | | | | | | | |
| Vehicle | 0 | po/BID × 21 days | +2.5, Day 22 | N/A | N/A | 45 | N/A |
| Compound III-1 | 10 | po/BID × 21 days | −3.9, Day 19 | 99.7, Day 22 | <0.001 | 70 | <0.001 |
| Compound III-1[g] | 20 | po/QD × 21 days | −8.9, Day 9 | 99.7, Day 22 | <0.001 | 111.5 | <0.001 |
| Compound III-1 Rituximab | 10 10 | po/BID × 21 days IV/QW × 3 doses | −1.7, Day 19 | 99.6, Day 22 | <0.001 | 121 | <0.001 |

TABLE 25-continued

Tumor Growth Inhibition, Body Weight Change and Survival

| | Dose (mg/kg)[b] | Route and Dose Regimen | Maximum Percent Body Weight Change (%) | TGI Mean (%)[c] | p Value[d] | Survival Median Survival (Days) | p Value[d] |
|---|---|---|---|---|---|---|---|
| Compound III-1[g] Rituximab | 20 10 | po/BID × 21 days IV/QW × 3 doses | −12.2, Day 9 | 99.9, Day 22 | <0.001 | >128 | <0.001 |
| Rituximab | 10 | IV/QW × 3 doses | +6.3, Day 22 | 88.4, Day 22 | <0.001 | 59 | >0.05 |

[a]There were 10 mice in each treatment group.
[b]For each dose, mice received 100 μL of Compound III-1 and/or rituximab dosing solution prepared at 0.75, 2.5, 5.0 and 7.5 mg/mL (3, 10, 20, 30 mg/kg Compound III-1) or 2.0 mg/mL (10 mg/kg rituximab). These dosing solutions were prepared routinely based on historical mouse body weights of 25 or 20 grams respectively. All doses were approximate.
[c]Mean tumor volumes, and TGI values were calculated on Day 21 (1st study) and Day 22 (2nd study) of treatment.
[d]TGI = TGI calculation B − tumor growth inhibition (TGI = [(Δ control average volume − Δ treated average volume) × 100/Δ control average volume]. p values were calculated with an ANOVA, p < 0.05 considered statistically significant
[e]Log-rank analysis was used to compare the survival rate of each treatment group to the vehicle group, p < 0.05 considered statistically significant.
[f]The vehicle used in TGI and the treatment groups was 10% HP-β-CD plus 1% NaHCO. The vehicle used in the rituximab treatment groups was 0.9% saline.
[g]Animals dosed with Compound III-1 at 20 mg/kg BID, and animals in the combination group dosed with 20 mg/kg Compound III-1 and rituximab at 10 mg/kg QW received a dose holiday for 5 days, from Day 9 to Day 13.

After treatment, animals were monitored for survival up to Day 125 (1st study) or Day 130 (2nd study). The median survival in days for each group is presented in Table 25 and the mean survival rate of the treatment groups were compared to the vehicle group. In the 1st study, all vehicle animals were euthanized at the humane endpoint (paralysis) by Day 44 and all treatment groups showed significantly longer survival relative to the vehicle group (p<0.04-0.001, Table 25). By the end of the study (Day 125), 1 out of 10 mice remained in the single agent rituximab group and in the 10 mg/kg Compound III-1 combination treatment group. In the 2nd study, all vehicle animals were euthanized at the humane endpoint by Day 68. With the exception of rituximab treatment alone (p>0.05), all treatment groups showed significantly longer survival relative to the vehicle group (p<0.001, Table 25). The number of mice remaining at the end of the study (Day 130) was 1 out of 10 in the 10 mg/kg single agent Compound III-1 and rituximab groups, 5 out of 10 in the 20 mg/kg Compound III-1 single agent group and the 10 mg/kg Compound III-1 combination group, and 8 out of 10 mice in the 20 mg/kg Compound III-1 combination group.

The tumor volumes were smaller in each of the treatment groups in the first study compared to vehicle (Table 26a). Both combinations groups were additive relative to their respective individual treatments when comparing AUC values (Table 26b).

TABLE 26a

Area Under the Curve Efficacy and Synergy Analysis
(Days 0 Through 21) for first study.

| Treatment | Pct Decrease in AUC Relative to Mean Vehicle AUC |
|---|---|
| Vehicle | — |
| Compound III-1 (3 mg/kg, PO, QD) | 21.1 |
| Compound III-1 (10 mg/kg, PO, QD) | 42.0 |
| Rituximab (10 mg/kg, IV, QW) | 44.4 |
| Compound III-1 (3 mg/kg) + Rituximab (10 mg/kg) | 48.6 |
| Compound III-1 (10 mg/kg) + Rituximab (10 mg/kg) | 75.0 |

Average percent change in the area under the $\log_{10}$ photon flux vs day curves (AUC) relative to the mean AUC of the vehicle group.

TABLE 26b

Area Under the Curve Efficacy and Synergy Analysis
(Days 0 Through 21) for first study.

| Combination | Synergy Score | 95% Confidence Interval | P Value | Assessment |
|---|---|---|---|---|
| Compound III-1 (3 mg/kg QD) + Rituximab | 16.9 | (−10.8, 44.6) | 0.22 | Additive |
| Compound III-1 (10 mg/kg QD) + Rituximab | 11.3 | (−12.5, 35.1) | 0.33 | Additive |

Synergistic: score < 0, Additive: score = 0, Sub-additive: score > 0. Assessment based on whether the synergy score was significantly different from 0.

The tumor volumes were smaller in each of the treatment groups in the second study compared to vehicle (Table 27a). Both combinations groups were sub-additive relative to their respective individual treatments when comparing AUC values (Table 27b).

TABLE 27a

Area Under the Curve Efficacy and Synergy Analysis
(Days 0 Through 21) for second study.

| Treatment | Pct Decrease in AUC Relative to Mean Vehicle AUC |
|---|---|
| Vehicle | — |
| Compound III-1 (10 mg/kg, PO, BID) | 94.0 |
| Compound III-1 (20 mg/kg, PO, BID) | 96.6 |
| Rituximab (10 mg/kg, IV, QW) | 41.3 |
| Compound III-1 (10 mg/kg) + Rituximab (10 mg/kg) | 98.5 |
| Compound III-1 (20 mg/kg) + Rituximab (10 mg/kg) | 100.2 |

Average percent change in the area under the $\log_{10}$ photon flux vs day curves (AUC) relative to the mean AUC of the vehicle group.

TABLE 27b

Area Under the Curve Efficacy and Synergy Analysis
(Days 0 Through 21) for second study.

| Combination | Synergy Score | 95% Confidence Interval | P Value | Assessment |
|---|---|---|---|---|
| Compound III-1 (10 mg/kg QD) + Rituximab | 36.8 | (12.4, 61.2) | 0.005 | Sub-Additive |
| Compound III-1 (20 mg/kg QD) + Rituximab | 37.7 | (15.5, 59.9) | 0.003 | Sub-Additive |

Synergistic: score < 0, Additive: score = 0, Sub-additive: score > 0. Assessment based on whether the synergy score was significantly different from 0.

At the end of dosing on Day 21 of the 1st study, body weight loss was less than 5% for all groups (Table 25). In the second study, however, treatment with Compound III-1 at 20 mg/kg on a BID schedule and the combination treatment of Compound III-1 at 20 mg/kg BID with rituximab at 10 mg/kg QW resulted in mean maximum body weight losses of 8.9% (Day 9) and 12.2% (Day 9) respectively. This effect was managed by giving all animals in these groups a 5 day dose holiday (Day 9 through Day 13); animals then regained body weight. No other treatment group exhibited a maximum body weight loss greater than 3.9% (Table 25).

While the foregoing invention has been described in some detail for purposes of clarity and understanding, these particular embodiments are to be considered as illustrative and not restrictive. It will be appreciated by one skilled in the art from a reading of this disclosure that various changes in form and detail can be made without departing from the true scope of the invention, which is to be defined by the appended claims rather than by the specific embodiments.

The patent and scientific literature referred to herein establishes knowledge that is available to those with skill in the art. Unless otherwise defined, all technical and scientific terms used herein have the same meaning as commonly understood by one of ordinary skill in the art to which this invention belongs. The issued patents, applications, and references that are cited herein are hereby incorporated by reference to the same extent as if each was specifically and individually indicated to be incorporated by reference. In the case of inconsistencies, the present disclosure, including definitions, will control.

What is claimed is:

1. A method of treating a human patient suffering from a hematological malignancy, comprising administering to the human patient an Aurora kinase inhibitor, wherein the Aurora kinase inhibitor is 4-{[9-chloro-7-(2-fluoro-6-methoxyphenyl)-5H-pyrimido[5,4-d][2]benzazepin-2-yl]amino}-2-methoxybenzoic acid, or a pharmaceutically acceptable salt thereof, simultaneously with or consecutively with an anti-CD20 antibody, wherein the anti-CD20 antibody is rituximab,
  wherein the Aurora kinase inhibitor is administered to the human patient at a dose that is equivalent to an average daily dose (QD) in a mouse of about 3 mg/kg, and the anti-CD20 antibody is administered to the human patient at a dose that is equivalent to an average weekly dose (QW) in a mouse of about 10 mg/kg.

2. The method of claim 1, wherein the hematological malignancy is selected from the group consisting of lymphoma, leukemia and multiple myeloma.

3. The method of claim 2, wherein the lymphoma is selected from the group consisting of B-cell lymphoma, Non-Hodgkin's lymphoma and mantle cell lymphoma.

4. The method of claim 1, wherein the human patient was treated previously with an anti-CD20 antibody.

5. The method of claim 1, wherein the Aurora kinase specific inhibitor is sodium 4-{[9-chloro-7-(2-fluoro-6-methoxyphenyl)-5H-pyrimido[5,4-d][2]benzazepin-2-yl]amino}-2-methoxybenzoate.

* * * * *